United States Patent
Gupta et al.

(10) Patent No.: US 10,548,270 B2
(45) Date of Patent: Feb. 4, 2020

(54) MANIPULATION OF GLUTAMINE SYMTHETASES (GS) TO IMPROVE NITROGEN USE EFFICIENCY AND GRAIN YIELD IN HIGHER PLANTS

(71) Applicant: PIONEER HI-BRED INTERNATIONAL, INC., Johnston, IA (US)

(72) Inventors: Rajeev Gupta, Johnston, IA (US); Kanwarpal Singh Dhugga, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 22 days.

(21) Appl. No.: 14/626,178

(22) Filed: Feb. 19, 2015

(65) Prior Publication Data
US 2016/0108415 A1    Apr. 21, 2016

Related U.S. Application Data

(60) Continuation of application No. 13/623,938, filed on Sep. 21, 2012, now abandoned, which is a division of application No. 12/607,089, filed on Oct. 28, 2009, now abandoned.

(60) Provisional application No. 61/109,651, filed on Oct. 30, 2008.

(51) Int. Cl.
*C12N 15/63* (2006.01)
*A01H 1/00* (2006.01)
*C12N 15/82* (2006.01)

(52) U.S. Cl.
CPC .............. *A01H 1/00* (2013.01); *C12N 15/63* (2013.01); *C12N 15/8261* (2013.01)

(58) Field of Classification Search
None
See application file for complete search history.

(56) References Cited

U.S. PATENT DOCUMENTS

| 7,138,278 B2 | 11/2006 | Hinchey et al. | |
| 2004/0214272 A1* | 10/2004 | La Rosa | C07H 21/04 435/69.1 |
| 2006/0048240 A1 | 3/2006 | Alexandrov et al. | |
| 2007/0300323 A1 | 12/2007 | Hershey et al. | |

FOREIGN PATENT DOCUMENTS

WO    2007/092704    *   8/2007

OTHER PUBLICATIONS

Sakakibara et al., Molecular Cloning of the Family of Glutamine Synthetase Genes from Maize: Expression of Genes for Glutamine Synthetase and Ferredoxin-Dependent Glutamate Synthase in Photosynthetic and Non-Photosynthetic Tissues, Plant Cell Physiol. (1992), 33(1): 49-58, XP009084356.
NCBI Accession No. D14579, (1997), XP-002561403.
Bernard, et al, The importance of cytosolic glutamine synthetase in nitrogen assimilation and recycling, New Phytologist, (2009), 182:608-620.
Broyart, et al., Metabolic profiling of maize mutants deficient for two glutamine synthetase isoenyzmes using $^1$H-NMR-based metabolomics, Phytochemical Analysis (2010), 21:102-109.
El Omari R., et al., Ammonium tolerance and the regulation of two cytosolic glutamine synthetases in the roots of sorghum, Functional Plant Biology (2010), 37:55-63.
Purcino, et al., Glutamine synthetase response to nitrate in maize genotyhpes of contrasting nitrogen use efficiency, Maydica, (2008), 53:101-109.
Valadier, et al., Implication of the glutamine synthetase/glutamate synthase pathway in conditioning the amino acid metabolism in bundle sheath and mesophyll cells of maize leaves, FEBS Journal (2008), 275:3193-3206.
Coque, et al., Genetic variation for N-remobilization and postsilking N-uptake in a set of maize recombinannt inbred lines. 3 QTL detection and coincidences, Theoretical and Applied Genetics (2008), 117:729-747.
Martin, et al., Two cytosolic glutamine synthetase isoforms of maize are specifically involved in the control of grain production, Plant Cell (2006), 18:3252-3274.

* cited by examiner

*Primary Examiner* — Phuong T Bui

(57) ABSTRACT

The present invention provides polynucleotides and related polypeptides of the protein GS. The invention provides genomic sequence for the GS gene. GS is responsible for controlling nitrogen utilization efficiency in plants. Glutamine synthase sequences are provided for improving grain yield and plant growth. The invention further provides recombinant expression cassettes, host cells and transgenic plants.

5 Claims, 27 Drawing Sheets

Specification includes a Sequence Listing.

FIG.1A

```
                                      66                                                                                                130
SEQ ID NO 02 (AT1G48470)         (4)  PLSDLLNLDLSDTK-KIIAEYIWIGGSGMDIRSKARTLPGPVSNPTKLPKWNYDGSSTDQAAGDD
SEQ ID NO 06 (AT3G17820)         (3)  LLSDLVNLNLTDATGKIIAEYIWIGGSGMDIRSKARTLPGPVTDPSKLPKWNYDGSSTGQAAGED
SEQ ID NO 34 (Os03g50490)        (5)  LLTDLVNLDLSESTDKVIAEYIWVGGTGMDVRSKARTLSGPVDDPSKLPKWNFDGSSTGQATGDD
SEQ ID NO 46 (ZmGS1-2)           (3)  LLSDLINLDLSGRTGKIIAEYIWVGGSGMDVRSKARTLPGPVDDPSKLPKWNFDGSSTGQAPGDD
SEQ ID NO 04 (AT1G66200)         (3)  LLADLVNLDISDNSEKIIAEYIWIGGSGMDMRSKARTLPGPVTDPSKLPKWNYDGSSTGQAPGQD
SEQ ID NO 12 (AT5G37600)         (3)  LVSDLINLNLSDSTDKIIAEYIWIGGSGMDMRSKARTLPGPVTDPSQLPKWNYDGSSTGQAPGED
SEQ ID NO 08 (AT5G16570)         (3)  SLADLINLDLSDSTDQIIAEYIWIGGSGLDMRSKARTLPGPVTDPSQLPKWNYDGSSTGQAPGDD
SEQ ID NO 10 (AT5G35630)        (61)  RVETLLNLDTKPYSDRIIAEYIWIGGSGIDLRSKSRTIEKPVEDPSELPKWNYDGSSTGQAPGDD
SEQ ID NO 18 (Gm0030x00147)     (63)  RLEGLLNLDITPFTDKIIAEYIWIGGTGIDVRSKSRTISKPVEDPSELPKWNYDGSSTGQAPGDD
SEQ ID NO 28 (Gm0271x00039)     (63)  RLEGLLNLDITPFTDKIIAEYIWIGGTGIDVRSKSRTISKPVEHPSELPKWNYDGSSTGQAPGDD
SEQ ID NO 36 (Os04g56400)       (59)  RMEQLLNMDTTPFTDKIIAEYIWVGGTGIDLRSKSRTISKPVEDPSELPKWNYDGSSTGQAPGED
SEQ ID NO 42 (Sb06g147820)      (64)  RLEQLLNMDTTPYTDKIIAEYICP---------------------------------------
SEQ ID NO 54 (ZmGS2)            (54)  RLEQLLNMDTTPYTDKVIAEYIWIGGSGIDIRSKSRTISKPVEDPSELPKWNYDGSSTDQAPGDD
SEQ ID NO 32 (Os03g12290)        (3)  NLTDLVNLNLSDCSDKIIAEYIWIGGSGIDLRSKARTVKGPITDVSQLPKWNYDGSSTGQAPGDD
SEQ ID NO 38 (Sb01g143820)       (3)  SLTDLVNLDLSDCTDKIIAEYIWIGGSGIDLRSKARTVKGPITDPSQLPKWNYDGSSTGQAPGDD
SEQ ID NO 44 (ZmGS1-1)           (3)  SLTDLVNLDLSDCTDRIIAEYIWIGGTGIDLRSKARTVKGPITDPIQLPKWNYDGSSTGQAPGDD
SEQ ID NO 52 (ZmGS1-5)           (3)  SLTDLVNLDLSDCTDRIIAEYIWVGGSGIDLRSKARTVKGPITDPSQLPKWNYDGSSTGQAPGDD
SEQ ID NO 14 (Gm0005x00111)      (3)  LLSDLINLSESTEKIIAEYIVAEYIWIGGSGMDLRSKARTLPGPVSDPAKLPKWNYDGSSTDQAPGDD
SEQ ID NO 26 (Gm0232x00015)      (3)  LLSDLINLSESTEKIIAEYIWVGGSGMDLRSKARTLPGPVSDPAKLPKWNYDGSSTDQAPGDD
SEQ ID NO 22 (Gm0081x00134)      (3)  LLSDLINLSDTTEKVIAEYIWIGGSGMDLRSKARTLPGPVSDPSELPKWNYDGSSTGQAPGDD
SEQ ID NO 24 (Gm0136x00208)      (3)  LLSDLINLSDTTEKIIAEYIWIGGSGMDLRSKARTLSGLVNDPSKLPKWNYDGSSTGQAPGDD
SEQ ID NO 16 (Gm0015x00387)      (3)  LLSDLINLNLSDIT-------------DKTLSGPVKDPSKLPKWNYDGSSTGQAPGQD
SEQ ID NO 20 (Gm0040x00114)      (3)  SLTDLVNLSLSDTTEKIIAEYIWIGGSGMDLRSKARTLSGPVTDPSKLPKWNYDGSSTGQAPGED
SEQ ID NO 30 (Os02g50240)        (3)  SLTDLVNLSLSDTTEKIIAEYIWIGGSGMDLRSKARTLPGPVTDPSKLPKWNYDGSSTGQAPGED
SEQ ID NO 40 (Sb04g133790)       (3)  CLTDLVNLNLSDTTEKIIAEYIWIGGSGMDLRSKARTLPGPVTDPSKLPKWNYDGSSTGQAPGED
SEQ ID NO 48 (ZmGS1-3)           (3)  CLTDLVNLNLSDTTEKIIAEYIWIGGSGMDLRSKARTLPGPVTDPSKLPKWNYDGSSTGQAPGED
SEQ ID NO 50 (ZmGS1-4)          (66)  LSDLVNLDLSD TDKIIAEYIWIGGSGMDLRSKARTL GPVTDPSKLPKWNYDGSSTGQAPGED
Consensus
```

| | | |
|---|---|---|
| SEQ ID NO 02 (AT1G48470) | (133) | ------------------------------------------------------------- |
| SEQ ID NO 06 (AT3G17820) | (133) | ------------------------------------------------------------- |
| SEQ ID NO 34 (Os03g50490) | (135) | ------------------------------------------------------------- |
| SEQ ID NO 46 (ZmGS1-2) | (133) | ------------------------------------------------------------- |
| SEQ ID NO 04 (AT1G66200) | (133) | ------------------------------------------------------------- |
| SEQ ID NO 12 (AT5G37600) | (133) | ------------------------------------------------------------- |
| SEQ ID NO 08 (AT5G16570) | (133) | ------------------------------------------------------------- |
| SEQ ID NO 10 (AT5G35630) | (191) | ------------------------------------------------------------- |
| SEQ ID NO 18 (Gm0030x00147) | (193) | ------------------------------------------------------------- |
| SEQ ID NO 28 (Gm0271x00039) | (193) | ------------------------------------------------------------- |
| SEQ ID NO 36 (Os04g56400) | (189) | ------------------------------------------------------------- |
| SEQ ID NO 42 (Sb06g147820) | (146) | ------------------------------------------------------------- |
| SEQ ID NO 54 (ZmGS2) | (184) | ------------------------------------------------------------- |
| SEQ ID NO 32 (Os03g12290) | (133) | ------------------------------------------------------------- |
| SEQ ID NO 38 (Sb01g143820) | (133) | ------------------------------------------------------------- |
| SEQ ID NO 44 (ZmGS1-1) | (133) | ------------------------------------------------------------- |
| SEQ ID NO 52 (ZmGS1-5) | (133) | ------------------------------------------------------------- |
| SEQ ID NO 14 (Gm0005x00111) | (133) | ------------------------------------------------------------- |
| SEQ ID NO 26 (Gm0232x00015) | (133) | ------------------------------------------------------------- |
| SEQ ID NO 22 (Gm0081x00134) | (133) | ------------------------------------------------------------- |
| SEQ ID NO 24 (Gm0136x00208) | (133) | ------------------------------------------------------------- |
| SEQ ID NO 16 (Gm0015x00387) | (133) | ------------------------------------------------------------- |
| SEQ ID NO 20 (Gm0040x00114) | (113) | GPYYCGTGANKAFGRDIVDSHYKACIYAGINISGINGEVMPGQRITEIAGVVLSFDPKPIQSMRN |
| SEQ ID NO 30 (Os02g50240) | (133) | ------------------------------------------------------------- |
| SEQ ID NO 40 (Sb04g133790) | (132) | ------------------------------------------------------------- |
| SEQ ID NO 48 (ZmGS1-3) | (133) | ------------------------------------------------------------- |
| SEQ ID NO 50 (ZmGS1-4) | (133) | ------------------------------------------------------------- |
| Consensus | (196) | |

FIG. 1D

```
                          261                                                              325
SEQ ID NO 02 (AT1G48470) (133) ----------------------------------TLLKKDVKWPLGWPLGGFPGPQ-----
SEQ ID NO 06 (AT3G17820) (133) ----------------------------------TLMQKDVNWPIGWPVGGYPGPQ-----
SEQ ID NO 34 (Os03g50490)(135) ----------------------------------TLLQKHINWPLGWPLGGYPGPQ-----
   SEQ ID NO 46 (ZmGS1-2)(133) ----------------------------------TLLQKDTKWPLGWPLA-YPGPQ-----
SEQ ID NO 04 (AT1G66200) (133) ----------------------------------TLLQKDVNWPLGWPIGGFPGPQ-----
SEQ ID NO 12 (AT5G37600) (133) ----------------------------------TLLQKDVKWPVGWPIGGYPGPQ-----
SEQ ID NO 08 (AT5G16570) (133) ----------------------------------TLLQKDIKWPVGWPVGGYPGPQ-----
SEQ ID NO 10 (AT5G35630) (191) ----------------------------------TLLQQNVKWPLGWPVGGAFPGPQ-----
SEQ ID NO 18 (Gm0030x00147)(193) ----------------------------------TLLQTNVKWPLGWPVGGYPGPQ-----
SEQ ID NO 28 (Gm0271x00039)(193) ----------------------------------TLLQTNVKWPLGWPVGGYPGPQ-----
SEQ ID NO 36 (Os04g56400)(189) ----------------------------------TLLQRDVNWPLGWPLGGYPGPQ-----
SEQ ID NO 42 (Sb06g147820)(146) ----------------------------------TLLQKDVNWPLGWPLGGFPGPQ-----
   SEQ ID NO 54 (ZmGS2) (184) ----------------------------------TLLQKDVNWPLGWPVGGFPGPQ-----
SEQ ID NO 32 (Os03g12290)(133) ----------------------------------TLLQKDVNWPLGWPVGGYPGPQ-----
SEQ ID NO 38 (Sb01g143820)(133) ---------------------------------TLLQKDVSWPLGWPVGGYPGPQ-----
   SEQ ID NO 44 (ZmGS1-1)(133) ----------------------------------TLLQKDVSWPLGWPVGGFPGPQ-----
   SEQ ID NO 52 (ZmGS1-5)(133) ----------------------------------TLLQKDVNWPLGWPLGGFPGPQ-----
SEQ ID NO 14 (Gm0005x00111)(133) ---------------------------------TLLQKDVNWPLGWPLGGFPGPQ-----
SEQ ID NO 26 (Gm0232x00015)(133) ---------------------------------TLLQKDIQWPLGWPVGGFPGPQ-----
SEQ ID NO 22 (Gm0081x00134)(133) ---------------------------------TLLQKDVQWPLGWPLGGFPGPQ-----
SEQ ID NO 24 (Gm0136x00208)(133) ---------------------------------TLLQKDVQWPLGWPLGGFPGPQ-----
SEQ ID NO 16 (Gm0015x00387)(133) ---------------------------------TLLQKDVQWPLGWPLGGFPGPQ-----
SEQ ID NO 20 (Gm0040x00114)(178) DGGYEVIKKAIAKLEKRHKEHIAAYGEGNERRLTGRHETADMNTFVWSCQWCWVEVGHNGVWWV
   SEQ ID NO 30 (Os02g50240)(133) ---------------------------------TLLQKDINWPLGWPVGGFPGPQ-----
   SEQ ID NO 40 (Sb04g133790)(132) --------------------------------TLLQKDTNWPLGWPLGGFPGPQ-----
   SEQ ID NO 48 (ZmGS1-3)(133) ----------------------------------TLLQKDTNWPLGWPIGGFPGPQ-----
   SEQ ID NO 50 (ZmGS1-4)(133) ----------------------------------TLLQKDTNWPLGWPIGGFPGPQ-----
              Consensus  (261)                                   TLLQKDVNWPLGWPVGGFPGPQ
```

FIG. 1E

```
                                   326                                                                            390
SEQ ID NO 02 (AT1G48470)   (155) ---------------------------------------------------------------GPYYCAVGVGADKA
SEQ ID NO 06 (AT3G17820)   (155) ---------------------------------------------------------------GPYYCGVGADKA
SEQ ID NO 34 (Os03g50490)  (157) ---------------------------------------------------------------GPYYCAAGADKS
SEQ ID NO 46 (ZmGS1-2)     (154) ---------------------------------------------------------------GPYYCAAGADKS
SEQ ID NO 04 (AT1G66200)   (155) ---------------------------------------------------------------GPYYCSIGADKS
SEQ ID NO 12 (AT5G37600)   (155) ---------------------------------------------------------------GPYYCGIGADKS
SEQ ID NO 08 (AT5G16570)   (155) ---------------------------------------------------------------GPYYCGVGADKA
SEQ ID NO 10 (AT5G35630)   (213) ---------------------------------------------------------------GPYYCGVGADKI
SEQ ID NO 18 (Gm0030x00147)(215) ---------------------------------------------------------------GPYYCSAGADKS
SEQ ID NO 28 (Gm0271x00039)(215) ---------------------------------------------------------------GPYYCSAGADKS
SEQ ID NO 36 (Os04g56400)  (211) ---------------------------------------------------------------GPYYCAVGSDKS
SEQ ID NO 42 (Sb06g147820) (168) ---------------------------------------------------------------GPYYCAVGADKS
SEQ ID NO 54 (ZmGS2)       (206) ---------------------------------------------------------------GPYYCAVGADKS
SEQ ID NO 32 (Os03g12290)  (155) ---------------------------------------------------------------GPYYCAAGAEKA
SEQ ID NO 38 (Sb01g143820) (155) ---------------------------------------------------------------GPYYCAAGADKA
SEQ ID NO 44 (ZmGS1-1)     (155) ---------------------------------------------------------------GPYYCAAGADKA
SEQ ID NO 52 (ZmGS1-5)     (155) ---------------------------------------------------------------GPYYCGTGADKA
SEQ ID NO 14 (Gm0005x00111)(155) ---------------------------------------------------------------GPYYCGIGADKA
SEQ ID NO 26 (Gm0232x00015)(155) ---------------------------------------------------------------GPYYCGVGADKA
SEQ ID NO 22 (Gm0081x00134)(155) ---------------------------------------------------------------GPYYCGVGADKA
SEQ ID NO 24 (Gm0136x00208)(155) ---------------------------------------------------------------GPYYCGVGADKA
SEQ ID NO 16 (Gm0015x00387)(155) ---------------------------------------------------------------GPYYCGTGANKA
SEQ ID NO 20 (Gm0040x00114)(243) ATEVVLSVWVFLEVQEVKRVMQEVKDGKHSFDFLKMSLLSDLININLSDTTKKGPYYCGIGANKA
SEQ ID NO 30 (Os02g50240)  (155) ---------------------------------------------------------------GPYYCGIGADKS
SEQ ID NO 40 (Sb04g133790) (154) ---------------------------------------------------------------GPYYCGIGADKS
SEQ ID NO 48 (ZmGS1-3)     (155) ---------------------------------------------------------------GPYYCGIGAEKS
SEQ ID NO 50 (ZmGS1-4)     (155) ---------------------------------------------------------------GPYYCGIGAEKS
              Consensus    (326)                                                                 GPYYCGVGADKA
```

FIG. 1F

```
SEQ ID NO 02 (AT1G48470)  (167) FGRDIVDAHYKACLYSGLSIGGANGEVMPGQWEFQISPTVG----------IGAGDQLWVARYILE
SEQ ID NO 06 (AT3G17820)  (167) IGRDIVDAHYKACLYAGIGISGINGEVMPGQWEFQVGPVEG----------ISSGDQVWVARYILE
SEQ ID NO 34 (Os03g50490) (169) YGRDIVDAHYKACLFAGINISGINAEVMPGQWEFQVGPVVG----------VSAGDHVWVARYILE
SEQ ID NO 46 (ZmGS1-2)    (166) YGRDIVDCAYKACLYACLYAGIDISGINGEVMPGQWEFQVAPAVG---------VSAGDQLWVARYILE
SEQ ID NO 04 (AT1G66200)  (167) FGRDIVDAHYKASLYAGINISGINGEVMPGQWEFQVGPAVG----------ISAADEIWIARYILE
SEQ ID NO 12 (AT5G37600)  (167) FGRDVVDSHYKACLYAGINISGINGEVMPGQWEFQVGPAVG----------ISAADEIWVARYILE
SEQ ID NO 08 (AT5G16570)  (167) FGRDISHYKACLYAGINVSGTNGEVMPGQWEFQVGPTVG----------IAAADQVWVARYILE
SEQ ID NO 10 (AT5G35630)  (225) WGRDISDAHYKACLYAGINISGTNGEVMPGQWEFQVGPSVG----------IDAGDHVWCARYLLE
SEQ ID NO 18 (Gm0030x00147) (227) FGRDISDAHYKACLYAGINISGTNGEVMPGQWEYQVGPSVG----------IEAGDHIWASRYILE
SEQ ID NO 28 (Gm0271x00039) (227) FGRDISDAHYKACLYAGINISGTNGEVMPGQWEYQVGPSVG----------IEAGDHIWASRYILE
SEQ ID NO 36 (Os04g56400) (223) FGRDISDAHYKACLYAGINISGTNGEVMPGQWEYQVGPSVG----------IEAGDHIWISRYILE
SEQ ID NO 42 (Sb06g147820) (180) FGRDISDAHYKACLYAGINISGTNGEVMPGQWEFQVGPSVG----------IEAGDHIWISRYILE
SEQ ID NO 54 (ZmGS2)      (218) FGRDISDAHYKACIYAGINISGTNGEVMPGQWEFQVGPSVG----------IEAGDHIWISRYILE
SEQ ID NO 32 (Os03g12290) (167) FGRDIVDAHYKACLYAGINISGINGEVMPGQWEFQVGPSVG----------IAAADQVWVARYILE
SEQ ID NO 38 (Sb01g143820) (167) FGRDVVDAHYKACLYACLYAGINISGINGEVMPGQWEFQVGPSVG----------ISAGDEIWVARYILE
SEQ ID NO 44 (ZmGS1-1)    (167) FGRDVVDAHYKACLYAGINISGINGEVMPGQWEFQVGPSVG----------ISAGDEIWVARYILE
SEQ ID NO 52 (ZmGS1-5)    (167) FGRDVVDAHYKACLYAGINISGINGEVMPGQWEFQVGPSVG----------ISAGDEIWVARYILE
SEQ ID NO 14 (Gm0005x00111) (167) YGRDIVDAHYKACIYAGINISGINGEVMPGQWEFQVGPSVG----------ISAGDEVWAARYILE
SEQ ID NO 26 (Gm0232x00015) (167) YGRDIVDAHYKACIYAGINISGINGEVMPGQWEFQVGPSVG----------ISAGDEVWAARYILE
SEQ ID NO 22 (Gm0081x00134) (167) FGRDIVDAHYKACIYAGINISGINGEVMPGQWEFQVGPSVG----------ISAGDEIWAARYILE
SEQ ID NO 24 (Gm0136x00208) (167) FGRDIVDAHYKACLYACIYAGINISGINGEVMPGQWEFQVGPSVG----------ISAGDEVWAARYILE
SEQ ID NO 16 (Gm0015x00387) (167) FGRDIVDAHYKACLYAGINISGINGEVMPGQWEFQVGPSVG----------ISAADELWVARYILE
SEQ ID NO 20 (Gm0040x00114) (308) FGRDIVDSHFKACLYAGINITGINAEVMPGQWEFRVGPSLASLRVTTCGLLATFWRLLAHDYSHH
SEQ ID NO 30 (Os02g50240) (167) FGRDIVDSHYKACLYAGINISGINGEVMPGQWEFQVGPSVG----------ISSGDQVWVARYILE
SEQ ID NO 40 (Sb04g133790) (166) FGRDIVDAHYKACIYAGINISGINGEVMPGQWEFQVGPSVG----------ISSGDQVWVARYILE
SEQ ID NO 48 (ZmGS1-3)    (167) FGRDIVDAHYKACLYAGINISGINGEVMPGQWEFQVGPSVG----------ISSGDQVWVARYILE
SEQ ID NO 50 (ZmGS1-4)    (167) FGRDIVDAHYKACLYAGINISGINGEVMPGQWEFQVGPSVG----------ISSGDQVWVARYILE
                Consensus (391) FGRDIVDAHYKACLYAGINISGINGEVMPGQWEFQVGPSVG          ISAGD VWVARYILE
```

FIG. 1G

| | | |
|---|---|---|
| SEQ ID NO 02 (AT1G48470) | (223) | RIT------------EICGVIVSFDPKPIQGDWNGAAAHTNFSTKSMRKDGGLDLIKE |
| SEQ ID NO 06 (AT3G17820) | (223) | RIT------------EISGVIVSFDPKPVPGDWNGAGAHCNYSTKTMRNDGGLEVIKK |
| SEQ ID NO 34 (Os03g50490) | (225) | RIT------------EIAGVVVSFDPKPIPGDWNGAGAHTNYSTKSMRSNGGYEVIKK |
| SEQ ID NO 46 (ZmGS1-2) | (222) | RIT------------EIAGVVVSFDPKPIPGDWNGAGAHTNYSTKSMRSDGGYEVIKK |
| SEQ ID NO 04 (AT1G66200) | (223) | RIT------------EIAGVVVSFDPKPIPGDWNGAGAHCNYSTKSMREEGGYEIIKK |
| SEQ ID NO 12 (AT5G37600) | (223) | RIT------------EIAGVVVSFDPKPIPGDWNGAGAHCNYSTKSMREEGGYEVIKK |
| SEQ ID NO 08 (AT5G16570) | (223) | RIT------------ELAGVVLSLDPKPIPGDWNGAGAHTNYSTKSMREDGGYEVIKK |
| SEQ ID NO 10 (AT5G35630) | (281) | RIT------------EQAGVVLTLDPKPIEGDWNGAGCHTNYSTKSMREGGFEVIKK |
| SEQ ID NO 18 (Gm0030x00147) | (283) | RIT------------EQAGVVLSLDPKPIEGDWNGAGCHTNYSTKSMREDGGFEVIKK |
| SEQ ID NO 28 (Gm0271x00039) | (283) | RIT------------EQAGVVLSLDPKPIEGDWNGAGCHTNYSTKSMREDGGFEVIKK |
| SEQ ID NO 36 (Os04g56400) | (279) | RIT------------EQAGVVLTLDPKPIQGDWNGAGCHTNYSTKSMREDGGFEVIKK |
| SEQ ID NO 42 (Sb06g147820) | (236) | RIT------------EQAGVVLTLDPKPIQGDWNGAGCHTNYSTKTMREDGGFEDIKR |
| SEQ ID NO 54 (ZmGS2) | (274) | RIT------------EQAGVVLTLDPKPIQGDWNGAGCHTNYSTKTMREDGGFEEIKR |
| SEQ ID NO 32 (Os03g12290) | (223) | RVT------------EVAGVVLSLDPKPIPGDWNGAGAHTNFSTKSMREPGGYEVIKK |
| SEQ ID NO 38 (Sb01g143820) | (223) | RIT------------EIAGIVLSLDPKPIQGDWNGAGAHTNYSTKSMREAGGYEVIKK |
| SEQ ID NO 44 (ZmGS1-1) | (223) | RIT------------EMAGIVLSLDPKPIKGDWNGAGAHTNYSTKSMREAGGYEVIKA |
| SEQ ID NO 52 (ZmGS1-5) | (223) | RIT------------EMAGIVLSLDPKPIKGDWNGAGAHTNYSTKSMREAGGYEVIKE |
| SEQ ID NO 14 (Gm0005x00111) | (223) | RIT------------EMAGVIVSFDPKPIPGDWNGAGAHSNYSTKSMREEGGYEVIKK |
| SEQ ID NO 26 (Gm0232x00015) | (223) | RIT------------EIAGAIVSFDPKPIPGDWNGAGAHSNYSTKSMREEGGYEVIKK |
| SEQ ID NO 22 (Gm0081x00134) | (223) | RIT------------EIAGVVVSFDPKPIPGDWNGAGAHTNYSTKSMREDGGYEVIKA |
| SEQ ID NO 24 (Gm0136x00208) | (223) | RIT------------EIAGVVVSFDPKPIQGDWNGAGAHTNYSTKSMRNDGGYEVIKT |
| SEQ ID NO 16 (Gm0015x00387) | (223) | RIT------------EIAGVVLSFDPKPIQGDWNGAGAHTNYSTKLMRNDGGYEIIKK |
| SEQ ID NO 20 (Gm0040x00114) | (373) | QILSFVNIAANISVCANISVCANISVVVLSFYPQPIKGDWNCASAHTNYSTKSMRNDGGYEVIRK |
| SEQ ID NO 30 (Os02g50240) | (223) | RIT------------EIAGVVVSFDPKPIPGDWNGAGAHTNYSTKSMRNDGGYEIIKS |
| SEQ ID NO 40 (Sb04g133790) | (222) | RIT------------EIAGVVLTFDPKPIPGDWNGAGAHTNYSTKSMRNEGGYEVIKA |
| SEQ ID NO 48 (ZmGS1-3) | (223) | RIT------------EIAGVVVTFDPKPIPGDWNGAGAHTNYSTE SMRKEGGYEVIKA |
| SEQ ID NO 50 (ZmGS1-4) | (223) | RIT------------EIAGVVVTFDPKPIPGDWNGAGAHTNYSTE SMRKEGGYEVIKK |
| Consensus | (456) | RIT             EIAGVVLSFDPKPI  GDWNGAGAHTNYSTKSMREDGGYEVIKK |

| | | 586 | 625 |
|---|---|---|---|
| SEQ ID NO 02 | (AT1G48470) | (334) | PSSNMDPYLVTSMIAETTIL--------------------------- |
| SEQ ID NO 06 | (AT3G17820) | (334) | PASNMDPYLVVTSMIAETTILG------------------------- |
| SEQ ID NO 34 | (Os03g50490) | (336) | PASNMDPYLVTAMIAETTILWEPSHGHGHGQSNGK------------ |
| SEQ ID NO 46 | (ZmGS1-2) | (333) | PASNMDPYVVTCLIAETTMLWEPSHSNGDGKGAAAP----------- |
| SEQ ID NO 04 | (AT1G66200) | (334) | PASNMDPYVVTSMIAETTILWNP------------------------ |
| SEQ ID NO 12 | (AT5G37600) | (334) | PASNMDPYIVTSMIAETTILWNP------------------------ |
| SEQ ID NO 08 | (AT5G16570) | (334) | PASNMDPYTVTSMIAESTILWKP------------------------ |
| SEQ ID NO 10 | (AT5G35630) | (392) | PASNMDPYIVTSLLAETTLLWEPTLEAEALAAQKLSLNV-------- |
| SEQ ID NO 18 | (Gm0030x00147) | (394) | PASNMDPYVVTSLLAETTLLWEPTLEAEALAAQKLALKV-------- |
| SEQ ID NO 28 | (Gm0271x000039) | (394) | PASNMDPYVVTSLLAETTLLWEPTLEAEALAAQKLALKV-------- |
| SEQ ID NO 36 | (Os04g56400) | (390) | PASNMDPYVVTALLAETTILWEPTLEAEVLAAKKLALKV-------- |
| SEQ ID NO 42 | (Sb06g147820) | (347) | PASNMDPYIVTGLLAETTILWQPTLEAEVLAAKKLALKV-------- |
| SEQ ID NO 54 | (ZmGS2) | (385) | PASNMDPYIVTGLLAETTILWQPSLEAEALAAKKLALKV-------- |
| SEQ ID NO 32 | (Os03g12290) | (334) | PASNMDPYVVTGMIAETTILWKQN----------------------- |
| SEQ ID NO 38 | (Sb01g143820) | (334) | PASNMDPYVVTGMIAETTILWNGN----------------------- |
| SEQ ID NO 44 | (ZmGS1-1) | (334) | PASNMDPYVVTGMIADTTILWKGN----------------------- |
| SEQ ID NO 52 | (ZmGS1-5) | (334) | PASNMDPYVVTGMIADTTILWKP------------------------ |
| SEQ ID NO 14 | (Gm0005x00111) | (334) | PASNMDPYVVTSMIAETTILWKP------------------------ |
| SEQ ID NO 26 | (Gm0232x000015) | (334) | PASNMDPYVVTSMIADTTILWKP------------------------ |
| SEQ ID NO 22 | (Gm0081x000134) | (334) | PASNMDPYVVTSMIADTTILWKP------------------------ |
| SEQ ID NO 24 | (Gm0136x00208) | (334) | PASNMDPYVVTSMIADTTILWKP------------------------ |
| SEQ ID NO 16 | (Gm0015x003087) | (334) | PASNMDPYVVTSMIAETTILWKP------------------------ |
| SEQ ID NO 20 | (Gm0040x001114) | (476) | ----------------------------------------------- |
| SEQ ID NO 30 | (Os02g50240) | (334) | PASNMDPYVVTSMIAETTIIWKP------------------------ |
| SEQ ID NO 40 | (Sb04g133790) | (333) | PASNMDPYVVTSMIAETTILWKP------------------------ |
| SEQ ID NO 48 | (ZmGS1-3) | (334) | PASNMDPYVVTSMIAETTILWKP------------------------ |
| SEQ ID NO 50 | (ZmGS1-4) | (333) | PASNMDPYVVTSMIAETTIVWKP------------------------ |
| Consensus | | (586) | PASNMDPYVVTSMIAETTILW P |

FIG. 1J

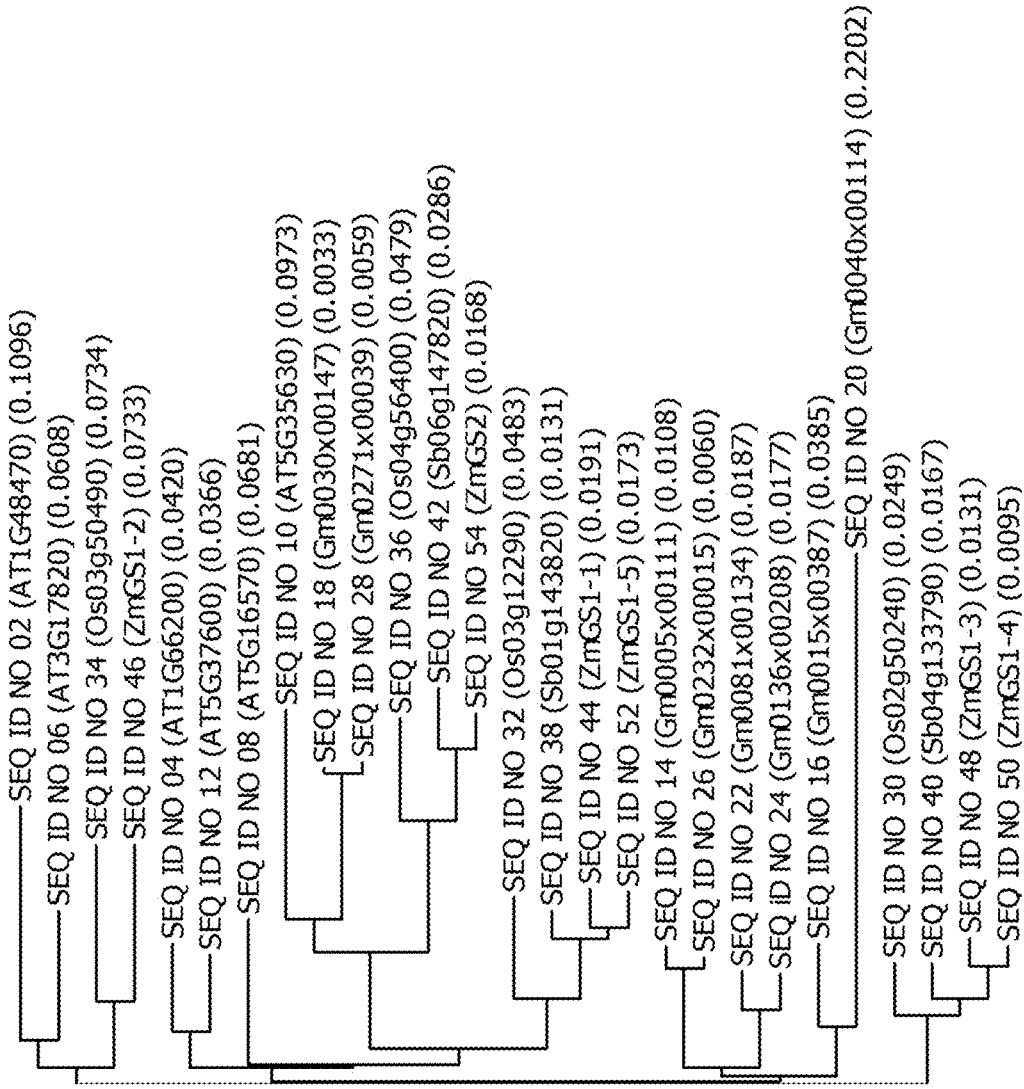

SEQUENCE LISTING

```
<160> NUMBER OF SEQ ID NOS: 54

<210> SEQ ID NO 1
<211> LENGTH: 1307
<212> TYPE: DNA
<213> ORGANISM: Arabidopsis thaliana

<400> SEQUENCE: 1
ataaaaatag tgagagtgac tgagatcaat agaaccaatc tcagaatcat cttctttctc      60
tttcggaaca aaaatgacgt ctcctctctc agatctccta aaccttgatc tatcagacac     120
caagaaaatc atcgctgaat acatatggat cggtggctct ggaatggata ttagaagcaa     180
agccaggaca ttaccaggac cagtaagtaa tccaacaaag cttccaaaat ggaactacga     240
tggatctagc accgatcaag ctgccggaga tgatagtgaa gtcattcttt atcctcaggc     300
aatatttaag gacccattca ggaaggggaa caacattctg gtgatgtgtg atgcttacag     360
accggccgga gatccaattc cgaccaacaa taggcacaag gccgtaaaaa tcttcgatca     420
```

-continued

```
tcccaatgtg aaggctgaag agccttggtt tgggatagag caagaataca cattacttaa      480
aaaagatgtg aagtggccac taggttggcc tcttggtggc tttcctggtc ctcagggacc      540
gtactattgt gcagtaggtg cagacaaagc ttttggtcgt gacattgtcg atgctcacta      600
taaagcttgt ctatactccg gtttgagtat tggtggtgcc aatggtgaag tcatgcctgg      660
acaatgggag tttcaaatca gtcctactgt tggtattggt gcaggtgatc aattatgggt      720
tgctcgttac attcttgaga ggattactga gatatgcggt gtgattgtct cattcgatcc      780
aaaaccaatc cagggtgatt ggaatggagc agccgctcat acgaacttca gtacaaaatc      840
gatgaggaaa gatggaggac tggatttgat taaggaagca ataaagaagc ttgaagtgaa      900
acacaaacaa cacattgctg cttatggtga aggcaacgag aggcgtctca ctgggaagca      960
tgaaactgca gacatcaaca ctttctcttg gggagtggcg gatcgtggag catcggtgag     1020
agtaggaaga gatacggaga aagaaggtaa agggtatttt gaagatcgaa ggccttcgtc     1080
taatatggat ccttacctag ttacctccat gattgctgaa accaccatcc tctaagcttt     1140
agactttcct tcgttttggt tctttgtatg ttcttcgaat ttcggtttga tatggtttaa     1200
tttcgcattt agactttcct ttcaaataag ttacgaaatg ttatgtgatt tctattgttt     1260
gatccggtta cggttcactt ttaagccaaa aaatctaccg ttatgac                   1307
```

<210> SEQ ID NO 2
<211> LENGTH: 353
<212> TYPE: PRT
<213> ORGANISM: Arabidopsis thaliana

<400> SEQUENCE: 2

```
Met Thr Ser Pro Leu Ser Asp Leu Leu Asn Leu Asp Leu Ser Asp Thr
1               5                   10                  15

Lys Lys Ile Ile Ala Glu Tyr Ile Trp Ile Gly Gly Ser Gly Met Asp
            20                  25                  30

Ile Arg Ser Lys Ala Arg Thr Leu Pro Gly Pro Val Ser Asn Pro Thr
        35                  40                  45

Lys Leu Pro Lys Trp Asn Tyr Asp Gly Ser Ser Thr Asp Gln Ala Ala
    50                  55                  60

Gly Asp Asp Ser Glu Val Ile Leu Tyr Pro Gln Ala Ile Phe Lys Asp
65                  70                  75                  80

Pro Phe Arg Lys Gly Asn Asn Ile Leu Val Met Cys Asp Ala Tyr Arg
                85                  90                  95

Pro Ala Gly Asp Pro Ile Pro Thr Asn Asn Arg His Lys Ala Val Lys
            100                 105                 110

Ile Phe Asp His Pro Asn Val Lys Ala Glu Glu Pro Trp Phe Gly Ile
        115                 120                 125

Glu Gln Glu Tyr Thr Leu Leu Lys Lys Asp Val Lys Trp Pro Leu Gly
    130                 135                 140

Trp Pro Leu Gly Gly Phe Pro Gly Pro Gln Gly Pro Tyr Tyr Cys Ala
145                 150                 155                 160

Val Gly Ala Asp Lys Ala Phe Gly Arg Asp Ile Val Asp Ala His Tyr
                165                 170                 175

Lys Ala Cys Leu Tyr Ser Gly Leu Ser Ile Gly Ala Asn Gly Glu
            180                 185                 190

Val Met Pro Gly Gln Trp Glu Phe Gln Ile Ser Pro Thr Val Gly Ile
        195                 200                 205

Gly Ala Gly Asp Gln Leu Trp Val Ala Arg Tyr Ile Leu Glu Arg Ile
    210                 215                 220
```

```
Thr Glu Ile Cys Gly Val Ile Val Ser Phe Asp Pro Lys Pro Ile Gln
225                 230                 235                 240

Gly Asp Trp Asn Gly Ala Ala Ala His Thr Asn Phe Ser Thr Lys Ser
            245                 250                 255

Met Arg Lys Asp Gly Gly Leu Asp Leu Ile Lys Glu Ala Ile Lys Lys
        260                 265                 270

Leu Glu Val Lys His Lys Gln His Ile Ala Ala Tyr Gly Glu Gly Asn
    275                 280                 285

Glu Arg Arg Leu Thr Gly Lys His Glu Thr Ala Asp Ile Asn Thr Phe
290                 295                 300

Ser Trp Gly Val Ala Asp Arg Gly Ala Ser Val Arg Val Gly Arg Asp
305                 310                 315                 320

Thr Glu Lys Glu Gly Lys Gly Tyr Phe Glu Asp Arg Arg Pro Ser Ser
            325                 330                 335

Asn Met Asp Pro Tyr Leu Val Thr Ser Met Ile Ala Glu Thr Thr Ile
            340                 345                 350

Leu
```

<210> SEQ ID NO 3
<211> LENGTH: 1499
<212> TYPE: DNA
<213> ORGANISM: Arabidopsis thaliana

<400> SEQUENCE: 3

```
gtactaccac aaccacgaac tctaaagcat catctcatta acaaaaataa aacacacaat      60
ctcaagattt tctacttctt attacaaaga ttcaatcttc ttgtttcttc ttgcaaccat     120
gagtcttctt gcagatcttg ttaaccttga catctcagac aacagtgaaa agatcatcgc     180
tgaatacata tgggttggtg gttctggtat ggacatgaga agcaaagcca ggactctccc     240
tggacctgtg accgatccat caaaacttcc aaagtggaac tatgatggtt caagcactgg     300
tcaagctcct ggtcaagaca gtgaagtgat cttataccct caagcaattt tcaaagatcc     360
attccgtaga ggcaacaaca tccttgttat gtgtgatgct acactccag cgggagagcc      420
aatccctact aacaagcgac atgctgcggc tgagatcttt gctaaccctg atgttattgc     480
tgaagtgcca tggtatggaa tcgaacaaga atacactttg ttgcagaagg atgtgaactg     540
gcctcttgga tggcccattg gtggcttccc tggccctcag ggaccatact actgcagtat     600
tggagctgac aaatcttttg aagagacat tgttgatgct cactacaaag cctctttgta      660
tgctggaatc aacatcagtg ggatcaatgg agaagtcatg ccgggacaat gggagttcca     720
agtcggccca tcggtcggta tctcagctgc tgatgaaata tggatcgctc gttacatttt     780
ggagaggatc acagagattg ctggtgtggt tgtatctttt gacccaaaac ctattcctgg     840
tgactggaat ggagctggtg ctcacaccaa ttacagtact aaatcaatga gggaagaagg     900
aggatacgag ataatcaaga aggcgatcga aagcttggc ttgagacaca aggaacacat      960
ttccgcttac ggtgaaggaa acgagcgtcg tctcacggga caccatgaaa ctgctgacat    1020
caacactttc ctttggggtg ttgcgaaccg tggtgcatcg atccgagtag acgtgacac     1080
cgagaaagaa gggaagggat actttgagga taggaggcca gcttcaaaca tggacccta    1140
cgttgttact tccatgattg cagagactac actcctctgg aacccttgaa aggatgatcc    1200
gtaactcttg aagttgcttc tgattgggtt tttggaagt tccaagcttg tcttttctct     1260
acagtgtgta ttaagcaatt gtaccggttg acactgccgg agtttgtgat ttggggcctt    1320
```

```
tcttctttt tcttcttttt ataatcttt gggttctgtg gttagagcaa attcggtttg      1380
ctctgtttgt ttgaccttta ttgaaacctt tggtattggt actaataata caatctgaaa      1440
aggcctcttc atgtttcaat gttagagact aattaaagat ctcttttatt tttcatttt      1499
```

<210> SEQ ID NO 4
<211> LENGTH: 356
<212> TYPE: PRT
<213> ORGANISM: Arabidopsis thaliana

<400> SEQUENCE: 4

```
Met Ser Leu Leu Ala Asp Leu Val Asn Leu Asp Ile Ser Asp Asn Ser
1               5                   10                  15

Glu Lys Ile Ile Ala Glu Tyr Ile Trp Val Gly Gly Ser Gly Met Asp
            20                  25                  30

Met Arg Ser Lys Ala Arg Thr Leu Pro Gly Pro Val Thr Asp Pro Ser
        35                  40                  45

Lys Leu Pro Lys Trp Asn Tyr Asp Gly Ser Ser Thr Gly Gln Ala Pro
    50                  55                  60

Gly Gln Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Ala Tyr Thr
                85                  90                  95

Pro Ala Gly Glu Pro Ile Pro Thr Asn Lys Arg His Ala Ala Ala Glu
            100                 105                 110

Ile Phe Ala Asn Pro Asp Val Ile Ala Glu Val Pro Trp Tyr Gly Ile
        115                 120                 125

Glu Gln Glu Tyr Thr Leu Leu Gln Lys Asp Val Asn Trp Pro Leu Gly
    130                 135                 140

Trp Pro Ile Gly Gly Phe Pro Gly Pro Gln Gly Pro Tyr Tyr Cys Ser
145                 150                 155                 160

Ile Gly Ala Asp Lys Ser Phe Gly Arg Asp Ile Val Asp Ala His Tyr
                165                 170                 175

Lys Ala Ser Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ala Ala Asp Glu Ile Trp Ile Ala Arg Tyr Ile Leu Glu Arg Ile
    210                 215                 220

Thr Glu Ile Ala Gly Val Val Val Ser Phe Asp Pro Lys Pro Ile Pro
225                 230                 235                 240

Gly Asp Trp Asn Gly Ala Gly Ala His Thr Asn Tyr Ser Thr Lys Ser
                245                 250                 255

Met Arg Glu Glu Gly Gly Tyr Glu Ile Ile Lys Lys Ala Ile Glu Lys
            260                 265                 270

Leu Gly Leu Arg His Lys Glu His Ile Ser Ala Tyr Gly Glu Gly Asn
        275                 280                 285

Glu Arg Arg Leu Thr Gly His His Glu Thr Ala Asp Ile Asn Thr Phe
    290                 295                 300

Leu Trp Gly Val Ala Asn Arg Gly Ala Ser Ile Arg Val Gly Arg Asp
305                 310                 315                 320

Thr Glu Lys Glu Gly Lys Gly Tyr Phe Glu Asp Arg Arg Pro Ala Ser
                325                 330                 335

Asn Met Asp Pro Tyr Val Val Thr Ser Met Ile Ala Glu Thr Thr Leu
            340                 345                 350
```

Leu Trp Asn Pro
        355

<210> SEQ ID NO 5
<211> LENGTH: 1341
<212> TYPE: DNA
<213> ORGANISM: Arabidopsis thaliana

<400> SEQUENCE: 5

| | | | | | |
|---|---|---|---|---|---|
| ctctataaac | acacactctc | aggagagaag | ttgtattgat | cgtcttctct | ttccctaaac | 60 |
| acactgatta | ttttctctcc | gacgccgcca | tgtctctgct | ctcagatctc | gttaacctca | 120 |
| acctcaccga | tgccaccggg | aaaatcatcg | ccgaatacat | atggatcggt | ggatctggaa | 180 |
| tggatatcag | aagcaaagcc | aggacactac | caggaccagt | gactgatcca | tcaaagcttc | 240 |
| ccaagtggaa | ctacgacgga | tccagcaccg | gtcaggctgc | tggagaagac | agtgaagtca | 300 |
| ttctataccc | tcaggcaata | ttcaaggatc | ccttcaggaa | aggcaacaac | atcctggtga | 360 |
| tgtgtgatgc | ttacacacca | gctggtgatc | ctattccaac | caacaagagg | cacaacgctg | 420 |
| ctaagatctt | cagccacccc | gacgttgcca | aggaggagcc | ttggtatggg | attgagcaag | 480 |
| aatacacttt | gatgcaaaag | gatgtgaact | ggccaattgg | ttggcctgtt | ggtggctacc | 540 |
| ctggcccctca | gggaccttac | tactgtggtg | tgggagctga | caaagccatt | ggtcgtgaca | 600 |
| ttgtggatgc | tcactacaag | gcctgtcttt | acgccggtat | tggtatttct | ggtatcaatg | 660 |
| gagaagtcat | gccaggccag | tgggagttcc | aagtcggccc | tgttgagggt | attagttctg | 720 |
| gtgatcaagt | ctgggttgct | cgatacccttc | tcgagaggat | cactgagatc | tctggtgtaa | 780 |
| ttgtcagctt | cgacccgaaa | ccagtcccgg | gtgactggaa | tggagctgga | gctcactgca | 840 |
| actacagcac | taagacaatg | agaaacgatg | gaggattaga | agtgatcaag | aaagcgatag | 900 |
| ggaagcttca | gctgaaacac | aaagaacaca | ttgctgctta | cggtgaagga | acgagcgtc | 960 |
| gtctcactgg | aaagcacgaa | accgcagaca | tcaacacatt | ctcttgggga | gtcgcgaacc | 1020 |
| gtggagcgtc | agtgagagtg | ggacgtgaca | cagagaagga | aggtaaaggg | tacttcgaag | 1080 |
| acagaaggcc | agcttctaac | atggatcctt | acgttgtcac | ctccatgatc | gctgagacga | 1140 |
| ccatactcgg | ttgatgacac | atttcatgat | ttgatttctc | tccaatttgg | tttttttttt | 1200 |
| ttcccttttg | attgcacttt | tcgataataa | aaaaataatt | cttattatgg | gcgtattgtt | 1260 |
| gtgacatttt | gtgttttgtt | tcgaataatt | aaataagcgc | ttcttaaggt | gaaaataaat | 1320 |
| aataattagt | gatttttaat | c | | | 1341 |

<210> SEQ ID NO 6
<211> LENGTH: 354
<212> TYPE: PRT
<213> ORGANISM: Arabidopsis thaliana

<400> SEQUENCE: 6

Met Ser Leu Leu Ser Asp Leu Val Asn Leu Asn Leu Thr Asp Ala Thr
1               5                   10                  15

Gly Lys Ile Ile Ala Glu Tyr Ile Trp Ile Gly Gly Ser Gly Met Asp
            20                  25                  30

Ile Arg Ser Lys Ala Arg Thr Leu Pro Gly Pro Val Thr Asp Pro Ser
        35                  40                  45

Lys Leu Pro Lys Trp Asn Tyr Asp Gly Ser Ser Thr Gly Gln Ala Ala
    50                  55                  60

Gly Glu Asp Ser Glu Val Ile Leu Tyr Pro Gln Ala Ile Phe Lys Asp 65                  70                  75                  80
    Pro Phe Arg Lys Gly Asn Asn Ile Leu Val Met Cys Asp Ala Tyr Thr
                    85                  90                  95

Pro Ala Gly Asp Pro Ile Pro Thr Asn Lys Arg His Asn Ala Ala Lys
                100                 105                 110

Ile Phe Ser His Pro Asp Val Ala Lys Glu Glu Pro Trp Tyr Gly Ile
            115                 120                 125

Glu Gln Glu Tyr Thr Leu Met Gln Lys Asp Val Asn Trp Pro Ile Gly
        130                 135                 140

Trp Pro Val Gly Gly Tyr Pro Gly Pro Gln Gly Pro Tyr Tyr Cys Gly
    145                 150                 155                 160

Val Gly Ala Asp Lys Ala Ile Gly Arg Asp Ile Val Asp Ala His Tyr
                    165                 170                 175

Lys Ala Cys Leu Tyr Ala Gly Ile Gly Ile Ser Gly Ile Asn Gly Glu
                180                 185                 190

Val Met Pro Gly Gln Trp Glu Phe Gln Val Gly Pro Val Glu Gly Ile
            195                 200                 205

Ser Ser Gly Asp Gln Val Trp Val Ala Arg Tyr Leu Leu Glu Arg Ile
        210                 215                 220

Thr Glu Ile Ser Gly Val Ile Val Ser Phe Asp Pro Lys Pro Val Pro
    225                 230                 235                 240

Gly Asp Trp Asn Gly Ala Gly Ala His Cys Asn Tyr Ser Thr Lys Thr
                    245                 250                 255

Met Arg Asn Asp Gly Gly Leu Glu Val Ile Lys Lys Ala Ile Gly Lys
                260                 265                 270

Leu Gln Leu Lys His Lys Glu His Ile Ala Ala Tyr Gly Glu Gly Asn
            275                 280                 285

Glu Arg Arg Leu Thr Gly Lys His Glu Thr Ala Asp Ile Asn Thr Phe
        290                 295                 300

Ser Trp Gly Val Ala Asn Arg Gly Ala Ser Val Arg Val Gly Arg Asp
    305                 310                 315                 320

Thr Glu Lys Glu Gly Lys Gly Tyr Phe Glu Asp Arg Arg Pro Ala Ser
                    325                 330                 335

Asn Met Asp Pro Tyr Val Val Thr Ser Met Ile Ala Glu Thr Thr Ile
                340                 345                 350

Leu Gly

<210> SEQ ID NO 7
    <211> LENGTH: 1269
    <212> TYPE: DNA
    <213> ORGANISM: Arabidopsis thaliana

<400> SEQUENCE: 7
accaaaaaaa aaaaggttta ttattctttg agattcctaa gatatgtctt cacttgcaga      60
tttaatcaat ctcgatctct ccgattccac tgaccagatc atcgccgagt acatatggat     120
tggtggatcg ggcttggata tgagaagcaa agcaaggact ttgcctggac cagtgacgga     180
tccatcgcag ttaccgaaat ggaactacga cggttcaagc accggccaag ctccgggcga     240
tgacagtgaa gtcatcatct accctcaagc tatcttcaaa gaccccttca gaagaggcaa     300
caacatcctt gtgatgtgtg acgcatatac accggcagga gagccgattc gacgaacaa      360 aaggcatgcg gcggctaaga tctttgaaga ccctagtgtt gtcgccgaag aaacatggta     420
cggaattgaa caagagtata ccttgttgca aaaggatatt aagtggccgg taggttggcc     480

```
ggtcggcggt tcccaggtc ctcagggacc gtactactgt ggagttggag cagacaaagc      540
ctttggaaga gacatcgttg attctcatta caaagcttgt ctttacgccg aatcaatgt      600
cagtgggact aacggcgaag ttatgcctgg ccagtgggag ttccaagtcg gtcccaccgt     660
tggaatcgct gccgccgatc aggtctgggt tgctcgttac attcttgaga ggatcacaga    720
attggctgga gttgttctgt ctctagaccc taaaccaatt ccgggagatt ggaatggtgc    780
aggggcacac acaaattaca gtacgaagtc gatgagagaa gatggagggt acgaggtgat    840
aaagaaagca atagagaagc ttggattgcg tcacaaggaa cacattgctg cttatggtga    900
aggcaacgag cgtcgtctca ccggaaaaca tgaaaccgcc gatatcaaca ctttcttatg    960
gggtgtggca aaccgtgggg catcgattag ggttgggcgt gacactgagc aggctggaaa    1020
aggatacttt gaagatcgta ggccagcttc gaacatggat ccttacactg tgacctccat    1080
gattgctgaa tccacaatcc tttggaaacc atgaagaag aaaccttgag cctcaaggaa     1140
tctctataat atcagttcat gttcattctt ctatggtctc tttctcattc tgaaacagtt    1200
ctcatgtgtt ctttgtttat tatgtttgat ttgaagtctt caatttgttt ctgagaacga    1260
tagttcctc                                                              1269

<210> SEQ ID NO 8
<211> LENGTH: 356
<212> TYPE: PRT
<213> ORGANISM: Arabidopsis thaliana

<400> SEQUENCE: 8

Met Ser Ser Leu Ala Asp Leu Ile Asn Leu Asp Leu Ser Asp Ser Thr
1               5                   10                  15

Asp Gln Ile Ile Ala Glu Tyr Ile Trp Ile Gly Gly Ser Gly Leu Asp
            20                  25                  30

Met Arg Ser Lys Ala Arg Thr Leu Pro Gly Pro Val Thr Asp Pro Ser
        35                  40                  45

Gln Leu Pro Lys Trp Asn Tyr Asp Gly Ser Ser Thr Gly Gln Ala Pro
    50                  55                  60

Gly Asp Asp Ser Glu Val Ile Ile Tyr Pro Gln Ala Ile Phe Lys Asp
65                  70                  75                  80

Pro Phe Arg Arg Gly Asn Asn Ile Leu Val Met Cys Asp Ala Tyr Thr
                85                  90                  95

Pro Ala Gly Glu Pro Ile Pro Thr Asn Lys Arg His Ala Ala Ala Lys
            100                 105                 110

Ile Phe Glu Asp Pro Ser Val Val Ala Glu Glu Thr Trp Tyr Gly Ile
        115                 120                 125

Glu Gln Glu Tyr Thr Leu Leu Gln Lys Asp Ile Lys Trp Pro Val Gly
    130                 135                 140

Trp Pro Val Gly Gly Phe Pro Gly Pro Gln Gly Pro Tyr Tyr Cys Gly
145                 150                 155                 160

Val Gly Ala Asp Lys Ala Phe Gly Arg Asp Ile Val Asp Ser His Tyr
                165                 170                 175

Lys Ala Cys Leu Tyr Ala Gly Ile Asn Val Ser Gly Thr Asn Gly Glu
            180                 185                 190

Val Met Pro Gly Gln Trp Glu Phe Gln Val Gly Pro Thr Val Gly Ile
        195                 200                 205

Ala Ala Ala Asp Gln Val Trp Val Ala Arg Tyr Ile Leu Glu Arg Ile
    210                 215                 220

Thr Glu Leu Ala Gly Val Val Leu Ser Leu Asp Pro Lys Pro Ile Pro
```

```
                225                 230                 235                 240
Gly Asp Trp Asn Gly Ala Gly Ala His Thr Asn Tyr Ser Thr Lys Ser
                245                 250                 255

Met Arg Glu Asp Gly Gly Tyr Glu Val Ile Lys Lys Ala Ile Glu Lys
            260                 265                 270

Leu Gly Leu Arg His Lys Glu His Ile Ala Ala Tyr Gly Glu Gly Asn
        275                 280                 285

Glu Arg Arg Leu Thr Gly Lys His Glu Thr Ala Asp Ile Asn Thr Phe
    290                 295                 300

Leu Trp Gly Val Ala Asn Arg Gly Ala Ser Ile Arg Val Gly Arg Asp
305                 310                 315                 320

Thr Glu Gln Ala Gly Lys Gly Tyr Phe Glu Asp Arg Arg Pro Ala Ser
                325                 330                 335

Asn Met Asp Pro Tyr Thr Val Thr Ser Met Ile Ala Glu Ser Thr Ile
            340                 345                 350

Leu Trp Lys Pro
        355

<210> SEQ ID NO 9
<211> LENGTH: 1604
<212> TYPE: DNA
<213> ORGANISM: Arabidopsis thaliana

<400> SEQUENCE: 9
cttcttaatt gtttcctctt gtgttttgtt aacttttttt ctagcattct tgatctgttg      60
ttcttgtcac ttgttttgtt ttctgggatc atcaatccaa tggctcagat cttagcagct     120
tctccaacat gtcagatgag agtgcctaaa cactcatcag tcattgcatc atcatccaag     180
ttatggagct ctgttgtgtt gaaacagaag aagcagagca caacaaagt cagaggcttt      240
agagttcttg ctctccaatc tgataacagt actgtcaata gagttgagac tcttctcaat     300
ttagacacca aaccttactc tgacaggatc attgctgaat acatttggat cggaggatct     360
ggaattgacc ttagaagcaa gtcaaggact atcgaaaagc cggtggagga tccttctgag     420
ctacctaagt ggaactatga tggttcgagt accggtcaag cacctggtga agatagtgaa     480
gtgattctat acccgcaagc tatcttcaga gatccttttcc gtggaggcaa taacatcttg    540
gttatctgtg atacttggac caagctggt gagccaattc caacaaacaa acgtgctaaa      600
gctgctgaga tcttcagtaa caagaaggtc tctggcgagg ttccatggtt cggcattgaa     660
caagagtaca ctttacttca gcaaaacgtc aaatggcctt taggttggcc tgttggagcg     720
ttccctggtc ctcagggtcc ttactactgt ggagttggag ctgacaagat tgggggcgt      780
gacatttcag atgctcatta caaagcttgt ttatatgctg gaattaacat tagtggtact     840
aatggtgaag ttatgcctgg acagtgggag ttccaagttg gcccgagcgt aggaattgat     900
gcaggtgatc atgtttggtg tgctagatac cttcttgaga gaatcacaga caagctggt      960
gttgtcctaa cacttgatcc caaaccgata gagggtgact ggaacggtgc tggttgccac    1020
accaattaca gtaccaagag catgagagag gaaggaggat tgaagtgat caagaaggct    1080
atcttgaacc tctcgcttcg ccacaaggag cacatcagtg cctacggtga aggaaacgag    1140
agaaggttga ccggaaagca cgagacagct agtattgacc agttctcatg gggcgtggct    1200
aaccgtggat gctctattcg tgtgggacgt gacaccgagg cgaaaggaaa aggttactta    1260
gaagatcgcc gtccagcatc taacatggac ccatacattg tgacctcact tttggcagag    1320
accacactcc tgtgggagcc aactcttgag ctgaagccc ttgcagctca aaagctttct    1380
```

```
ttgaatgttt aaaattagtc gaaactttca tgaatctgat gaacacacgt gtctatgtgg    1440
tctctcaagt tgtttaaaca ttcggattaa gacattgttt gttgtctttt catttgcatt    1500
tttaaaactc agaattgtat ggacaatgtt catccttta tattggttct tttgactgtt    1560
agagcatgtc caatggttga atttaagctg gttcttaact gttg                     1604
```

<210> SEQ ID NO 10
<211> LENGTH: 430
<212> TYPE: PRT
<213> ORGANISM: Arabidopsis thaliana

<400> SEQUENCE: 10

```
Met Ala Gln Ile Leu Ala Ala Ser Pro Thr Cys Gln Met Arg Val Pro
1               5                   10                  15

Lys His Ser Ser Val Ile Ala Ser Ser Lys Leu Trp Ser Ser Val
            20                  25                  30

Val Leu Lys Gln Lys Lys Gln Ser Asn Asn Lys Val Arg Gly Phe Arg
        35                  40                  45

Val Leu Ala Leu Gln Ser Asp Asn Ser Thr Val Asn Arg Val Glu Thr
    50                  55                  60

Leu Leu Asn Leu Asp Thr Lys Pro Tyr Ser Asp Arg Ile Ile Ala Glu
65                  70                  75                  80

Tyr Ile Trp Ile Gly Gly Ser Gly Ile Asp Leu Arg Ser Lys Ser Arg
                85                  90                  95

Thr Ile Glu Lys Pro Val Glu Asp Pro Ser Glu Leu Pro Lys Trp Asn
            100                 105                 110

Tyr Asp Gly Ser Ser Thr Gly Gln Ala Pro Gly Glu Asp Ser Glu Val
        115                 120                 125

Ile Leu Tyr Pro Gln Ala Ile Phe Arg Asp Pro Phe Arg Gly Gly Asn
    130                 135                 140

Asn Ile Leu Val Ile Cys Asp Thr Trp Thr Pro Ala Gly Glu Pro Ile
145                 150                 155                 160

Pro Thr Asn Lys Arg Ala Lys Ala Ala Glu Ile Phe Ser Asn Lys Lys
                165                 170                 175

Val Ser Gly Glu Val Pro Trp Phe Gly Ile Glu Gln Glu Tyr Thr Leu
            180                 185                 190

Leu Gln Gln Asn Val Lys Trp Pro Leu Gly Trp Pro Val Gly Ala Phe
        195                 200                 205

Pro Gly Pro Gln Gly Pro Tyr Tyr Cys Gly Val Gly Ala Asp Lys Ile
    210                 215                 220

Trp Gly Arg Asp Ile Ser Asp Ala His Tyr Lys Ala Cys Leu Tyr Ala
225                 230                 235                 240

Gly Ile Asn Ile Ser Gly Thr Asn Gly Glu Val Met Pro Gly Gln Trp
                245                 250                 255

Glu Phe Gln Val Gly Pro Ser Val Gly Ile Asp Ala Gly Asp His Val
            260                 265                 270

Trp Cys Ala Arg Tyr Leu Leu Glu Arg Ile Thr Glu Gln Ala Gly Val
        275                 280                 285

Val Leu Thr Leu Asp Pro Lys Pro Ile Glu Gly Asp Trp Asn Gly Ala
    290                 295                 300

Gly Cys His Thr Asn Tyr Ser Thr Lys Ser Met Arg Glu Glu Gly Gly
305                 310                 315                 320

Phe Glu Val Ile Lys Lys Ala Ile Leu Asn Leu Ser Leu Arg His Lys
                325                 330                 335
```

```
Glu His Ile Ser Ala Tyr Gly Glu Gly Asn Glu Arg Arg Leu Thr Gly
            340                 345                 350

Lys His Glu Thr Ala Ser Ile Asp Gln Phe Ser Trp Gly Val Ala Asn
            355                 360                 365

Arg Gly Cys Ser Ile Arg Val Gly Arg Asp Thr Glu Ala Lys Gly Lys
        370                 375                 380

Gly Tyr Leu Glu Asp Arg Arg Pro Ala Ser Asn Met Asp Pro Tyr Ile
385                 390                 395                 400

Val Thr Ser Leu Leu Ala Glu Thr Thr Leu Leu Trp Glu Pro Thr Leu
                405                 410                 415

Glu Ala Glu Ala Leu Ala Ala Gln Lys Leu Ser Leu Asn Val
            420                 425                 430

<210> SEQ ID NO 11
<211> LENGTH: 1494
<212> TYPE: DNA
<213> ORGANISM: Arabidopsis thaliana

<400> SEQUENCE: 11
tgtggagagc caaaaagtct ccaaagtctt cacgtcaccc tcttcctcaa tctctgcacc      60 caccoctcct ccttctataa gtactactct tcatatctct ctctaccaaa atatcaaaac    120
acgagacaga tttgattcca ttttttattac tgttactatc atccaaaccc ttggtatttg    180
tagccatgag tcttgtttca gatctcatca accttaacct ctcagactcc actgacaaaa    240
tcattgctga atacatatgg gttggtggtt ctggaatgga catgagaagc aaagccagga    300
ctctacctgg accagtgact gacccttcgc agctaccaaa gtggaactat gatggttcaa    360
gcacaggcca agctcctggt gaagacagtg aagtcatctt ataccctcaa gccatattca    420
aggatccttt ccgtagagga acaacattc ttgtcatgtg cgatgcgtac actccgcgg      480 gtgaaccaat cccgactaac aaaagacacg ctgcggctaa ggtctttagc aaccctgatg    540
ttgcagctga agtgccatgg tatggtattg agcaagaata cactttactc cagaaagatg    600
tgaagtggcc tgttggttgg cctattggtg gttatcccgg ccctcaggga ccgtactatt    660
gcggtattgg agcagacaaa tcttttggca gagatgttgt tgattctcac tacaaggcct    720
gcttatacgc tgggatcaac attagtggca tcaatggaga agtcatgccg ggtcagtggg    780
agttccaggt cggtccagct gttggtatct cggctgctga tgaaatttgg gtcgctcgtt    840
acattttgga gaggatcaca gagattgctg gtgtagtggt atcttttgac ccgaaaccga    900
ttcccggtga ctggaacggt gctggtgctc actgcaacta cagtaccaag tcaatgaggg    960
aagaaggcgg ttacgagatc atcaagaaag caatcgataa attgggactg agacacaaag    1020
aacacattgc tgcttacggt gaaggcaatg agcgtcgtct cacaggacac acgagactg    1080 ctgacatcaa cactttcctt tggggtgttg cgaaccgtgg agcatcgatc cgagtaggac    1140
gtgatacgga gaagaaggg aaaggatact tgaggacag gaggccagct tcgaacatgg    1200
atccttacat tgtcacttcc atgattgcag agactacaat cctctggaat ccttgatgat    1260
catcagatca agaaaaaatc ttgaatgtca ctcaaatttg tgtttcttgc aagattcaaa    1320
gtttgtgttc tctatcaagc aatgtcttag gataagtcaa agatttgctc tgcttattct    1380 gcttttttatt tacttcacat cctattgaaa acatttctgt gtattattta tgaataaaca    1440
ttatcttaaa agggctgatt tatttactaa tgcatgcatt caccacttaa gatc           1494

<210> SEQ ID NO 12
```

```
<211> LENGTH: 356
<212> TYPE: PRT
<213> ORGANISM: Arabidopsis thaliana

<400> SEQUENCE: 12

Met Ser Leu Val Ser Asp Leu Ile Asn Leu Asn Leu Ser Asp Ser Thr
1               5                   10                  15

Asp Lys Ile Ile Ala Glu Tyr Ile Trp Val Gly Gly Ser Gly Met Asp
            20                  25                  30

Met Arg Ser Lys Ala Arg Thr Leu Pro Gly Pro Val Thr Asp Pro Ser
        35                  40                  45

Gln Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Ala Tyr Thr
                85                  90                  95

Pro Ala Gly Glu Pro Ile Pro Thr Asn Lys Arg His Ala Ala Ala Lys
            100                 105                 110

Val Phe Ser Asn Pro Asp Val Ala Ala Glu Val Pro Trp Tyr Gly Ile
        115                 120                 125

Glu Gln Glu Tyr Thr Leu Leu Gln Lys Asp Val Lys Trp Pro Val Gly
    130                 135                 140

Trp Pro Ile Gly Gly Tyr Pro Gly Pro Gln Gly Pro Tyr Tyr Cys Gly
145                 150                 155                 160

Ile Gly Ala Asp Lys Ser Phe Gly Arg Asp Val Val Asp Ser His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ala Val Gly Ile
        195                 200                 205

Ser Ala Ala Asp Glu Ile Trp Val Ala Arg Tyr Ile Leu Glu Arg Ile
    210                 215                 220

Thr Glu Ile Ala Gly Val Val Val Ser Phe Asp Pro Lys Pro Ile Pro
225                 230                 235                 240

Gly Asp Trp Asn Gly Ala Gly Ala His Cys Asn Tyr Ser Thr Lys Ser
                245                 250                 255

Met Arg Glu Glu Gly Gly Tyr Glu Ile Ile Lys Lys Ala Ile Asp Lys
            260                 265                 270

Leu Gly Leu Arg His Lys Glu His Ile Ala Ala Tyr Gly Glu Gly Asn
        275                 280                 285

Glu Arg Arg Leu Thr Gly His His Glu Thr Ala Asp Ile Asn Thr Phe
    290                 295                 300

Leu Trp Gly Val Ala Asn Arg Gly Ala Ser Ile Arg Val Gly Arg Asp
305                 310                 315                 320

Thr Glu Lys Glu Gly Lys Gly Tyr Phe Glu Asp Arg Arg Pro Ala Ser
                325                 330                 335

Asn Met Asp Pro Tyr Ile Val Thr Ser Met Ile Ala Glu Thr Thr Ile
            340                 345                 350

Leu Trp Asn Pro
        355

<210> SEQ ID NO 13
<211> LENGTH: 1364
<212> TYPE: DNA
```

<213> ORGANISM: Glycine max

<400> SEQUENCE: 13

```
accctatcaa agaaagctac ctagagcttg cacctattgg tatcttctac aatatcctct      60
catagtgctc ttcttcttct tcattttcat tatcaagatg tctttgcttt cggatctcat     120
caacctcaat ctctcagaat ccacagaaaa gatcgttgct gagtacatat gggttggtgg     180
atctggtatg gacctcagaa gcaaagccag gactcttcct gggccagtga gtgaccctgc     240
aaagcttcca agtggaact acgatggctc tagcacagac caagctccag gggatgacag       300
tgaagtcatc ctatacccac aagctatttt caaggacccc tttaggagag caacaatat      360
tcttgtgatt tgtgatgttt acacccccgc tggtgagcca cttccaacca acaagaggta     420
tgatgctgcc aaaattttca gccaccctga cgttgctgct gaggaaccat ggtatggtat     480
tgagcaagaa tataccttgt gcagaaaga tgtaaattgg ccacttgggt ggccacttgg      540
tgggtttcct ggaccacagg gcccatacta ctgtggaact ggtgctgata aagcatatgg     600
ccgtgatatt gtagatgcac attacaaagc ttgtatttat gctggcatca atattagtgg     660
catcaatgga gaggttatgc ctggtcagtg ggaatttcaa gttggtcctt ctgttggtat     720
atctgctgga gatgaggtgt gggcagctcg gtacattttg gagaggatta cagagatggc     780
cggagtaatt gtttcatttg atcccaagcc tattccggga gattggaatg agctggagc      840
tcactcaaac tacagcacca agtccatgag agatgagggt ggttatgagg tgattaagaa     900
ggccattgaa aagcttggat tgaggcacaa ggagcacatt gcagcatatg agaaggcaa      960
cgagagacgt ctcactggaa gacatgaaac tgcagacatc aacaccttct cttggggtgt    1020
ggcaaaccgt ggaagctcca ttagagttgg aagagacaca gagaaaaatg caaaggtta    1080
ctttgaggac agaaggcctg cttctaatat ggatccatat gtagtcacct ccatgatcgc    1140
agagactacc atcctctgga accatgaaa acagtcata tagtctctag atttggacca    1200
ctaaaaattg tgttcaatag tcatttgatc taaaaattta tatttgcaag gtgatgttta    1260
gttaggaatt tctaagtggt cttttttgagc ctccatgtgc catgtctatg gttgagaata    1320
atttcgtcat taataacaag aatttcccat acactgttcc gtgc                     1364
```

<210> SEQ ID NO 14
<211> LENGTH: 356
<212> TYPE: PRT
<213> ORGANISM: Glycine max

<400> SEQUENCE: 14

```
Met Ser Leu Leu Ser Asp Leu Ile Asn Leu Asn Leu Ser Glu Ser Thr
1               5                   10                  15

Glu Lys Ile Val Ala Glu Tyr Ile Trp Val Gly Gly Ser Gly Met Asp
            20                  25                  30

Leu Arg Ser Lys Ala Arg Thr Leu Pro Gly Pro Val Ser Asp Pro Ala
        35                  40                  45

Lys Leu Pro Lys Trp Asn Tyr Asp Gly Ser Ser Thr Asp Gln Ala Pro
    50                  55                  60

Gly Asp Asp Ser Glu Val Ile Leu Tyr Pro Gln Ala Ile Phe Lys Asp
65                  70                  75                  80

Pro Phe Arg Arg Gly Asn Asn Ile Leu Val Ile Cys Asp Val Tyr Thr
                85                  90                  95

Pro Ala Gly Glu Pro Leu Pro Thr Asn Lys Arg Tyr Asp Ala Ala Lys
            100                 105                 110
```

```
Ile Phe Ser His Pro Asp Val Ala Glu Glu Pro Trp Tyr Gly Ile
            115                 120                 125
Glu Gln Glu Tyr Thr Leu Leu Gln Lys Asp Val Asn Trp Pro Leu Gly
        130                 135                 140
Trp Pro Leu Gly Gly Phe Pro Gly Pro Gln Gly Pro Tyr Tyr Cys Gly
145                 150                 155                 160
Thr Gly Ala Asp Lys Ala Tyr Gly Arg Asp Ile Val Asp Ala His Tyr
                165                 170                 175
Lys Ala Cys Ile Tyr Ala Gly Ile Asn Ile Ser Gly Ile Asn Gly Glu
            180                 185                 190
Val Met Pro Gly Gln Trp Glu Phe Gln Val Gly Pro Ser Val Gly Ile
        195                 200                 205
Ser Ala Gly Asp Glu Val Trp Ala Ala Arg Tyr Ile Leu Glu Arg Ile
    210                 215                 220
Thr Glu Met Ala Gly Val Ile Val Ser Phe Asp Pro Lys Pro Ile Pro
225                 230                 235                 240
Gly Asp Trp Asn Gly Ala Gly Ala His Ser Asn Tyr Ser Thr Lys Ser
                245                 250                 255
Met Arg Asp Glu Gly Gly Tyr Glu Val Ile Lys Lys Ala Ile Glu Lys
            260                 265                 270
Leu Gly Leu Arg His Lys Glu His Ile Ala Ala Tyr Gly Glu Gly Asn
        275                 280                 285
Glu Arg Arg Leu Thr Gly Arg His Glu Thr Ala Asp Ile Asn Thr Phe
    290                 295                 300
Ser Trp Gly Val Ala Asn Arg Gly Ser Ser Ile Arg Val Gly Arg Asp
305                 310                 315                 320
Thr Glu Lys Asn Gly Lys Gly Tyr Phe Glu Asp Arg Arg Pro Ala Ser
                325                 330                 335
Asn Met Asp Pro Tyr Val Val Thr Ser Met Ile Ala Glu Thr Thr Ile
            340                 345                 350
Leu Trp Lys Pro
        355

<210> SEQ ID NO 15
<211> LENGTH: 1369
<212> TYPE: DNA
<213> ORGANISM: Glycine max

<400> SEQUENCE: 15
aggaagagaa agaaatttgt ttctctctaa agagtctccg ctgaactttt tggtttcttg      60
aagatgtcgt tactctccga tcttatcaac cttaacctct ccgacatcac cgataaggtg     120
atcgccgagt acatatgggt tggtggatct ggcatggata tgaggagcaa agcaaggact     180
ctctcgggac tggttaatga cccttccaag cttcccaagt ggaactatga tggttccagc     240
actggtcaag ctcctggaca agatagtgaa gtgatcttat atccacaagc aattttccgg     300
gatccattca ggagggtaa caatatcctg gttatgtgtg atgcttacac tcctgctggg     360
gaacccattc ctaccaacaa gagaaataaa gctgcaaaga tattcagtaa tccggatgtt     420
gctgctgaag aaccctggta tggtcttgag caggaatata cattattgca gaaagatgtc     480
caatggcctc ttggatggcc tcttggtggg tttcctgggc ccagggacc atactattgt     540 ggaactggtg ctaacaaggc ttttgggcgt gatattgttg actcacatta caaagcatgt     600
atttatgcgg gaattaacat aagtggaatc aatgagaag tgatgcccgg tcagtgggaa     660
ttccaagttg gtccatcggt tggcatctct gctgctgacg agttgtgggt tgctcgttac     720
```

-continued

```
attttggaga ggatcaccga gattgctgga gtggtgcttt cctttgaccc taaaccaatt      780
cagggtgatt ggaatggtgc tggtgctcac acaaattaca gtaccaagtt gatgagaaac      840
gatggtggct atgaaatcat caaaaaagca attgctaagt tggaaaagag gcacaaagag      900
cacattgctg cttacggaga aggcaatgaa cgtcgtttga ccggacgaca cgagacggct      960
gacatgaaca cctttttatg gggtgttgca accgtggtg cttctattag ggtagggaga     1020
gacactgaaa aggcagggaa gggatacttt gaagatagga ggcctgcctc taacatggac     1080
ccttatgtgg tcacttccat gattgctgag acaactattc tttggaaacc ataagcaacg     1140
tcaaaacaat cacatggtgc cttccgcata gcattgttgt ttagatggtc aatttgtttt     1200
tctatgtttt tgtgtgcatt ctagttgtga ctacctcgcc tgttgttagg tattgtttgt     1260
tggtggtact catgattacc aagcgaggaa ttgttgtttc attttcttaa tgtacgtttt     1320
aagtgttcca ataatgtgta atggccctca agtattgtta tttgctgcg                1369
```

<210> SEQ ID NO 16
<211> LENGTH: 356
<212> TYPE: PRT
<213> ORGANISM: Glycine max

<400> SEQUENCE: 16

```
Met Ser Leu Leu Ser Asp Leu Ile Asn Leu Asn Leu Ser Asp Ile Thr
1               5                   10                  15

Asp Lys Val Ile Ala Glu Tyr Ile Trp Val Gly Gly Ser Gly Met Asp
                20                  25                  30

Met Arg Ser Lys Ala Arg Thr Leu Ser Gly Leu Val Asn Asp Pro Ser
            35                  40                  45

Lys Leu Pro Lys Trp Asn Tyr Asp Gly Ser Ser Thr Gly Gln Ala Pro
        50                  55                  60

Gly Gln Asp Ser Glu Val Ile Leu Tyr Pro Gln Ala Ile Phe Arg Asp
65                  70                  75                  80

Pro Phe Arg Arg Gly Asn Asn Ile Leu Val Met Cys Asp Ala Tyr Thr
                85                  90                  95

Pro Ala Gly Glu Pro Ile Pro Thr Asn Lys Arg Asn Lys Ala Ala Lys
            100                 105                 110

Ile Phe Ser Asn Pro Asp Val Ala Ala Glu Glu Pro Trp Tyr Gly Leu
        115                 120                 125

Glu Gln Glu Tyr Thr Leu Leu Gln Lys Asp Val Gln Trp Pro Leu Gly
    130                 135                 140

Trp Pro Leu Gly Gly Phe Pro Gly Pro Gln Gly Pro Tyr Tyr Cys Gly
145                 150                 155                 160

Thr Gly Ala Asn Lys Ala Phe Gly Arg Asp Ile Val Asp Ser His Tyr
                165                 170                 175

Lys Ala Cys Ile Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ala Ala Asp Glu Leu Trp Val Ala Arg Tyr Ile Leu Glu Arg Ile
    210                 215                 220

Thr Glu Ile Ala Gly Val Val Leu Ser Phe Asp Pro Lys Pro Ile Gln
225                 230                 235                 240

Gly Asp Trp Asn Gly Ala Gly Ala His Thr Asn Tyr Ser Thr Lys Leu
                245                 250                 255
```

Met Arg Asn Asp Gly Gly Tyr Glu Ile Ile Lys Lys Ala Ile Ala Lys
              260                 265                 270

Leu Glu Lys Arg His Lys Glu His Ile Ala Ala Tyr Gly Glu Gly Asn
        275                 280                 285

Glu Arg Arg Leu Thr Gly Arg His Glu Thr Ala Asp Met Asn Thr Phe
    290                 295                 300

Leu Trp Gly Val Ala Asn Arg Gly Ala Ser Ile Arg Val Gly Arg Asp
305                 310                 315                 320

Thr Glu Lys Ala Gly Lys Gly Tyr Phe Glu Asp Arg Arg Pro Ala Ser
                325                 330                 335

Asn Met Asp Pro Tyr Val Val Thr Ser Met Ile Ala Glu Thr Thr Ile
            340                 345                 350

Leu Trp Lys Pro
        355

<210> SEQ ID NO 17
<211> LENGTH: 1579
<212> TYPE: DNA
<213> ORGANISM: Glycine max

<400> SEQUENCE: 17

```
cacttcccac tgtgtctcag ggtctgtgac acacacagac tcacttcaag ttcccagctt    60
ttgccatttt tcccactgtt tattgaacat ggcacagatt ttggctccct ctacgcaatg   120
gcagatgaga atctcaaaat cctctcccaa tgcaactccc attacatcaa acatgtggag   180
ttctttattg tggaaacaaa ataagaaagt ttcacctacc agttctgcta aatttagagt   240
gctggcaatt aagtctgaca atagcaccat caacaggctc gagggtctac ttaatttgga   300
tatcactcca ttcactgaca agataattgc tgagtacatt tggattgggg ggacaggaat   360
tgatgtgcgc agtaaatcaa gaacaatatc aaagcctgtt gaagatccct ctgagctccc   420
taaatggaac tatgatggat ctagcactgg acaggcacct ggtgatgata gtgaagtaat   480
cctatatcct caagcaattt tcaaagatcc tttccgtggc ggtaacaata ttttggtcat   540
ttgcgattct tacaccccac aaggtgagcc tatccctaca acaagagac acagagctgc   600
tgaaattttc agtaacccaa aggtccaagc tgaagttcca tggtatgaa agaacaaga   660
gtacaccta cttcaaacaa atgtgaaatg ccattagga tggccggttg gtggctatcc   720
cggtcctcag ggtccttatt attgcagtgc tggggcagat aagtcatttg acgtgacat   780
atctgatgct cattacaagg cttgcttata tgctggaatt aacatcagtg caccaatgg   840
ggaggttatg cctgggcagt gggagtacca agttggtcct agtgtaggta ttgaggctgg   900
tgatcatatc tgggcttcaa ggtacatcct cgagagaatt actgagcaag ctggtgttgt   960
gctctctctt gatccaaaac caatagaggg tgactggaat ggagcaggat gccacaccaa  1020
ttacagtaca aagagcatga gggaagatgg aggctttgag gtaataaaga aggcaatttt  1080
gaatctatcg ctacgccaca aggatcacat cagtgcatat ggagaaggaa atgagagaag  1140
gttgacagga aagcatgaga cagcaagcat taacacattt tcttggggag tggctaaccg  1200
tggttgctca atccgtgtgg gaagagacac agagaagaat ggcaaaggtt acttggaaga  1260
caggcgaccg gcttcaaaca tggatccata tgttgtgaca tcattacttg cagagactac  1320
actattgtgg gagccaactc tggaggctga agctcttgca gctcagaagt tagcattgaa  1380
ggtctaaacc tattgaatga tggcattctg gatgcaaaat cactttcctt ttagattatc  1440
tatatgtatt ctaatgatct tgtttggact aaagaggttg ccatgcccag ttattggtta  1500
```

```
tcatatgaaa tgcacattgt atatcagaag tttggttggt actatttgct tcaggacaaa    1560
ttttctttga tgcttggtt                                                  1579
```

<210> SEQ ID NO 18
<211> LENGTH: 432
<212> TYPE: PRT
<213> ORGANISM: Glycine max

<400> SEQUENCE: 18

```
Met Ala Gln Ile Leu Ala Pro Ser Thr Gln Trp Gln Met Arg Ile Ser
  1               5                  10                  15

Lys Ser Ser Pro Asn Ala Thr Pro Ile Thr Ser Asn Met Trp Ser Ser
             20                  25                  30

Leu Leu Trp Lys Gln Asn Lys Lys Val Ser Pro Thr Ser Ser Ala Lys
         35                  40                  45

Phe Arg Val Leu Ala Ile Lys Ser Asp Asn Ser Thr Ile Asn Arg Leu
     50                  55                  60

Glu Gly Leu Leu Asn Leu Asp Ile Thr Pro Phe Thr Asp Lys Ile Ile
 65                  70                  75                  80

Ala Glu Tyr Ile Trp Ile Gly Gly Thr Gly Ile Asp Val Arg Ser Lys
                 85                  90                  95

Ser Arg Thr Ile Ser Lys Pro Val Glu Asp Pro Ser Glu Leu Pro Lys
            100                 105                 110

Trp Asn Tyr Asp Gly Ser Ser Thr Gly Gln Ala Pro Gly Asp Asp Ser
        115                 120                 125

Glu Val Ile Leu Tyr Pro Gln Ala Ile Phe Lys Asp Pro Phe Arg Gly
    130                 135                 140

Gly Asn Asn Ile Leu Val Ile Cys Asp Ser Tyr Thr Pro Gln Gly Glu
145                 150                 155                 160

Pro Ile Pro Thr Asn Lys Arg His Arg Ala Ala Glu Ile Phe Ser Asn
                165                 170                 175

Pro Lys Val Gln Ala Glu Val Pro Trp Tyr Gly Ile Glu Gln Glu Tyr
            180                 185                 190

Thr Leu Leu Gln Thr Asn Val Lys Trp Pro Leu Gly Trp Pro Val Gly
        195                 200                 205

Gly Tyr Pro Gly Pro Gln Gly Pro Tyr Tyr Cys Ser Ala Gly Ala Asp
    210                 215                 220

Lys Ser Phe Gly Arg Asp Ile Ser Asp Ala His Tyr Lys Ala Cys Leu
225                 230                 235                 240

Tyr Ala Gly Ile Asn Ile Ser Gly Thr Asn Gly Glu Val Met Pro Gly
                245                 250                 255

Gln Trp Glu Tyr Gln Val Gly Pro Ser Val Gly Ile Glu Ala Gly Asp
            260                 265                 270

His Ile Trp Ala Ser Arg Tyr Ile Leu Glu Arg Ile Thr Glu Gln Ala
        275                 280                 285

Gly Val Val Leu Ser Leu Asp Pro Lys Pro Ile Glu Gly Asp Trp Asn
    290                 295                 300

Gly Ala Gly Cys His Thr Asn Tyr Ser Thr Lys Ser Met Arg Glu Asp
305                 310                 315                 320

Gly Gly Phe Glu Val Ile Lys Lys Ala Ile Leu Asn Leu Ser Leu Arg
                325                 330                 335

His Lys Asp His Ile Ser Ala Tyr Gly Glu Gly Asn Glu Arg Arg Leu
            340                 345                 350

Thr Gly Lys His Glu Thr Ala Ser Ile Asn Thr Phe Ser Trp Gly Val
```

|  |  |  | 355 |  |  |  | 360 |  |  |  | 365 |  |  |
|---|---|---|---|---|---|---|---|---|---|---|---|---|---|

Ala Asn Arg Gly Cys Ser Ile Arg Val Gly Arg Asp Thr Glu Lys Asn
    370                                375                          380

Gly Lys Gly Tyr Leu Glu Asp Arg Arg Pro Ala Ser Asn Met Asp Pro
385                              390                              395                        400

Tyr Val Val Thr Ser Leu Leu Ala Glu Thr Leu Leu Trp Glu Pro
                405                          410                            415

Thr Leu Glu Ala Glu Ala Leu Ala Ala Gln Lys Leu Ala Leu Lys Val
    420                                425                          430

<210> SEQ ID NO 19
<211> LENGTH: 1425
<212> TYPE: DNA
<213> ORGANISM: Glycine max

<400> SEQUENCE: 19

```
atgtcgttgc tctccgatct tatcaacctt aacctctccg acatcaccga taaaacactc      60
tcaggaccgg ttaaagaccc ttcgaagctt cccaagtgga actatgatgg ttccagcact     120
ggtcaagctc ctgggcaaga tagtgaagtg atcttatatc acaagcaat tttcaaggat      180
ccattcagga ggggtagcaa tatcctggtt atgtgtgatg cttacactcc tgctggggaa     240
cccattccta caaacaagag aaataatgct gcaaagatat cggccatcc tgatgttgct      300
gctgaagaac cctgttactg catgatttc aaacagggac atattattg tggtactggt       360
gctaacaagg ctttcgggcg tgatattgtt gactcacatt acaaagcatg tatttatgcg     420
ggcattaaca tcagtggaat caatggagaa gtgatgcctg tcagaggat caccgagatt      480
gcaggagtgg tgcttttcctt tgaccctaaa ccaattcagt ccatgagaaa cgatggtggc    540
tatgaagtca tcaaaaagc aattgctaag ttggaaaaga cacaagga gcacattgca        600
gcttacggag aaggcaacga acgtcgtttg actggacgac acgagacagc tgacatgaac     660
acctttgtat ggagttgcca atggtggtgt gggtggagg ttgggcacaa tggcgttggg      720
tgggtggcta cagaagtagt tttatctgtt tgggtgtttt tggaggtgca agaagtaaaa     780
agggtgatgc aggaagtaaa agacggtaaa catagttttg atttcttgaa gatgtcgtta    840
ctctccgatc taatcaacat taacctctcc gacaccacca agaagggtcc atactattgt     900
ggtattggtg ctaacaaggc ttttggacgt gacattgttg actctcattt caaagcctgt     960
ctttatgcag acatcaacat tactggaatt aatgcagaag tgatgcctgg tcagtgggaa   1020
ttccgtgttg gtccatcgct ggcatctctg cgtgtgacga cttgtgggtt gctcgctaca   1080
ttttggaggt tgttagcaca cgactactct catcatcaaa ttctttcttt tgtaaatatt    1140
gcagcgaata tctctgtttg tgctaatatc tctgtttgtg ctaatatctc tgtggtggtg   1200
ctttcctttt atcctcaacc gattaagggt gattggaatt gtgctagtgc tcacacgaat   1260
tacagtacca agtcgatgag aaatgatggt ggctatgaag tcattagaaa agcaactgcc   1320
aagttggaaa aaaggcataa ggagcacatt gctgcttatg gagaaggcaa tgaacgtcgt   1380
ttgacaggtc aacatgagac agctgatatt aacaccttca taagg                    1425
```

<210> SEQ ID NO 20
<211> LENGTH: 475
<212> TYPE: PRT
<213> ORGANISM: Glycine max

<400> SEQUENCE: 20

Met Ser Leu Leu Ser Asp Leu Ile Asn Leu Asn Leu Ser Asp Ile Thr

```
1               5                    10                   15
Asp Lys Thr Leu Ser Gly Pro Val Lys Asp Pro Ser Lys Leu Pro Lys
            20                  25                  30

Trp Asn Tyr Asp Gly Ser Ser Thr Gly Gln Ala Pro Gly Gln Asp Ser
            35                  40                  45

Glu Val Ile Leu Tyr Pro Gln Ala Ile Phe Lys Asp Pro Phe Arg Arg
 50                  55                  60

Gly Ser Asn Ile Leu Val Met Cys Asp Ala Tyr Thr Pro Ala Gly Glu
 65                  70                  75                  80

Pro Ile Pro Thr Asn Lys Arg Asn Asn Ala Ala Lys Ile Phe Gly His
            85                  90                  95

Pro Asp Val Ala Ala Glu Glu Pro Cys Tyr Cys Met Ile Phe Lys Gln
            100                 105                 110

Gly Pro Tyr Tyr Cys Gly Thr Gly Ala Asn Lys Ala Phe Gly Arg Asp
            115                 120                 125

Ile Val Asp Ser His Tyr Lys Ala Cys Ile Tyr Ala Gly Ile Asn Ile
 130                 135                 140

Ser Gly Ile Asn Gly Glu Val Met Pro Gly Gln Arg Ile Thr Glu Ile
145                 150                 155                 160

Ala Gly Val Val Leu Ser Phe Asp Pro Lys Pro Ile Gln Ser Met Arg
            165                 170                 175

Asn Asp Gly Gly Tyr Glu Val Ile Lys Lys Ala Ile Ala Lys Leu Glu
            180                 185                 190

Lys Arg His Lys Glu His Ile Ala Ala Tyr Gly Glu Gly Asn Glu Arg
            195                 200                 205

Arg Leu Thr Gly Arg His Glu Thr Ala Asp Met Asn Thr Phe Val Trp
 210                 215                 220

Ser Cys Gln Trp Trp Cys Trp Val Glu Val Gly His Asn Gly Val Trp
225                 230                 235                 240

Trp Val Ala Thr Glu Val Val Leu Ser Val Trp Val Phe Leu Glu Val
            245                 250                 255

Gln Glu Val Lys Arg Val Met Gln Glu Val Lys Asp Gly Lys His Ser
            260                 265                 270

Phe Asp Phe Leu Lys Met Ser Leu Leu Ser Asp Leu Ile Asn Ile Asn
            275                 280                 285

Leu Ser Asp Thr Thr Lys Lys Gly Pro Tyr Tyr Cys Gly Ile Gly Ala
 290                 295                 300

Asn Lys Ala Phe Gly Arg Asp Ile Val Asp Ser His Phe Lys Ala Cys
305                 310                 315                 320

Leu Tyr Ala Asp Ile Asn Ile Thr Gly Ile Asn Ala Glu Val Met Pro
            325                 330                 335

Gly Gln Trp Glu Phe Arg Val Gly Pro Ser Leu Ala Ser Leu Arg Val
            340                 345                 350

Thr Thr Cys Gly Leu Leu Ala Thr Phe Trp Arg Leu Leu Ala His Asp
            355                 360                 365

Tyr Ser His His Gln Ile Leu Ser Phe Val Asn Ile Ala Ala Asn Ile
 370                 375                 380

Ser Val Cys Ala Asn Ile Ser Val Cys Ala Asn Ile Ser Val Val Val
385                 390                 395                 400

Leu Ser Phe Tyr Pro Gln Pro Ile Lys Gly Asp Trp Asn Cys Ala Ser
            405                 410                 415

Ala His Thr Asn Tyr Ser Thr Lys Ser Met Arg Asn Asp Gly Gly Tyr
            420                 425                 430
```

Glu Val Ile Arg Lys Ala Thr Ala Lys Leu Glu Lys Arg His Lys Glu
        435                 440                 445

His Ile Ala Ala Tyr Gly Glu Gly Asn Glu Arg Arg Leu Thr Gly Gln
    450                 455                 460

His Glu Thr Ala Asp Ile Asn Thr Phe Ile Arg
465                 470                 475

<210> SEQ ID NO 21
<211> LENGTH: 1454
<212> TYPE: DNA
<213> ORGANISM: Glycine max

<400> SEQUENCE: 21

```
acatcttctt ttacgtattg aatctcagaa ttctctaaaa gagatctttt tctgctcttt      60
gaagaaagaa gggtctttgc ttgattttgg agatgtctct gctctcagat ctcatcaacc     120
ttaacctctc cgataccacc gagaaggtga tcgcagagta catatggatc ggtggatcag     180
gaatggacct gaggagcaaa gcaaggactc tcccaggacc agttagcgac ccttcagagc     240
ttcccaagtg gaactatgat ggttccagca caggtcaagc tcctggtgaa gacagtgaag     300
tgatttata cccacaagcc attttcaggg atccattcag aaggggtaac aatatcttgg      360
ttatctgtga tgcctacact cctgctggag aacctattcc cactaacaag aggcacgctg     420
ctgccaaggt tttcagccat cctgatgttg ttgctgaagt gccatggtac ggtattgaac     480
aagaatacac cttgttgcag aaagatatcc aatggcctct tgggtggcct gttggtggtt     540
tccctggacc tcagggtcca tactactgtg tgttggcgc tgacaaggct tttggccgtg      600
acattgttga cgcacactac aaagcctgta tttatgctgg catcaacatc agtggaatta     660
atggagaagt gatgcccggt cagtgggaat tccaagttgg accttcagtt ggaatctcag     720
ctggtgatga gatttgggca gctcgttaca tcttggagag gatcactgag attgctggtg     780
tggtggtttc ctttgacccc aagccaatta agggtgattg gaatggtgct ggtgctcaca     840
caaactacag caccaagtcc atgagagaag atggtggcta tgaagtgatc aaagcagcaa     900
ttgacaagtt ggggaagaag cacaaggagc acattgctgc ttatggagaa ggcaacgaac     960
gtcgtttgac aggacgccac gaaaccgctg acatcaacac cttcttatgg ggagttgcaa    1020
accgtggagc ttctgttagg gttgggagag acacagagaa agcagggaag gatattttg     1080
aggacagaag gccagcttcc aacatggacc catacgtggt tacttccatg attgcagaca    1140
caaccattct gtgaagcca tgagcaaaac ctgcatgttt ctcccttg gatggaaagg       1200
aacagttatg ctttcttag taggatttgg tctctctctc ttttacctt tgattggta       1260
ctatggttgg tgccttgttg gttggtgcaa ctaactggca agggttgttc attgtttct     1320
tctattcctt tccctcgttt tccgattgtt acaatgacaa taattaatg gttattatca    1380
gtcttgaaca agaaatgct gattgtgaag tataataata atatatgaaa ttgtcatgtt    1440
cattggagta ggaa                                                     1454
```

<210> SEQ ID NO 22
<211> LENGTH: 356
<212> TYPE: PRT
<213> ORGANISM: Glycine max

<400> SEQUENCE: 22

Met Ser Leu Leu Ser Asp Leu Ile Asn Leu Asn Leu Ser Asp Thr Thr
1               5                   10                  15

Glu Lys Val Ile Ala Glu Tyr Ile Trp Ile Gly Ser Gly Met Asp
            20                  25                  30

Leu Arg Ser Lys Ala Arg Thr Leu Pro Gly Pro Val Ser Asp Pro Ser
        35                  40                  45

Glu Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Arg Asp
65                  70                  75                  80

Pro Phe Arg Arg Gly Asn Asn Ile Leu Val Ile Cys Asp Ala Tyr Thr
                85                  90                  95

Pro Ala Gly Glu Pro Ile Pro Thr Asn Lys Arg His Ala Ala Ala Lys
            100                 105                 110

Val Phe Ser His Pro Asp Val Val Ala Glu Val Pro Trp Tyr Gly Ile
        115                 120                 125

Glu Gln Glu Tyr Thr Leu Leu Gln Lys Asp Ile Gln Trp Pro Leu Gly
    130                 135                 140

Trp Pro Val Gly Gly Phe Pro Gly Pro Gln Gly Pro Tyr Tyr Cys Gly
145                 150                 155                 160

Val Gly Ala Asp Lys Ala Phe Gly Arg Asp Ile Val Asp Ala His Tyr
                165                 170                 175

Lys Ala Cys Ile Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ala Gly Asp Glu Ile Trp Ala Ala Arg Tyr Ile Leu Glu Arg Ile
    210                 215                 220

Thr Glu Ile Ala Gly Val Val Ser Phe Asp Pro Lys Pro Ile Lys
225                 230                 235                 240

Gly Asp Trp Asn Gly Ala Gly Ala His Thr Asn Tyr Ser Thr Lys Ser
                245                 250                 255

Met Arg Glu Asp Gly Gly Tyr Glu Val Ile Lys Ala Ala Ile Asp Lys
            260                 265                 270

Leu Gly Lys Lys His Lys Glu His Ile Ala Ala Tyr Gly Glu Gly Asn
        275                 280                 285

Glu Arg Arg Leu Thr Gly Arg His Glu Thr Ala Asp Ile Asn Thr Phe
    290                 295                 300

Leu Trp Gly Val Ala Asn Arg Gly Ala Ser Val Arg Val Gly Arg Asp
305                 310                 315                 320

Thr Glu Lys Ala Gly Lys Gly Tyr Phe Glu Asp Arg Arg Pro Ala Ser
                325                 330                 335

Asn Met Asp Pro Tyr Val Val Thr Ser Met Ile Ala Asp Thr Thr Ile
            340                 345                 350

Leu Trp Lys Pro
        355

<210> SEQ ID NO 23
<211> LENGTH: 1446
<212> TYPE: DNA
<213> ORGANISM: Glycine max

<400> SEQUENCE: 23
aagattctaa gagagatttt gctgctcttt gaagaagggt gtttgcttga ttttggagat    60
gtcgctgctc tcagatctca tcaaccttaa cctctcagac actactgaga aggtgatcgc   120
agagtacata tggatcggtg gatcaggaat ggacctgagg agcaaagcaa ggactctccc   180

-continued

```
aggaccagtt agcgacccct caaagcttcc caagtggaac tatgatggtt ccagcacagg    240
ccaagctcct ggagaagaca gtgaagtgat tatatacccca caagccattt tcagggatcc   300
attcagaagg ggcaacaata tcttggttat ctgtgatact tacactccag ctggagaacc    360
cattcccact aacaagaggc acgatgctgc caaggttttc agccatcctg atgttgttgc    420
tgaagagaca tggtatggta ttgagcagga atacaccttg ttgcagaaag atatccaatg    480
gcctcttggg tggcctgttg gtggtttccc tggaccacag ggtccatact actgtggtgt    540
tggcgctgac aaggcttttg gccgtgacat tgttgacgca cattacaaag cctgtcttta    600
tgctggcatc aacatcagtg gaattaatgg agaagtgatg cccggtcagt gggaattcca    660
agttggacct tcagttggaa tctcagctgg tgacgaggtg tgggcagctc gttacatctt    720
ggagaggatc actgagattg ctggtgtggt ggtttccttt gatcccaagc caattcaggg    780
tgattggaat ggtgctggtg ctcacacaaa ctacagcact aagtccatga gaaatgatgg    840
tggctatgaa gtgatcaaaa ccgccattga gaagttgggg aagagacaca aggagcacat    900
tgctgcttat ggagaaggca acgagcgtcg tttgacaggg cgccacgaaa ccgctgacat    960
caacaccttc ttatggggag ttgcaaaccg tggagcttca gttagggttg ggagggacac   1020
agagaaagca gggaagggat attttgagga cagaaggcca gcttctaaca tggacccata   1080
tgtggttact tccatgattg cagacacaac cattctgtgg aagccatgag caaaacttgc   1140
atgttgtctc cctttggatg gaacaaggaa caaggaacaa ggaacaagga acagttatgc   1200 tttctaagt agggtttggt cctttttatt tttaccttt tgattttct aggatttcga      1260 tttgtggcta ctttggttgg tgcaaccaac tgccaagggt tgttcattgt tttctattcc   1320
tttccctcgt tttccgattg ttacaataat aataatgtaa tatggttatt ttcagtctca   1380
aacaaaagta atgctgattg tgaagtataa taatatatga aattgtcatg tccattggag   1440
ttggga                                                              1446
```

<210> SEQ ID NO 24
<211> LENGTH: 356
<212> TYPE: PRT
<213> ORGANISM: Glycine max

<400> SEQUENCE: 24

Met Ser Leu Leu Ser Asp Leu Ile Asn Leu Asn Leu Ser Asp Thr Thr
1               5                   10                  15

Glu Lys Val Ile Ala Glu Tyr Ile Trp Ile Gly Gly Ser Gly Met Asp
            20                  25                  30

Leu Arg Ser Lys Ala Arg Thr Leu Pro Gly Pro Val Ser Asp Pro Ser
        35                  40                  45

Lys Leu Pro Lys Trp Asn Tyr Asp Gly Ser Ser Thr Gly Gln Ala Pro
    50                  55                  60

Gly Glu Asp Ser Glu Val Ile Ile Tyr Pro Gln Ala Ile Phe Arg Asp
65                  70                  75                  80

Pro Phe Arg Arg Gly Asn Asn Ile Leu Val Ile Cys Asp Thr Tyr Thr
                85                  90                  95

Pro Ala Gly Glu Pro Ile Pro Thr Asn Lys Arg His Asp Ala Ala Lys
            100                 105                 110

Val Phe Ser His Pro Asp Val Val Ala Glu Glu Thr Trp Tyr Gly Ile
        115                 120                 125

Glu Gln Glu Tyr Thr Leu Leu Gln Lys Asp Ile Gln Trp Pro Leu Gly
    130                 135                 140

```
Trp Pro Val Gly Gly Phe Pro Gly Pro Gln Gly Pro Tyr Tyr Cys Gly
145                 150                 155                 160

Val Gly Ala Asp Lys Ala Phe Gly Arg Asp Ile Val Asp Ala His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ala Gly Asp Glu Val Trp Ala Ala Arg Tyr Ile Leu Glu Arg Ile
    210                 215                 220

Thr Glu Ile Ala Gly Val Val Ser Phe Asp Pro Lys Pro Ile Gln
225                 230                 235                 240

Gly Asp Trp Asn Gly Ala Gly Ala His Thr Asn Tyr Ser Thr Lys Ser
                245                 250                 255

Met Arg Asn Asp Gly Gly Tyr Glu Val Ile Lys Thr Ala Ile Glu Lys
                260                 265                 270

Leu Gly Lys Arg His Lys Glu His Ile Ala Ala Tyr Gly Glu Gly Asn
            275                 280                 285

Glu Arg Arg Leu Thr Gly Arg His Glu Thr Ala Asp Ile Asn Thr Phe
290                 295                 300

Leu Trp Gly Val Ala Asn Arg Gly Ala Ser Val Arg Val Gly Arg Asp
305                 310                 315                 320

Thr Glu Lys Ala Gly Lys Gly Tyr Phe Glu Asp Arg Arg Pro Ala Ser
                325                 330                 335

Asn Met Asp Pro Tyr Val Val Thr Ser Met Ile Ala Asp Thr Thr Ile
                340                 345                 350

Leu Trp Lys Pro
        355
```

<210> SEQ ID NO 25
<211> LENGTH: 1525
<212> TYPE: DNA
<213> ORGANISM: Glycine max

<400> SEQUENCE: 25

| | | | | | |
|---|---|---|---|---|---|
| gaaaaccata | gattatcgct | atcttatatc | ttattccggg | tctcaagatt | caactgtgag | 60 |
| gaagaaaaag | gtctccaaac | acatagaagc | acgtgtatgt | atgtattgtg | caagtcatag | 120 |
| tattcaacgt | taacaccact | gactcactta | taaaaggcgc | tttaacacca | aacggagtct | 180 |
| ctctatcaaa | aaaagctacc | tagagcttgc | acctattggt | atcttctaca | atatcctaaa | 240 |
| gtgttttttct | tcttcttcat | caccatgtct | ttactttcag | acctcatcaa | cctcaatctc | 300 |
| tcagaatcca | cagaaaagat | cattgctgag | tacatatggg | ttggtggatc | tggtatggac | 360 |
| ctcagaagca | aagccaggac | tcttcctggg | ccagtgagtg | accctgcaaa | acttccgaag | 420 |
| tggaactatg | atgggtctag | cacagatcaa | gctccagggg | atgacagtga | agtcattcta | 480 |
| tacccacaag | ctattttcaa | ggaccccttt | aggagaggaa | acaatattct | tgtcatttgt | 540 |
| gatgtgtaca | ccccagctgg | tgagccactt | ccaaccaaca | agaggtatgg | tgctgccaaa | 600 |
| attttcagtc | accctgatgt | tgctgctgag | gaaccatggt | atggtattga | gcaagagtat | 660 |
| accttattgc | agaaagatgt | aaattggcca | cttgggtggc | cccttggtgg | gtttcctgga | 720 |
| ccacagggcc | catactactg | tggaattggt | gctgataaag | cctatggccg | tgatattgta | 780 |
| gatgcacatt | acaaagcttg | tatttatgct | ggcattaaca | ttagtggcat | caatggagag | 840 |

-continued

```
gttatgcctg gccagtggga atttcaagtt ggtccttctg ttggtatctc tgctggagat    900
gaggtgtggg ctgctcgcta cattttggag aggattacag agatagctgg agcaattgtt    960
tcatttgatc ccaagcctat tccgggagat tggaatggag ctggagctca ctcaaactac   1020
agcaccaagt ccatgagaga agagggtggt tatgaggtga tcaagaaggc cattgaaaag   1080
cttggattga ggcacaagga gcacatcgca gcatatggag aaggcaacga gagacgtctc   1140
acgggaagac atgaaactgc agacatcaac accttctctt ggggtgtggc aaaccgtgga   1200
agctccatta gagttggaag agacacagag aaaaatggca aaggttactt cgaggacaga   1260
aggcctgctt ctaatatgga tccctatgta gtcacctcca tgatcgcaga gactaccatc   1320
ctctggaaac catgaaaaca cagtcatatg tctctagatt tggaccactt aaaattgtgt   1380
gttcaatagt catttgatct aaaattttat atttgcaagg tgttgtttag ttaggaattg   1440
ccaagtggtc ttttgagcct ccatgtacca tgtgtatggt agagaataat ctcttcatta   1500
ataacaagaa ttgcttcttg atttc                                         1525
```

<210> SEQ ID NO 26
<211> LENGTH: 356
<212> TYPE: PRT
<213> ORGANISM: Glycine max

<400> SEQUENCE: 26

```
Met Ser Leu Leu Ser Asp Leu Ile Asn Leu Asn Leu Ser Glu Ser Thr
1               5                   10                  15
Glu Lys Ile Ile Ala Glu Tyr Ile Trp Val Gly Gly Ser Gly Met Asp
            20                  25                  30
Leu Arg Ser Lys Ala Arg Thr Leu Pro Gly Pro Val Ser Asp Pro Ala
        35                  40                  45
Lys Leu Pro Lys Trp Asn Tyr Asp Gly Ser Ser Thr Asp Gln Ala Pro
    50                  55                  60
Gly Asp Asp Ser Glu Val Ile Leu Tyr Pro Gln Ala Ile Phe Lys Asp
65                  70                  75                  80
Pro Phe Arg Arg Gly Asn Asn Ile Leu Val Ile Cys Asp Val Tyr Thr
                85                  90                  95
Pro Ala Gly Glu Pro Leu Pro Thr Asn Lys Arg Tyr Gly Ala Ala Lys
            100                 105                 110
Ile Phe Ser His Pro Asp Val Ala Ala Glu Glu Pro Trp Tyr Gly Ile
        115                 120                 125
Glu Gln Glu Tyr Thr Leu Leu Gln Lys Asp Val Asn Trp Pro Leu Gly
    130                 135                 140
Trp Pro Leu Gly Gly Phe Pro Gly Pro Gln Gly Pro Tyr Tyr Cys Gly
145                 150                 155                 160
Ile Gly Ala Asp Lys Ala Tyr Gly Arg Asp Ile Val Asp Ala His Tyr
                165                 170                 175
Lys Ala Cys Ile Tyr Ala Gly Ile Asn Ile Ser Gly Ile Asn Gly Glu
            180                 185                 190
Val Met Pro Gly Gln Trp Glu Phe Gln Val Gly Pro Ser Val Gly Ile
        195                 200                 205
Ser Ala Gly Asp Glu Val Trp Ala Ala Arg Tyr Ile Leu Glu Arg Ile
    210                 215                 220
Thr Glu Ile Ala Gly Ala Ile Val Ser Phe Asp Pro Lys Pro Ile Pro
225                 230                 235                 240
Gly Asp Trp Asn Gly Ala Gly Ala His Ser Asn Tyr Ser Thr Lys Ser
                245                 250                 255
```

Met Arg Glu Glu Gly Gly Tyr Glu Val Ile Lys Lys Ala Ile Glu Lys
        260                 265                 270

Leu Gly Leu Arg His Lys Glu His Ile Ala Ala Tyr Gly Glu Gly Asn
            275                 280                 285

Glu Arg Arg Leu Thr Gly Arg His Glu Thr Ala Asp Ile Asn Thr Phe
290                 295                 300

Ser Trp Gly Val Ala Asn Arg Gly Ser Ser Ile Arg Val Gly Arg Asp
305                 310                 315                 320

Thr Glu Lys Asn Gly Lys Gly Tyr Phe Glu Asp Arg Arg Pro Ala Ser
                325                 330                 335

Asn Met Asp Pro Tyr Val Val Thr Ser Met Ile Ala Glu Thr Thr Ile
            340                 345                 350

Leu Trp Lys Pro
        355

<210> SEQ ID NO 27
<211> LENGTH: 1692
<212> TYPE: DNA
<213> ORGANISM: Glycine max

<400> SEQUENCE: 27

| | | | | | |
|---|---|---|---|---|---|
| aaaccaattt | catccactcg | taacgtaccc | ctatcggttt | tagaaaagcc | aacaaagttt | 60 |
| gtgtccacca | acctctattt | tacacgagtc | tctcatattc | tgatactata | gctacactta | 120 |
| ccactgtgtc | tcagagggtc | tgtgacacac | agactcactt | ccaagttcca | agctttggcc | 180 |
| atttattccc | actgtttatt | gaacatggca | cagattttgg | ctccctctac | gcaatggcag | 240 |
| atgagaatct | caaaatcctc | tcccaatgca | agtcccatta | catcaaacat | gtggagttct | 300 |
| ttattgtgga | aacaaaataa | gaaagtttca | cccacaagtt | ctgctaaatt | tagagtgatg | 360 |
| gcaattaagt | ctgacaatag | catcatcaac | aggctagagg | gtctacttaa | tttggatatc | 420 |
| actccattca | cggacaagat | aattgctgag | tacatttgga | ttgggggggac | aggaattgat | 480 |
| gtgcgcagta | aatcaagaac | aatatcaaag | cctgttgaac | atccctctga | gctccctaaa | 540 |
| tggaactatg | atggatctag | cactggacag | gcaccgggtg | atgatagtga | agtaatccta | 600 |
| tatcctcaag | caatttttcaa | agatcctttc | cgtggtggta | acaatatttt | ggtcatttgc | 660 |
| gattcttaca | ccccacaagg | tgagcctatc | cctacaaaca | agagacacag | agctgctgaa | 720 |
| attttcagta | acccaaaggt | ccaagcagaa | gttccatggt | atggaataga | acaagagtac | 780 |
| accttacttc | aaacaaatgt | gaaatggcca | ttaggttggc | ccgttggtgg | ctatcctggt | 840 |
| cctcagggtc | cttattattg | cagcgctggg | gcagacaagt | catttggacg | tgacatatct | 900 |
| gatgctcatt | acaaggcttg | cttatatgct | ggaattaaca | tcagtggtac | caatggggag | 960 |
| gttatgcctg | ggcagtggga | gtaccaagtt | ggtcctagtg | taggtattga | ggctggtgat | 1020 |
| catatctggg | cttcaaggta | catcctcgag | agaattaccg | agcaagctgg | tgttgtgctc | 1080 |
| tctcttgatc | caaaaccaat | agagggtgac | tggaatggag | caggatgcca | caccaattac | 1140 |
| agtacaaaga | gcatgaggga | agatggaggc | tttgaggtaa | taagaaggc | aatattgaat | 1200 |
| ctatcgcttc | gccacaaaga | tcacatcagt | gcatatggag | aaggaaatga | gagaaggttg | 1260 |
| actggaaagc | atgagacagc | aagcatcaac | acattttctt | ggggagtggc | taaccgtggt | 1320 |
| tgctcaatcc | gtgtgggaag | agacactgag | aagaatggca | aggttacttg | gaagatagg | 1380 |
| cgaccggctt | caaacatgga | tccatatgtt | gtgacatcat | tacttgcaga | gactacacta | 1440 |
| ttgtgggagc | caactctgga | ggctgaagct | cttgcagctc | agaagttagc | attgaaggtc | 1500 |

```
taaacctatt gattgatgag gagctggaaa atactttcac tttccttta gattatctat    1560 attataatga tcttgtttgg actaaagagg ttgccatgcc cagttattgg ttgtcatatg    1620
aaatgcatat tgtatatcag aagtttggtt ggtactattt gcttcaggac aaatttgcat    1680
tgatgcttgg tt                                                         1692
```

<210> SEQ ID NO 28
<211> LENGTH: 432
<212> TYPE: PRT
<213> ORGANISM: Glycine max

<400> SEQUENCE: 28

```
Met Ala Gln Ile Leu Ala Pro Ser Thr Gln Trp Gln Met Arg Ile Ser
1               5                   10                  15

Lys Ser Ser Pro Asn Ala Ser Pro Ile Thr Ser Asn Met Trp Ser Ser
            20                  25                  30

Leu Leu Trp Lys Gln Asn Lys Lys Val Ser Pro Thr Ser Ser Ala Lys
        35                  40                  45

Phe Arg Val Met Ala Ile Lys Ser Asp Asn Ser Ile Ile Asn Arg Leu
    50                  55                  60

Glu Gly Leu Leu Asn Leu Asp Ile Thr Pro Phe Thr Asp Lys Ile Ile
65                  70                  75                  80

Ala Glu Tyr Ile Trp Ile Gly Gly Thr Gly Ile Asp Val Arg Ser Lys
                85                  90                  95

Ser Arg Thr Ile Ser Lys Pro Val Glu His Pro Ser Glu Leu Pro Lys
            100                 105                 110

Trp Asn Tyr Asp Gly Ser Ser Thr Gly Gln Ala Pro Gly Asp Asp Ser
        115                 120                 125

Glu Val Ile Leu Tyr Pro Gln Ala Ile Phe Lys Asp Pro Phe Arg Gly
    130                 135                 140

Gly Asn Asn Ile Leu Val Ile Cys Asp Ser Tyr Thr Pro Gln Gly Glu
145                 150                 155                 160

Pro Ile Pro Thr Asn Lys Arg His Arg Ala Ala Glu Ile Phe Ser Asn
                165                 170                 175

Pro Lys Val Gln Ala Glu Val Pro Trp Tyr Gly Ile Glu Gln Glu Tyr
            180                 185                 190

Thr Leu Leu Gln Thr Asn Val Lys Trp Pro Leu Gly Trp Pro Val Gly
        195                 200                 205

Gly Tyr Pro Gly Pro Gln Gly Pro Tyr Tyr Cys Ser Ala Gly Ala Asp
    210                 215                 220

Lys Ser Phe Gly Arg Asp Ile Ser Asp Ala His Tyr Lys Ala Cys Leu
225                 230                 235                 240

Tyr Ala Gly Ile Asn Ile Ser Gly Thr Asn Gly Glu Val Met Pro Gly
                245                 250                 255

Gln Trp Glu Tyr Gln Val Gly Pro Ser Val Gly Ile Glu Ala Gly Asp
            260                 265                 270

His Ile Trp Ala Ser Arg Tyr Ile Leu Glu Arg Ile Thr Glu Gln Ala
        275                 280                 285

Gly Val Val Leu Ser Leu Asp Pro Lys Pro Ile Glu Gly Asp Trp Asn
    290                 295                 300

Gly Ala Gly Cys His Thr Asn Tyr Ser Thr Lys Ser Met Arg Glu Asp
305                 310                 315                 320

Gly Gly Phe Glu Val Ile Lys Lys Ala Ile Leu Asn Leu Ser Leu Arg
                325                 330                 335
```

```
His Lys Asp His Ile Ser Ala Tyr Gly Glu Gly Asn Glu Arg Arg Leu
            340                 345                 350

Thr Gly Lys His Glu Thr Ala Ser Ile Asn Thr Phe Ser Trp Gly Val
            355                 360                 365

Ala Asn Arg Gly Cys Ser Ile Arg Val Gly Arg Asp Thr Glu Lys Asn
        370                 375                 380

Gly Lys Gly Tyr Leu Glu Asp Arg Arg Pro Ala Ser Asn Met Asp Pro
385                 390                 395                 400

Tyr Val Val Thr Ser Leu Leu Ala Glu Thr Thr Leu Leu Trp Glu Pro
                405                 410                 415

Thr Leu Glu Ala Glu Ala Leu Ala Ala Gln Lys Leu Ala Leu Lys Val
            420                 425                 430

<210> SEQ ID NO 29
<211> LENGTH: 1556
<212> TYPE: DNA
<213> ORGANISM: Oryza sativa

<400> SEQUENCE: 29
accaccctcc ttgttacagc tgtgccgcct cttgcttcct cctcctcatc gtccgccatg    60
gcttctctca ccgatctcgt caacctcaac ctctccgaca ccacggagaa gatcatcgcc   120
gagtacatat ggatcggtgg atctggcatg gatctcagga gcaaggctag gactctctcc   180
ggccctgtga ctgatcccag caagctgccc aagtggaact acgatggctc cagcaccggc   240
caggcccccg gcgaggacag tgaggtcatc ctgtacccac aggctatctt caaggaccca   300
ttcaggaagg gaaacaacat ccttgtcatg tgcgattgct acacgccagc cggagaaccg   360
atccccacca acaagaggca caatgctgcc aagatcttca gctcccctga ggttgcttct   420
gaggagccct ggtacggtat tgagcaagag tacaccctcc tccagaagga catcaactgg   480
ccccttggct ggcctgttgg tggcttccct ggtcctcagg tccttacta ctgtggtatc   540 ggtgctgaca agtcttttgg gcgtgatatt gttgactccc actacaaggc ttgcctctat   600
gccggcatca acatcagtgg aatcaacggc gaggtcatgc caggacagtg ggagttccaa   660
gttggcccgt ctgtcggcat ttctgccggt gatcaggtgt gggttgctcg ctacattctt   720
gagaggatca ccgagatcgc cggagtcgtc gtctcatttg accccaagcc catcccggga   780
gactggaacg tgctggtgc tcacaccaac tacagcacca gtcgatgag gaacgatggt   840 ggctacgaga tcatcaagtc cgccattgag aagctcaagc tcaggcacaa ggagcacatc   900
tccgcctacg cgagggcaa cgagcgccgg ctcaccggca ggcacgagac cgccgacatc   960
aacaccttca gctggggagt tgccaaccgc ggcgcctcgg tccgcgtcgg ccgggagacg   1020
gagcagaacg gcaagggcta cttcgaggat cgccggccgg cgtccaacat ggacccttac   1080
atcgtcacct ccatgatcgc cgagaccacc atcatctgga agccctgaag cggcttcttg   1140
acgccacgac atcctcgtca tcgtcctccc cagctcgccg tgtcgctccg gttgctccat   1200
tgatcggacg atctggtgaa ttgcatttgt gctgggagaa gtaaaaaaaa aaggaaagag   1260
aaaaaaaaga aaatcacgcc aaaaaaaatt ctcattccat ttcgatttgg ttgcatgcta   1320
ccactactac tacattgctc atctgccatt tagattagct cctttttctt cgtcttttgg   1380
gtgagtgcgt ttgggtgctc ttgtgtaatc ctccaataat ggccgtacct acggtacttg   1440
tcccatcctg tggatcatcg tcctcctttc cacatgtggt tttatcatca ttgttattag   1500
tgatcacctt tatataaagt tcttgctggg cttccaatag ccgtggcttt tgcgtt       1556
```

-continued

```
<210> SEQ ID NO 30
<211> LENGTH: 356
<212> TYPE: PRT
<213> ORGANISM: Oryza sativa

<400> SEQUENCE: 30

Met Ala Ser Leu Thr Asp Leu Val Asn Leu Asn Leu Ser Asp Thr Thr
1               5                   10                  15

Glu Lys Ile Ile Ala Glu Tyr Ile Trp Ile Gly Gly Ser Gly Met Asp
            20                  25                  30

Leu Arg Ser Lys Ala Arg Thr Leu Ser Gly Pro Val Thr Asp Pro Ser
        35                  40                  45

Lys Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Lys Gly Asn Asn Ile Leu Val Met Cys Asp Cys Tyr Thr
                85                  90                  95

Pro Ala Gly Glu Pro Ile Pro Thr Asn Lys Arg His Asn Ala Ala Lys
            100                 105                 110

Ile Phe Ser Ser Pro Glu Val Ala Ser Glu Glu Pro Trp Tyr Gly Ile
        115                 120                 125

Glu Gln Glu Tyr Thr Leu Leu Gln Lys Asp Ile Asn Trp Pro Leu Gly
130                 135                 140

Trp Pro Val Gly Gly Phe Pro Gly Pro Gln Gly Pro Tyr Tyr Cys Gly
145                 150                 155                 160

Ile Gly Ala Asp Lys Ser Phe Gly Arg Asp Ile Val Asp Ser His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ala Gly Asp Gln Val Trp Val Ala Arg Tyr Ile Leu Glu Arg Ile
210                 215                 220

Thr Glu Ile Ala Gly Val Val Val Ser Phe Asp Pro Lys Pro Ile Pro
225                 230                 235                 240

Gly Asp Trp Asn Gly Ala Gly His Thr Asn Tyr Ser Thr Lys Ser
                245                 250                 255

Met Arg Asn Asp Gly Gly Tyr Glu Ile Ile Lys Ser Ala Ile Glu Lys
            260                 265                 270

Leu Lys Leu Arg His Lys Glu His Ile Ser Ala Tyr Gly Glu Gly Asn
        275                 280                 285

Glu Arg Arg Leu Thr Gly Arg His Glu Thr Ala Asp Ile Asn Thr Phe
290                 295                 300

Ser Trp Gly Val Ala Asn Arg Gly Ala Ser Val Arg Val Gly Arg Glu
305                 310                 315                 320

Thr Glu Gln Asn Gly Lys Gly Tyr Phe Glu Asp Arg Arg Pro Ala Ser
                325                 330                 335

Asn Met Asp Pro Tyr Ile Val Thr Ser Met Ile Ala Glu Thr Thr Ile
            340                 345                 350

Ile Trp Lys Pro
        355

<210> SEQ ID NO 31
```

```
<211> LENGTH: 1169
<212> TYPE: DNA
<213> ORGANISM: Oryza sativa

<400> SEQUENCE: 31
ttctacacct catttccgc ttgcatcttg ctcattcaga tctcttctgc tttgagcaat      60
ggccaacctc accgacctcg ttaacctcaa cctcagcgac tgcagcgaca agatcatcgc    120
cgagtacatc tgggttggag gatcgggcat agacctcagg agcaaagcga ggactgtgaa    180
aggccccatc accgatgtga gccagctgcc gaagtggaac tacgacggct ccagcaccgg    240
gcaggctccc ggcgaggaca gcgaagtgat cctctaccct caagccattt tcaaggaccc    300
gttcaggagg ggcgacaaca tccttgtgat gtgcgactgc tacacgccac aaggtgagcc    360
aatcccccact aacaagaggc acagtgccgc caagatcttc agccaccctg atgttgttgc    420
tgaggtgcca tggtacggta ttgagcagga gtacacactc cttcaaaagg atgtgaactg    480
gccccttggc tggccagttg gtggcttccc tggcccacag ggaccatact actgcgctgc    540
cggtgccgaa aaggcgttcg gccgcgacat cgtggacgcc cactacaagg cctgcatcta    600
cgccgggatc aacatcagtg gcatcaacgg ggaagtcatg cccggccagt gggagttcca    660
agttggcccg tcagttggca tcgccgctgc tgaccaagtg tgggttgccc gctacatcct    720
cgagagggtc acagaggtgg ccggagtcgt gctctcccctt gacccgaagc cgatcccggg    780
tgactggaat ggcgctggtg cccacaccaa cttcagcacc aagtcgatga gggagccggg    840
aggctacgag gtgatcaaga aggcgatcga caagctcgcg ctgaggcaca aggagcacat    900
cgccgcctac ggcgagggca cgagcgcgcc cctcaccggc cgccacgaga ccgccgacat    960
caacaccttc aaatggggcg tggcgaaccg cggcgcgtcc atccgcgtgg ggcgcgacac   1020
ggagaaggag ggcaaggggt acttcgagga caggaggccg gcgtccaaca tggacccata   1080
cgtcgtcacc ggcatgatcg ccgagaccac gctgctgtgg aagcagaact aagccgtccg   1140
gcgggcctct cccgtgcatt tctgcgccc                                      1169

<210> SEQ ID NO 32
<211> LENGTH: 357
<212> TYPE: PRT
<213> ORGANISM: Oryza sativa

<400> SEQUENCE: 32
```

Met Ala Asn Leu Thr Asp Leu Val Asn Leu Asn Ser Asp Cys Ser
1               5                   10                  15

Asp Lys Ile Ile Ala Glu Tyr Ile Trp Val Gly Gly Ser Gly Ile Asp
            20                  25                  30

Leu Arg Ser Lys Ala Arg Thr Val Lys Gly Pro Ile Thr Asp Val Ser
        35                  40                  45

Gln Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Arg Gly Asp Asn Ile Leu Val Met Cys Asp Cys Tyr Thr
                85                  90                  95

Pro Gln Gly Glu Pro Ile Pro Thr Asn Lys Arg His Ser Ala Ala Lys
            100                 105                 110

Ile Phe Ser His Pro Asp Val Val Ala Glu Val Pro Trp Tyr Gly Ile
        115                 120                 125

Glu Gln Glu Tyr Thr Leu Leu Gln Lys Asp Val Asn Trp Pro Leu Gly

```
                130                 135                 140
Trp Pro Val Gly Gly Phe Pro Gly Pro Gln Gly Pro Tyr Tyr Cys Ala
145                 150                 155                 160

Ala Gly Ala Glu Lys Ala Phe Gly Arg Asp Ile Val Asp Ala His Tyr
                165                 170                 175

Lys Ala Cys Ile Tyr Ala Gly Ile Asn Ile Ser Gly Ile Asn Gly Glu
                180                 185                 190

Val Met Pro Gly Gln Trp Glu Phe Gln Val Gly Pro Ser Val Gly Ile
                195                 200                 205

Ala Ala Ala Asp Gln Val Trp Val Ala Arg Tyr Ile Leu Glu Arg Val
            210                 215                 220

Thr Glu Val Ala Gly Val Val Leu Ser Leu Asp Pro Lys Pro Ile Pro
225                 230                 235                 240

Gly Asp Trp Asn Gly Ala Gly Ala His Thr Asn Phe Ser Thr Lys Ser
                245                 250                 255

Met Arg Glu Pro Gly Gly Tyr Glu Val Ile Lys Lys Ala Ile Asp Lys
                260                 265                 270

Leu Ala Leu Arg His Lys Glu His Ile Ala Ala Tyr Gly Glu Gly Asn
            275                 280                 285

Glu Arg Arg Leu Thr Gly Arg His Glu Thr Ala Asp Ile Asn Thr Phe
290                 295                 300

Lys Trp Gly Val Ala Asn Arg Gly Ala Ser Ile Arg Val Gly Arg Asp
305                 310                 315                 320

Thr Glu Lys Glu Gly Lys Gly Tyr Phe Glu Asp Arg Arg Pro Ala Ser
                325                 330                 335

Asn Met Asp Pro Tyr Val Val Thr Gly Met Ile Ala Glu Thr Thr Leu
                340                 345                 350

Leu Trp Lys Gln Asn
            355

<210> SEQ ID NO 33
<211> LENGTH: 1495
<212> TYPE: DNA
<213> ORGANISM: Oryza sativa

<400> SEQUENCE: 33
attgatagcc tgtgcgtctc caagaagagg cttgccgctg ccgccattgg agccctctcg    60
tttctgctcg agctctgcat ttcttcagta ggaggaggag gaggaagagt tggagtcgcc   120
atgtcgtcgt ccctgctcac tgacctcgtt aacctcgacc tgtcggagag cacggacaag   180
gtcatcgccg agtacatatg ggttggtggt actgggatgg atgtgaggag caaagccaga   240
acgttgtctg gacctgttga tgacccaagc aagcttccaa agtggaactt tgatggctcc   300
agcaccggtc aggctaccgg tgacgacagt gaagtcatcc tccaccctca agccatcttc   360
agagacccat tcaggaaggg gaagaacatc ctggtcatgt gtgactgtta tgcgccgaat   420
ggcgagccga ttccgacgaa caaccggtac aatgcagcaa ggatcttcag tcatcctgat   480
gtcaaggctg aagagccatg gtatgggatt gagcaggagt acacccttct tcagaagcac   540
atcaactggc tcttggctg ccactaggt ggctatccag gccctcaggg tccgtactac   600
tgtgcggcgg agccgataa atcgtacggg cgcgacatcg ttgatgccca ctacaaggcc   660
tgcctgtttg ccggcatcaa catcagcggg atcaacgcag aagtcatgcc ggggcagtgg   720
gagttccaga ttggcctgt cgttggcgtc tccgcagggg atcatgtctg ggtggcacgc   780
tacattcttg agaggatcac tgagattgct ggcgtcgtcg tgtccttcga ccccaagccc   840
```

-continued

```
attccgggag actggaatgg cgccggtgct cacaccaact acagcaccaa gtcgatgagg    900
agcaatggcg gctacgaggt gatcaagaaa gcgatcaaga agcttggcat gcgccaccgt    960
gagcacatcg ccgcctacgg cgacggcaac gagcgccgcc tcaccggccg ccacgagacc   1020
gccgacatca caacttcgt ctgggcgta gcgaaccgcg gcgcgtcggt gcgtgtcggc     1080
cgggacaccg agaaggacgg caaaggttac ttcgaggaca ggaggccggc gtccaacatg   1140
gacccgtacc tggtgaccgc catgatcgcc gagaccacca tcctctggga gcccagccac   1200
ggccacggcc acggccaatc caacggcaag tgaggaggag tcgcctcgcc cgggttgatg   1260
aactgctttc tcgcgttctg ggtttcatgg aaatctgtgt gtgtgtgttc tctgacgctg   1320
gtgctgttag aaacttccaa taattcagaa ataactgcga tgtgctctca aatttctcat   1380
gaggccatca cctgcagcat ctcatgaaat agatctattg caatgacaat accaatggca   1440
acgcaaaatt ttatggtacc tccagatacc atctactctc ctcaataatg acaat        1495
```

<210> SEQ ID NO 34
<211> LENGTH: 370
<212> TYPE: PRT
<213> ORGANISM: Oryza sativa

<400> SEQUENCE: 34

```
Met Ser Ser Ser Leu Leu Thr Asp Leu Val Asn Leu Asp Leu Ser Glu
1               5                   10                  15

Ser Thr Asp Lys Val Ile Ala Glu Tyr Ile Trp Val Gly Gly Thr Gly
            20                  25                  30

Met Asp Val Arg Ser Lys Ala Arg Thr Leu Ser Gly Pro Val Asp Asp
        35                  40                  45

Pro Ser Lys Leu Pro Lys Trp Asn Phe Asp Gly Ser Ser Thr Gly Gln
    50                  55                  60

Ala Thr Gly Asp Asp Ser Glu Val Ile Leu His Pro Gln Ala Ile Phe
65                  70                  75                  80

Arg Asp Pro Phe Arg Lys Gly Lys Asn Ile Leu Val Met Cys Asp Cys
                85                  90                  95

Tyr Ala Pro Asn Gly Glu Pro Ile Pro Thr Asn Asn Arg Tyr Asn Ala
            100                 105                 110

Ala Arg Ile Phe Ser His Pro Asp Val Lys Ala Glu Glu Pro Trp Tyr
        115                 120                 125

Gly Ile Glu Gln Glu Tyr Thr Leu Leu Gln Lys His Ile Asn Trp Pro
    130                 135                 140

Leu Gly Trp Pro Leu Gly Gly Tyr Pro Gly Pro Gln Gly Pro Tyr Tyr
145                 150                 155                 160

Cys Ala Ala Gly Ala Asp Lys Ser Tyr Gly Arg Asp Ile Val Asp Ala
                165                 170                 175

His Tyr Lys Ala Cys Leu Phe Ala Gly Ile Asn Ile Ser Gly Ile Asn
            180                 185                 190

Ala Glu Val Met Pro Gly Gln Trp Glu Phe Gln Ile Gly Pro Val Val
        195                 200                 205

Gly Val Ser Ala Gly Asp His Val Trp Val Ala Arg Tyr Ile Leu Glu
    210                 215                 220

Arg Ile Thr Glu Ile Ala Gly Val Val Val Ser Phe Asp Pro Lys Pro
225                 230                 235                 240

Ile Pro Gly Asp Trp Asn Gly Ala Gly Ala His Thr Asn Tyr Ser Thr
                245                 250                 255
```

```
Lys Ser Met Arg Ser Asn Gly Gly Tyr Glu Val Ile Lys Lys Ala Ile
            260                 265                 270

Lys Lys Leu Gly Met Arg His Arg Glu His Ile Ala Ala Tyr Gly Asp
        275                 280                 285

Gly Asn Glu Arg Arg Leu Thr Gly Arg His Glu Thr Ala Asp Ile Asn
    290                 295                 300

Asn Phe Val Trp Gly Val Ala Asn Arg Gly Ala Ser Val Arg Val Gly
305                 310                 315                 320

Arg Asp Thr Glu Lys Asp Gly Lys Gly Tyr Phe Glu Arg Arg Pro
                325                 330                 335

Ala Ser Asn Met Asp Pro Tyr Leu Val Thr Ala Met Ile Ala Glu Thr
            340                 345                 350

Thr Ile Leu Trp Glu Pro Ser His Gly His Gly His Gly Gln Ser Asn
        355                 360                 365

Gly Lys
    370

<210> SEQ ID NO 35
<211> LENGTH: 1677
<212> TYPE: DNA
<213> ORGANISM: Oryza sativa

<400> SEQUENCE: 35
atcgacgtcg cctcctctcc tcctcctcct cgtcgctgca ttccggttga gtgagttggt      60
gattatctgt aggggggtgaa atggcgcag gcggtggtgc cggcgatgca gtgccaggtc     120
ggggccgtgc gggcgaggcc ggcggcggct cggcggcgg cggggggag ggtgtgggga      180 gtcaggagga ccgggcgcgg cacgtcgggg ttcaggtga tggccgtgag cacggagacc     240
accgggtgtg tgacgcggat ggagcagctg ctcaacatgg acaccacccc cttcaccgac     300
aagatcatcg ccgagtacat ctgggttgga ggaactggaa ttgacctcag aagcaaatca     360
aggacaatat caaaaccagt ggaggacccc tcggagctac aaaatggaa ctacgatgga     420 tcaagcacag ggcaagctcc aggagaagat agtgaagtca tcttataccc acaggctata     480
ttcaaggacc catttcgagg tggcaacaac atattggtta tgtgtgatac ctacacacca     540
gctggggaac ccatccctac taacaaacgt aacagggctg cacaagtatt cagtgatcca     600
aaggttgtca gccaagtgcc atggtttgga atagaacagg agtacacttt gctccagaga     660
gacgtaaact ggcctcttgg ctggcccgtt ggaggctacc ctgggcccca gggtccatac     720
tactgcgctg taggatcgga caaatcgttt ggccgtgaca tatcagatgc tcactacaag     780
gcatgtcttt atgctggaat taacattagt ggaacaaatg gagaggtcat gcctggtcag     840
tgggagtacc aggttggacc tagtgtcggt attgaagctg agaccacat atggatttca     900 agatatattc ttgagagaat aacggagcag gctggtgtag tgcttaccct tgaccccaaa     960
ccaattcagg gagactggaa tggagctggg tgccacacaa actacagcac caagagtatg    1020
cgtgaagatg gaggatttga ggtgatcaag aaggcaatcc taaacctatc acttcgccat    1080
gacttgcata agtgcata tggtgaagga atgaaagga ggttgacagg tttacacgag      1140
acagctagca ttgacaattt ctcatggggt gtggcaaacc gtggatgctc tattcgggtg    1200
gggcgagaca ccgaggcgaa gggaaaaggc tacttggaag accgtcgccc ggcatcaaac    1260
atggacccgt acgtcgtgac agcgctattg gctgaaacca caattctttg ggagccaacc    1320
ctcgaagcga aggttcttgc tgctaagaag ttggccctga aggtatgaag aacttggacg    1380
atgaatcggg gcaaataaat cccagcaaaa tttgtttgct gcccaccagt cttgatcttg    1440
```

-continued

```
tatttcttct gtctggggat tggtctgtac aaatctgcag tttctagaaa accacgccac   1500
cttccattcg ccagttaaca ttttggttga acaccacact tgatctgggt ctgtattttg   1560
agtccatttg tgagtgacag aacggatgat gaaacacatc agggacactt ttaagtttct   1620
tcagtcctgc gtccttccct cgaaataaaa atgtttcctt gttttttatc ccgggct      1677
```

<210> SEQ ID NO 36
<211> LENGTH: 428
<212> TYPE: PRT
<213> ORGANISM: Oryza sativa

<400> SEQUENCE: 36

```
Met Ala Gln Ala Val Val Pro Ala Met Gln Cys Gln Val Gly Ala Val
1               5                   10                  15

Arg Ala Arg Pro Ala Ala Ala Ala Ala Gly Gly Arg Val Trp
            20                  25                  30

Gly Val Arg Arg Thr Gly Arg Gly Thr Ser Gly Phe Arg Val Met Ala
            35                  40                  45

Val Ser Thr Glu Thr Thr Gly Val Val Thr Arg Met Glu Gln Leu Leu
    50                  55                  60

Asn Met Asp Thr Thr Pro Phe Thr Asp Lys Ile Ile Ala Glu Tyr Ile
65                  70                  75                  80

Trp Val Gly Gly Thr Gly Ile Asp Leu Arg Ser Lys Ser Arg Thr Ile
                85                  90                  95

Ser Lys Pro Val Glu Asp Pro Ser Glu Leu Pro Lys Trp Asn Tyr Asp
            100                 105                 110

Gly Ser Ser Thr Gly Gln Ala Pro Gly Glu Asp Ser Glu Val Ile Leu
        115                 120                 125

Tyr Pro Gln Ala Ile Phe Lys Asp Pro Phe Arg Gly Gly Asn Asn Ile
    130                 135                 140

Leu Val Met Cys Asp Thr Tyr Thr Pro Ala Gly Glu Pro Ile Pro Thr
145                 150                 155                 160

Asn Lys Arg Asn Arg Ala Ala Gln Val Phe Ser Asp Pro Lys Val Val
                165                 170                 175

Ser Gln Val Pro Trp Phe Gly Ile Glu Gln Glu Tyr Thr Leu Leu Gln
            180                 185                 190

Arg Asp Val Asn Trp Pro Leu Gly Trp Pro Val Gly Gly Tyr Pro Gly
        195                 200                 205

Pro Gln Gly Pro Tyr Tyr Cys Ala Val Gly Ser Asp Lys Ser Phe Gly
    210                 215                 220

Arg Asp Ile Ser Asp Ala His Tyr Lys Ala Cys Leu Tyr Ala Gly Ile
225                 230                 235                 240

Asn Ile Ser Gly Thr Asn Gly Glu Val Met Pro Gly Gln Trp Glu Tyr
                245                 250                 255

Gln Val Gly Pro Ser Val Gly Ile Glu Ala Gly Asp His Ile Trp Ile
            260                 265                 270

Ser Arg Tyr Ile Leu Glu Arg Ile Thr Glu Gln Ala Gly Val Val Leu
        275                 280                 285

Thr Leu Asp Pro Lys Pro Ile Gln Gly Asp Trp Asn Gly Ala Gly Cys
    290                 295                 300

His Thr Asn Tyr Ser Thr Lys Ser Met Arg Glu Asp Gly Gly Phe Glu
305                 310                 315                 320

Val Ile Lys Lys Ala Ile Leu Asn Leu Ser Leu Arg His Asp Leu His
                325                 330                 335
```

Ile Ser Ala Tyr Gly Glu Gly Asn Glu Arg Arg Leu Thr Gly Leu His
            340                 345                 350

Glu Thr Ala Ser Ile Asp Asn Phe Ser Trp Gly Val Ala Asn Arg Gly
            355                 360                 365

Cys Ser Ile Arg Val Gly Arg Asp Thr Glu Ala Lys Gly Lys Gly Tyr
            370                 375                 380

Leu Glu Asp Arg Arg Pro Ala Ser Asn Met Asp Pro Tyr Val Val Thr
385                 390                 395                 400

Ala Leu Leu Ala Glu Thr Thr Ile Leu Trp Glu Pro Thr Leu Glu Ala
            405                 410                 415

Glu Val Leu Ala Ala Lys Lys Leu Ala Leu Lys Val
            420                 425

<210> SEQ ID NO 37
<211> LENGTH: 774
<212> TYPE: DNA
<213> ORGANISM: Sorghum bicolor

<400> SEQUENCE: 37
atggccagcc tcaccgatct cgttaaccte gacctgagtg attgcaccga caagatcatt      60
gccgagtaca tctggattgg aggatccggc atagacctca ggagcaaagc aaggacggtg     120
aaaggcccca tcaccgatcc gagccagctg ccaaaatgga actacgacgg ctccagcacc     180
gggcaggctc ccggagagga cagcgaagtc atcctctacc ctcaagccat tttcaaggac     240
ccgttcagga agggcgacaa catccttgtg atgtgtgact gctacacgcc acaaggcgag     300
ccaatcccta ctaacaagag gtacaatgct gccaaggttt tcagccaccc cgacgttgca     360
gctgaggtgc catggtacgg tattgagcag gagtacactc tccttcagaa ggatgtgaac     420
tggccccttg gctggcctgt tggtggatac cctggtcccc agggaccata ctactgcgct     480
gccggtgccg ataaggcctt tgggcgcgat gtggtcgacg cccactacaa agcctgcctc     540
tacgccggca tcaacatcag cggcatcaac ggcgaagtca tgcctggcca gtgggagttc     600
caagttggcc cgtccgttgg gatatctgcc ggtgacgaaa tatgggttgc ccgctacatt     660
ctcgagaggg agggcaaggg atacttcgag gaccgcaggc cggcatccaa catggacccc     720
tacgtcgtca ccggcatgat cgccgagacc accatcctgt ggaacggaaa ctga           774

<210> SEQ ID NO 38
<211> LENGTH: 357
<212> TYPE: PRT
<213> ORGANISM: Sorghum bicolor

<400> SEQUENCE: 38

Met Ala Ser Leu Thr Asp Leu Val Asn Leu Asp Leu Ser Asp Cys Thr
1               5                   10                  15

Asp Lys Ile Ile Ala Glu Tyr Ile Trp Ile Gly Gly Ser Gly Ile Asp
            20                  25                  30

Leu Arg Ser Lys Ala Arg Thr Val Lys Gly Pro Ile Thr Asp Pro Ser
        35                  40                  45

Gln Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Lys Gly Asp Asn Ile Leu Val Met Cys Asp Cys Tyr Thr
                85                  90                  95

```
Pro Gln Gly Glu Pro Ile Pro Thr Asn Lys Arg Tyr Asn Ala Ala Lys
                100                 105                 110
Val Phe Ser His Pro Asp Val Ala Ala Glu Val Pro Trp Tyr Gly Ile
            115                 120                 125
Glu Gln Glu Tyr Thr Leu Leu Gln Lys Asp Val Asn Trp Pro Leu Gly
        130                 135                 140
Trp Pro Val Gly Gly Tyr Pro Gly Pro Gln Gly Pro Tyr Tyr Cys Ala
145                 150                 155                 160
Ala Gly Ala Asp Lys Ala Phe Gly Arg Asp Val Asp Ala His Tyr
                165                 170                 175
Lys Ala Cys Leu Tyr Ala Gly Ile Asn Ile Ser Gly Ile Asn Gly Glu
            180                 185                 190
Val Met Pro Gly Gln Trp Glu Phe Gln Val Gly Pro Ser Val Gly Ile
        195                 200                 205
Ser Ala Gly Asp Glu Ile Trp Val Ala Arg Tyr Ile Leu Glu Arg Ile
    210                 215                 220
Thr Glu Ile Ala Gly Ile Val Leu Ser Leu Asp Pro Lys Pro Ile Gln
225                 230                 235                 240
Gly Asp Trp Asn Gly Ala Gly Ala His Thr Asn Tyr Ser Thr Lys Ser
                245                 250                 255
Met Arg Glu Ala Gly Gly Tyr Glu Val Ile Lys Lys Ala Ile Glu Lys
            260                 265                 270
Leu Gly Lys Arg His Thr Glu His Ile Ala Ala Tyr Gly Glu Gly Asn
        275                 280                 285
Glu Arg Arg Leu Thr Gly Arg His Glu Thr Ala Asp Ile Asn Thr Phe
    290                 295                 300
Lys Trp Gly Val Ala Asn Arg Gly Ala Ser Ile Arg Val Gly Arg Asp
305                 310                 315                 320
Thr Glu Arg Glu Gly Lys Gly Tyr Phe Glu Asp Arg Arg Pro Ala Ser
                325                 330                 335
Asn Met Asp Pro Tyr Val Val Thr Gly Met Ile Ala Glu Thr Thr Ile
            340                 345                 350
Leu Trp Asn Gly Asn
        355

<210> SEQ ID NO 39
<211> LENGTH: 1068
<212> TYPE: DNA
<213> ORGANISM: Sorghum bicolor

<400> SEQUENCE: 39
atggcctccc tcaccgacct cgtcaacctc agcctctcgg acaccaccga gaagatcatc      60
gccgagtaca tatggatcgg tggatctggc atggatctca ggagcaaagc caggacccta     120
tccggcccgg tgaccgatcc cagcaagctg cccaagtgga actacgacgg ctccagcacc     180
ggccaggccc ccggcgagga cagtgaggtc atcctcccgc aggctatctt caaggaccca     240
ttccggaggg gcaacaacat ccttgtcatg tgcgattgct acacccccag ctggcgagcca    300 attcccacca caagaggca caacgccgcc aagatcttca gcaaccctga ggtcgctgct      360
gaggagccct ggtacggtat tgagcaggag tacacccctcc ttcagaagga caccaactgg     420 cccctttgggt ggcctcttgg tggcttccct ggccctcagg gtccttacta ctgtggaatc     480
ggtgcggaca gtcattcgg gcgtgacata gttgatgccc actacaaggc ttgcattttat     540 gcaggcatca acatcagtgg catcaacgga gaggtcatgc cagggcagtg ggaattccaa     600
```

```
gttggaccgt ccgtcggcat ttcttcaggt gatcaggtct gggttgctcg ctacattctt    660
gagaggatca ccgagatcgc cggtgtggtg ttgacattcg acccaaagcc catccctggt    720
gactggaacg gtgccggcgc acacaccaac tacagcacca agtccatgag gaacgagggc    780
gggtacgagg tgatcaaggc cgccattgag aagctgaagt tgcggcacaa ggagcacatc    840
gcggcctacg gcgagggcaa cgagcgccgc ctcaccggca ggcacgagac cgccgacatc    900
aacaccttca gctggggagt ggcaaaccgt ggcgcgtcag tgcgcgtggg ccgggagacg    960
gagcagaacg gcaagggcta cttcgaggac cgccggccgg cgtccaacat ggacccatac   1020
gtggtgacct ccatgatcgc cgacaccacc atcctctgga agccctga                1068
```

<210> SEQ ID NO 40
<211> LENGTH: 355
<212> TYPE: PRT
<213> ORGANISM: Sorghum bicolor

<400> SEQUENCE: 40

```
Met Ala Ser Leu Thr Asp Leu Val Asn Leu Ser Leu Ser Asp Thr Thr
1               5                   10                  15

Glu Lys Ile Ile Ala Glu Tyr Ile Trp Ile Gly Gly Ser Gly Met Asp
            20                  25                  30

Leu Arg Ser Lys Ala Arg Thr Leu Ser Gly Pro Val Thr Asp Pro Ser
        35                  40                  45

Lys Leu Pro Lys Trp Asn Tyr Asp Gly Ser Ser Thr Gly Gln Ala Pro
    50                  55                  60

Gly Glu Asp Ser Glu Val Ile Leu Pro Gln Ala Ile Phe Lys Asp Pro
65                  70                  75                  80

Phe Arg Arg Gly Asn Asn Ile Leu Val Met Cys Asp Cys Tyr Thr Pro
                85                  90                  95

Ala Gly Glu Pro Ile Pro Thr Asn Lys Arg His Asn Ala Ala Lys Ile
            100                 105                 110

Phe Ser Asn Pro Glu Val Ala Ala Glu Glu Pro Trp Tyr Gly Ile Glu
        115                 120                 125

Gln Glu Tyr Thr Leu Leu Gln Lys Asp Thr Asn Trp Pro Leu Gly Trp
    130                 135                 140

Pro Leu Gly Gly Phe Pro Gly Pro Gln Gly Pro Tyr Tyr Cys Gly Ile
145                 150                 155                 160

Gly Ala Asp Lys Ser Phe Gly Arg Asp Ile Val Asp Ala His Tyr Lys
                165                 170                 175

Ala Cys Ile Tyr Ala Gly Ile Asn Ile Ser Gly Ile Asn Gly Glu Val
            180                 185                 190

Met Pro Gly Gln Trp Glu Phe Gln Val Gly Pro Ser Val Gly Ile Ser
        195                 200                 205

Ser Gly Asp Gln Val Trp Val Ala Arg Tyr Ile Leu Glu Arg Ile Thr
    210                 215                 220

Glu Ile Ala Gly Val Val Leu Thr Phe Asp Pro Lys Pro Ile Pro Gly
225                 230                 235                 240

Asp Trp Asn Gly Ala Gly Ala His Thr Asn Tyr Ser Thr Lys Ser Met
                245                 250                 255

Arg Asn Glu Gly Gly Tyr Glu Val Ile Lys Ala Ala Ile Glu Lys Leu
            260                 265                 270

Lys Leu Arg His Lys Glu His Ile Ala Ala Tyr Gly Glu Gly Asn Glu
        275                 280                 285

Arg Arg Leu Thr Gly Arg His Glu Thr Ala Asp Ile Asn Thr Phe Ser
```

```
            290                 295                 300
Trp Gly Val Ala Asn Arg Gly Ala Ser Val Arg Val Gly Arg Glu Thr
305                 310                 315                 320

Glu Gln Asn Gly Lys Gly Tyr Phe Glu Asp Arg Arg Pro Ala Ser Asn
                325                 330                 335

Met Asp Pro Tyr Val Val Thr Ser Met Ile Ala Asp Thr Thr Ile Leu
            340                 345                 350

Trp Lys Pro
        355

<210> SEQ ID NO 41
<211> LENGTH: 1158
<212> TYPE: DNA
<213> ORGANISM: Sorghum bicolor

<400> SEQUENCE: 41
atggcggcgc aggcggtggt gccggcgatg cagtgccagg tcggagtgaa ggcggcggcg      60
ggcgcccggg cgaggccggc ggcggcggga ggcagggtgt ggggcgtcag gagtaggacc     120
ggccgcggcg cgcctcgcc ggggttcaag gtcatggccg tcagcacggg cagcaccggg      180
gtggtgccac gcctggagca gctgctcaac atggacacca cgcctacac cgacaagatc      240 atcgccgagt acatctgccc ccaggctatc ttcaaggacc cattccgagg tggcaacaac     300
attttggtta tctgtgatac ctacacgcca cagggtgaac ccttcctac taacaaacgg      360 cacagggctg cgcaaatttt tagtgaccca aggtcgttg aacaagtgcc atggtttggc      420
atagagcaag agtacacttt gctccagaaa gatgtgaatt ggcctcttgg ttggcctgtt     480
ggaggctacc ctggtcccca gggtccctac tactgtgctg taggagcaga caaatcattt     540
ggccgtgaca tatcagatgc tcactacaag gcttgccttt atgctggaat taacattagt     600
ggaacaaacg gggaggtcat gcctggtcag tgggagtacc aagttggacc tagtgttggc     660
attgaagcag agatcacat atggatttca agatacattc tcgagagaat cacagagcaa     720
gctggggttg tccttaccct tgatccaaaa ccaattcagg gtgactggaa tggagctggc     780
tgccacacaa attacagcac aaagaccatg cgtgaagatg gaggatttga agatatcaag     840
agagcaatcc tgaatctttc tctgcgccat gatttgcata ttagtgcata cggagaagga     900
aatgaaagaa gattgacagg gaagcatgag accgctagca tcgagacctt ctcatgggt      960 gtggcaaacc gtggctgctc tgttcgtgtg gggcgagata ccgaggcaaa agggaaggt     1020 tacctagaag accgtcgccc ggcatcaaac atggacccat acattgtgac ggggctactg    1080
gctgaaacaa caattctctg gcaaccaacc cttgaagcgg aggttcttgc cgccaagaag    1140
ctggcgctga aggtatga                                                 1158

<210> SEQ ID NO 42
<211> LENGTH: 385
<212> TYPE: PRT
<213> ORGANISM: Sorghum bicolor

<400> SEQUENCE: 42

Met Ala Ala Gln Ala Val Val Pro Ala Met Gln Cys Gln Val Gly Val
1               5                   10                  15

Lys Ala Ala Ala Gly Ala Arg Ala Arg Pro Ala Ala Ala Gly Gly Arg
            20                  25                  30

Val Trp Gly Val Arg Ser Arg Thr Gly Arg Gly Gly Ala Ser Pro Gly
        35                  40                  45
```

```
Phe Lys Val Met Ala Val Ser Thr Gly Ser Thr Gly Val Val Pro Arg
 50                  55                  60

Leu Glu Gln Leu Leu Asn Met Asp Thr Thr Pro Tyr Thr Asp Lys Ile
 65                  70                  75                  80

Ile Ala Glu Tyr Ile Cys Pro Gln Ala Ile Phe Lys Asp Pro Phe Arg
                 85                  90                  95

Gly Gly Asn Asn Ile Leu Val Ile Cys Asp Thr Tyr Thr Pro Gln Gly
            100                 105                 110

Glu Pro Leu Pro Thr Asn Lys Arg His Arg Ala Ala Gln Ile Phe Ser
            115                 120                 125

Asp Pro Lys Val Val Glu Gln Val Pro Trp Phe Gly Ile Glu Gln Glu
130                 135                 140

Tyr Thr Leu Leu Gln Lys Asp Val Asn Trp Pro Leu Gly Trp Pro Val
145                 150                 155                 160

Gly Gly Tyr Pro Gly Pro Gln Gly Pro Tyr Tyr Cys Ala Val Gly Ala
                165                 170                 175

Asp Lys Ser Phe Gly Arg Asp Ile Ser Asp Ala His Tyr Lys Ala Cys
            180                 185                 190

Leu Tyr Ala Gly Ile Asn Ile Ser Gly Thr Asn Gly Glu Val Met Pro
            195                 200                 205

Gly Gln Trp Glu Tyr Gln Val Gly Pro Ser Val Gly Ile Glu Ala Gly
210                 215                 220

Asp His Ile Trp Ile Ser Arg Tyr Ile Leu Glu Arg Ile Thr Glu Gln
225                 230                 235                 240

Ala Gly Val Val Leu Thr Leu Asp Pro Lys Pro Ile Gln Gly Asp Trp
                245                 250                 255

Asn Gly Ala Gly Cys His Thr Asn Tyr Ser Thr Lys Thr Met Arg Glu
            260                 265                 270

Asp Gly Gly Phe Glu Asp Ile Lys Arg Ala Ile Leu Asn Leu Ser Leu
            275                 280                 285

Arg His Asp Leu His Ile Ser Ala Tyr Gly Glu Gly Asn Glu Arg Arg
290                 295                 300

Leu Thr Gly Lys His Glu Thr Ala Ser Ile Glu Thr Phe Ser Trp Gly
305                 310                 315                 320

Val Ala Asn Arg Gly Cys Ser Val Arg Val Gly Arg Asp Thr Glu Ala
                325                 330                 335

Lys Gly Lys Gly Tyr Leu Glu Asp Arg Arg Pro Ala Ser Asn Met Asp
            340                 345                 350

Pro Tyr Ile Val Thr Gly Leu Leu Ala Glu Thr Thr Ile Leu Trp Gln
            355                 360                 365

Pro Thr Leu Glu Ala Glu Val Leu Ala Ala Lys Lys Leu Ala Leu Lys
370                 375                 380

Val
385

<210> SEQ ID NO 43
<211> LENGTH: 1359
<212> TYPE: DNA
<213> ORGANISM: Zea mays

<400> SEQUENCE: 43
gcccgagtga tggccagcct caccgacctc gtcaacctcg acctgagtga ctgcaccgac      60
aggatcatcg ccgagtacat ctggattgga ggaaccggga tagacctcag gagcaaagcg     120
aggacggtga aaggccccat caccgacccg atccagctgc cgaaatggaa ctacgacggc     180
```

-continued

```
tccagcaccg ggcaggctcc cggagaggac agcgaagtca tcctctaccc tcaagccatt      240
ttcaaggacc cgttcaggaa gggtaaccac atccttgtga tgtgtgactg ctacacgcca      300
caaggcgagc caatccccac caacaagagg tacagcgccg ccaaggtttt cagccacccc      360
gacgtcgcag ctgaggtgcc gtggtacggt attgagcagg agtacaccct ccttcagaag      420
gacgtgagct ggcccctcgg ctggcccgtt ggtggatacc ctggtcccca gggaccatac      480
tactgcgccg ccgtgccgga caaggccttt gggcgcgacg tggttgacgc ccactacaag      540
gcctgcctct acgccggcat caacatcagc ggcatcaacg gcgaagtcat gcctggacag      600
tgggagttcc aagtggggcc gtccgttggg atctctgccg gcgacgagat atgggtcgcc      660
cgctacattc tcgagaggat caccgagatg gccggaatcg tcctctccct cgacccgaag      720
ccgatcaagg gcgactggaa cggcgccggc gcccacacca actacagcac caagtcgatg      780
agggaggccg ggggatacga ggtcatcaag gcggcgatcg acaagctggg gaagaggcac      840
aaggagcaca tcgccgcgta cggcgagggc aacgagcgcc gcctcacggg ccgccacgag      900
accgccgaca tcaacaccct caaatggggc gtggcgaacc gcggcgcgtc catccgcgtc      960
ggccgcgaca ccgagaggga gggcaagggc tacttcgagg accgcaggcc ggcgtccaac     1020
atggacccct acgtcgtcac cggcatgatc gccgagacca ccatcctgtg gaatggaaac     1080
tgatcaagca tgtgcattct cgagggagcc cactgttttt cttctgcaca acgcatccgc     1140
cgtggtgtcg ctttggtttt gaaatttaga ttccgttgtc ctaaaattta tcactacggt     1200
ctccagtgta ttgctcggga acgaatgaat aacgactgcg atgtttgttt ttttttttgc     1260
tggcgtagta gatgtacgtt tggctgtgct tccagtttat tgggtaaatg aaaaaatgta     1320
atggtctacc ggtcttaaaa tagtagtcat tttagctct                            1359
```

<210> SEQ ID NO 44
<211> LENGTH: 357
<212> TYPE: PRT
<213> ORGANISM: Zea mays

<400> SEQUENCE: 44

```
Met Ala Ser Leu Thr Asp Leu Val Asn Leu Asp Leu Ser Asp Cys Thr
1               5                   10                  15

Asp Arg Ile Ile Ala Glu Tyr Ile Trp Ile Gly Gly Thr Gly Ile Asp
            20                  25                  30

Leu Arg Ser Lys Ala Arg Thr Val Lys Gly Pro Ile Thr Asp Pro Ile
        35                  40                  45

Gln Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Lys Gly Asn His Ile Leu Val Met Cys Asp Cys Tyr Thr
                85                  90                  95

Pro Gln Gly Glu Pro Ile Pro Thr Asn Lys Arg Tyr Ser Ala Ala Lys
            100                 105                 110

Val Phe Ser His Pro Asp Val Ala Ala Glu Val Pro Trp Tyr Gly Ile
        115                 120                 125

Glu Gln Glu Tyr Thr Leu Leu Gln Lys Asp Val Ser Trp Pro Leu Gly
    130                 135                 140

Trp Pro Val Gly Gly Tyr Pro Gly Pro Gln Gly Pro Tyr Tyr Cys Ala
145                 150                 155                 160
```

```
Ala Gly Ala Asp Lys Ala Phe Gly Arg Asp Val Val Asp Ala His Tyr
                165                 170                 175
Lys Ala Cys Leu Tyr Ala Gly Ile Asn Ile Ser Gly Ile Asn Gly Glu
            180                 185                 190
Val Met Pro Gly Gln Trp Glu Phe Gln Val Gly Pro Ser Val Gly Ile
        195                 200                 205
Ser Ala Gly Asp Glu Ile Trp Val Ala Arg Tyr Ile Leu Glu Arg Ile
    210                 215                 220
Thr Glu Met Ala Gly Ile Val Leu Ser Leu Asp Pro Lys Pro Ile Lys
225                 230                 235                 240
Gly Asp Trp Asn Gly Ala Gly Ala His Thr Asn Tyr Ser Thr Lys Ser
                245                 250                 255
Met Arg Glu Ala Gly Gly Tyr Glu Val Ile Lys Ala Ala Ile Asp Lys
            260                 265                 270
Leu Gly Lys Arg His Lys Glu His Ile Ala Ala Tyr Gly Glu Gly Asn
        275                 280                 285
Glu Arg Arg Leu Thr Gly Arg His Glu Thr Ala Asp Ile Asn Thr Phe
    290                 295                 300
Lys Trp Gly Val Ala Asn Arg Gly Ala Ser Ile Arg Val Gly Arg Asp
305                 310                 315                 320
Thr Glu Arg Glu Gly Lys Gly Tyr Phe Glu Asp Arg Arg Pro Ala Ser
                325                 330                 335
Asn Met Asp Pro Tyr Val Val Thr Gly Met Ile Ala Glu Thr Thr Ile
            340                 345                 350
Leu Trp Asn Gly Asn
        355
```

<210> SEQ ID NO 45
<211> LENGTH: 1369
<212> TYPE: DNA
<213> ORGANISM: Zea mays

<400> SEQUENCE: 45

```
cgaaagcaca cacgatcaa tcacactcac tcgcggccat tgtcctgccc gtgcgtgctc      60
tgccttttca ggcgatcgac caaccaactt ctcgtcactg ccatggctct gctctccgac    120
ctcatcaacc tcgacctctc gggccgcacc gggaagatca tcgccgagta catctgggtt    180
ggcggttccg ggatggacgt caggagcaaa gccaggacgc tgtccggacc tgttgatgac    240
cccagcaagc ttccgaagtg gaacttcgac ggctccagca ccggccaagc tccgggcgac    300
gacagcgaag tcatcctttg ccctcgggcc atcttcaggg acccgttcag gaaggggcag    360
aacatactgg tcatgtgcga ctgctacgag ccgaacgggg agccgatccc gagcaacaag    420
cggcatgggg ccgcgaagat ctttagccac cctgacgtca aggctgagga accatggttc    480
gggattgagc aggagtacac ccttctccag aaggacacca gtggcctct  cggttggccg    540
ctggcgtacc ctggccctca gggacccttac tactgcgccg ccgagcgga  caagtcctac    600
gggcgggaca tcgtggactg cgcatacaag gcctgcctct acgccggcat cgacatcagt    660
ggcatcaacg gggaggtcat gccgggggcag tgggagttcc aggtggcccc tgccgtcggc    720
gtctcggccg gcgaccagct ctgggtggct cgctacattc ttgagaggat caccgagatc    780
gccggcgtgg ttgtctcct  cgaccccaag ccaattccgg gggactggaa tggcgctggt    840
gcacacacca actacagcac caagtcgatg aggagcgacg gcgggtacga ggtgatcaag    900
aaggcgatcg gcaagctggg cctccggcac cgggagcaca tcgccgcgta cggggacggc    960
```

```
aacgagcgcc cgctcaccgg ccgccacgag accgccgaca tcaacaccttt cgtctggggc   1020 gtgccgaacc gcggggcgtc ggtgcgggtg ggccgagaca ccgagaagga aggcaaaggc   1080
tacttcgagg accggaggcc ggcgtccaac atggacccgt acgtggtgac ctgcctgatc   1140
gcggagacaa ccatgctgtg ggagcccagc cactccaacg cgacggcaa gggcgccgcg   1200 gctccttgat ttgattctgc ggagactgag ctctgtgtgt gagccggcct gcgtagatgg   1260
caaatgggac tgaccctgtc agaaacttga gatgaccata ataatagctg cagtgtgctc   1320
gttctggggt tggataagac ccaagaactt tttttagctt tcttcgaac               1369
```

<210> SEQ ID NO 46
<211> LENGTH: 368
<212> TYPE: PRT
<213> ORGANISM: Zea mays

<400> SEQUENCE: 46

```
Met Ala Leu Leu Ser Asp Leu Ile Asn Leu Asp Leu Ser Gly Arg Thr
1               5                   10                  15

Gly Lys Ile Ile Ala Glu Tyr Ile Trp Val Gly Ser Gly Met Asp
            20                  25                  30

Val Arg Ser Lys Ala Arg Thr Leu Ser Gly Pro Val Asp Asp Pro Ser
        35                  40                  45

Lys Leu Pro Lys Trp Asn Phe Asp Gly Ser Ser Thr Gly Gln Ala Pro
    50                  55                  60

Gly Asp Asp Ser Glu Val Ile Leu Cys Pro Arg Ala Ile Phe Arg Asp
65                  70                  75                  80

Pro Phe Arg Lys Gly Gln Asn Ile Leu Val Met Cys Asp Cys Tyr Glu
                85                  90                  95

Pro Asn Gly Glu Pro Ile Pro Ser Asn Lys Arg His Gly Ala Ala Lys
            100                 105                 110

Ile Phe Ser His Pro Asp Val Lys Ala Glu Glu Pro Trp Phe Gly Ile
        115                 120                 125

Glu Gln Glu Tyr Thr Leu Leu Gln Lys Asp Thr Lys Trp Pro Leu Gly
    130                 135                 140

Trp Pro Leu Ala Tyr Pro Gly Pro Gln Gly Pro Tyr Tyr Cys Ala Ala
145                 150                 155                 160

Gly Ala Asp Lys Ser Tyr Gly Arg Asp Ile Val Asp Cys Ala Tyr Lys
                165                 170                 175

Ala Cys Leu Tyr Ala Gly Ile Asp Ile Ser Gly Ile Asn Gly Glu Val
            180                 185                 190

Met Pro Gly Gln Trp Glu Phe Gln Val Ala Pro Ala Val Gly Val Ser
        195                 200                 205

Ala Gly Asp Gln Leu Trp Val Ala Arg Tyr Ile Leu Glu Arg Ile Thr
    210                 215                 220

Glu Ile Ala Gly Val Val Val Ser Phe Asp Pro Lys Pro Ile Pro Gly
225                 230                 235                 240

Asp Trp Asn Gly Ala Gly Ala His Thr Asn Tyr Ser Thr Lys Ser Met
                245                 250                 255

Arg Ser Asp Gly Gly Tyr Glu Val Ile Lys Lys Ala Ile Gly Lys Leu
            260                 265                 270

Gly Leu Arg His Arg Glu His Ile Ala Ala Tyr Gly Asp Gly Asn Glu
        275                 280                 285

Arg Pro Leu Thr Gly Arg His Glu Thr Ala Asp Ile Asn Thr Phe Val
    290                 295                 300
```

Trp Gly Val Pro Asn Arg Gly Ala Ser Val Arg Val Gly Arg Asp Thr
305                 310                 315                 320

Glu Lys Glu Gly Lys Gly Tyr Phe Glu Asp Arg Arg Pro Ala Ser Asn
            325                 330                 335

Met Asp Pro Tyr Val Val Thr Cys Leu Ile Ala Glu Thr Thr Met Leu
            340                 345                 350

Trp Glu Pro Ser His Ser Asn Gly Asp Gly Lys Gly Ala Ala Ala Pro
            355                 360                 365

<210> SEQ ID NO 47
<211> LENGTH: 1317
<212> TYPE: DNA
<213> ORGANISM: Zea mays

<400> SEQUENCE: 47

```
caatcccaca ccaccaccac ctcctccggt ccccaacccc tgtcgcaccg cagccgccgg     60
ccatggcctg cctcaccgac ctcgtcaacc tcaacctctc ggacaccacc gagaagatca    120
tcgcggaata catatggatc ggtggatctg catggatct caggagcaaa gcaaggaccc    180
tctccggccc ggtgaccgat cccagcaagc tgcccaagtg aactacgac ggctccagca    240
cgggccaggc ccccggcgag gacagcgagg tcatcctgta cccgcaggcc atcttcaagg    300
acccattcag gagggcaac aacatccttg tgatgtgcga ttgctacacc ccagccggcg    360
agccaatccc caccaacaag aggtacaacg ccgccaagat cttcagcagc ctgaggtcg    420
ccgccgagga gccgtggtat ggtattgagc aggagtacac cctcctccag aaggacacca    480
actggcccct tgggtggccc atcggtggct tccccggccc tcagggtcct tactactgtg    540
gaatcggcgc cgaaaagtcg ttcggccgcg acatcgtgga cgcccactac aaggcctgct    600
tgtatgcggg catcaacatc agtggcatca acggggaggt gatgccaggg cagtgggagt    660
tccaagtcgg gccttccgtg gtatttcttc aggcgaccc ggtctgggtc gctcgctaca    720
ttcttgagag gatcacggag atcgccggtg tggtggtgac gttcgacccg aagccgatcc    780
cgggcgactg gaacggcgcc ggcgcgcaca ccaactacag cacggagtcg atgaggaagg    840
agggcgggta cgaggtgatc aaggcggcca tcgagaagct gaagctgcgg cacagggagc    900
acatcgcggc ctacggcgag ggcaacgacg gccggctcac cggcaggcac gagaccgccg    960
acatcaacac gttcagctgg ggcgtggcca accgcgcgc gtcggtgcgc gtgggccggg   1020
agacggagca gaacggcaag ggctacttcg aggaccgccg cccggcgtcc aacatggacc   1080
cctacgtggt cacctccatg atcgccgaga ccaccatcat ctggaagccc tgagcgccgc   1140
ggccgttgcg ttgcagggtc cccgaagcga ttgcaaagcc actgttcctt ccgttctgtt   1200
tgcttattat tgttattatc tagctagatc atccggggtc aggtcgtcgt ggtgtgccaa   1260
aacagaacac agaaagagga agaagaaaaa aaaaacaaga cgtgtggcgt ttatgtt     1317
```

<210> SEQ ID NO 48
<211> LENGTH: 356
<212> TYPE: PRT
<213> ORGANISM: Zea mays

<400> SEQUENCE: 48

Met Ala Cys Leu Thr Asp Leu Val Asn Leu Asn Leu Ser Asp Thr Thr
1               5                   10                  15

Glu Lys Ile Ile Ala Glu Tyr Ile Trp Ile Gly Gly Ser Gly Met Asp
            20                  25                  30

Leu Arg Ser Lys Ala Arg Thr Leu Ser Gly Pro Val Thr Asp Pro Ser

```
                35                  40                  45
Lys Leu Pro Lys Trp Asn Tyr Asp Gly Ser Ser Thr Gly Gln Ala Pro
 50                  55                  60

Gly Glu Asp Ser Glu Val Ile Leu Tyr Pro Gln Ala Ile Phe Lys Asp
 65                  70                  75                  80

Pro Phe Arg Arg Gly Asn Asn Ile Leu Val Met Cys Asp Cys Tyr Thr
                 85                  90                  95

Pro Ala Gly Glu Pro Ile Pro Thr Asn Lys Arg Tyr Asn Ala Ala Lys
                100                 105                 110

Ile Phe Ser Ser Pro Glu Val Ala Ala Glu Pro Trp Tyr Gly Ile
            115                 120                 125

Glu Gln Glu Tyr Thr Leu Leu Gln Lys Asp Thr Asn Trp Pro Leu Gly
130                 135                 140

Trp Pro Ile Gly Gly Phe Pro Gly Pro Gln Gly Pro Tyr Tyr Cys Gly
145                 150                 155                 160

Ile Gly Ala Glu Lys Ser Phe Gly Arg Asp Ile Val Asp Ala His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
            195                 200                 205

Ser Ser Gly Asp Gln Val Trp Val Ala Arg Tyr Ile Leu Glu Arg Ile
210                 215                 220

Thr Glu Ile Ala Gly Val Val Thr Phe Asp Pro Lys Pro Ile Pro
225                 230                 235                 240

Gly Asp Trp Asn Gly Ala Gly Ala His Thr Asn Tyr Ser Thr Glu Ser
                245                 250                 255

Met Arg Lys Glu Gly Gly Tyr Glu Val Ile Lys Ala Ala Ile Glu Lys
                260                 265                 270

Leu Lys Leu Arg His Arg Glu His Ile Ala Ala Tyr Gly Glu Gly Asn
            275                 280                 285

Asp Gly Arg Leu Thr Gly Arg His Glu Thr Ala Asp Ile Asn Thr Phe
290                 295                 300

Ser Trp Gly Val Ala Asn Arg Gly Ala Ser Val Arg Val Gly Arg Glu
305                 310                 315                 320

Thr Glu Gln Asn Gly Lys Gly Tyr Phe Glu Asp Arg Arg Pro Ala Ser
                325                 330                 335

Asn Met Asp Pro Tyr Val Val Thr Ser Met Ile Ala Glu Thr Thr Ile
                340                 345                 350

Ile Trp Lys Pro
355

<210> SEQ ID NO 49
<211> LENGTH: 1490
<212> TYPE: DNA
<213> ORGANISM: Zea mays

<400> SEQUENCE: 49
ccacatcctc ccctcattcc tccttgggtt cccagcccgt gcgccccgcc tgtcgcagtg     60
ccagtcgcgc cgcagccgcc ggccatggcc tgcctcaccg acctcgtcaa cctcaacctc    120
tcggacacca cagagaagat catcgccgag tacatatgga tcggtggatc tggcatggat    180
ctcaggagca aagccaggac cctccccggc ccggtgaccg atcccagcaa gctgcccaag    240
tggaactacg acggctccag caccggccag gcccccggcg aggacagcga ggtcatcctg    300
```

```
tacccgcagg ccatcttcaa ggacccattc aggaggggca acaacatcct tgtcatgtgc    360
gattgctaca ccccagctgg cgagccaatt cccaccaaca agaggtacag cgccgccaag    420
atcttcagca gccctgaggt cgctgccgag gagccctggt atggtatcga gcaggagtac    480
accctccttc agaaggacac caactggccc ctcggggtgg ctattggcgg cttccctggc    540
cctcagggtc cttactactg tggaatcggc gcggagaaat cgttcgggcg tgacatagtc    600
gacgcccact acaaggcctg cctgtacgca ggcatcaaca tcagtggcat caacggggag    660
gtcatgccgg ggcagtggga gttccaggtc ggaccgtccg tcggcatctc ttcgggcgat    720
caggtgtggg ttgctcgcta cattcttgag aggatcaccg agatcgccgg cgtggtggtg    780
acgttcgacc cgaagccgat cccgggcgac tggaacggcg cgggcgccca caccaactac    840
agcaccgagt ccatgaggaa ggagggcggg tacgaggtga tcaaggcggc catcgagaag    900
ctgaagctgc ggcacaagga gcacatcgcg gcctacggcg agggcaacga gcgccggctc    960
accggcaggc acgagaccgc cgacatcaac accttcagct ggggagtcgc caaccgtggc   1020
gcgtcggtgg ccgtgggcca gacggagcag aacggcaagg gctacttcga ggaccgccgg   1080
ccggcgtcca acatggatcc ctacgtggtc acctccatga tcgccgagac caccatcgtc   1140
tggaagccct gaggcatccc gtggccgtgt cgtgtcggtt tgctccgcgt acggcgctgg   1200
ccgttgcatc gcagggccca gcggttgcgc aactattttc ccttccccgt tccgtttgct   1260
tgtactacta ctctaccgct agtcctgcat agcattttag ctagaacaca acaacagcca   1320
aaaaaaaaca ttgttgcttg cttcgacttc gacgcttccc accactagtt ccattccatg   1380
ccgtccgtcc acttccttcc tgtgtaatcc tcctccaata atagacgtgt catgctgcat   1440
cctctgcatt gtataaaaga aagtggtgta atccttttgc tggcgcctcc                1490
```

<210> SEQ ID NO 50
<211> LENGTH: 355
<212> TYPE: PRT
<213> ORGANISM: Zea mays

<400> SEQUENCE: 50

```
Met Ala Cys Leu Thr Asp Leu Val Asn Leu Asn Leu Ser Asp Thr Thr
1               5                   10                  15

Glu Lys Ile Ile Ala Glu Tyr Ile Trp Ile Gly Gly Ser Gly Met Asp
            20                  25                  30

Leu Arg Ser Lys Ala Arg Thr Leu Pro Gly Pro Val Thr Asp Pro Ser
        35                  40                  45

Lys Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Cys Tyr Thr
                85                  90                  95

Pro Ala Gly Glu Pro Ile Pro Thr Asn Lys Arg Tyr Ser Ala Ala Lys
            100                 105                 110

Ile Phe Ser Ser Pro Glu Val Ala Ala Glu Glu Pro Trp Tyr Gly Ile
        115                 120                 125

Glu Gln Glu Tyr Thr Leu Leu Gln Lys Asp Thr Asn Trp Pro Leu Gly
    130                 135                 140

Trp Pro Ile Gly Gly Phe Pro Gly Pro Gln Gly Pro Tyr Tyr Cys Gly
145                 150                 155                 160
```

```
Ile Gly Ala Glu Lys Ser Phe Gly Arg Asp Ile Val Asp Ala His Tyr
                165                 170                 175
Lys Ala Cys Leu Tyr Ala Gly Ile Asn Ile Ser Gly Ile Asn Gly Glu
            180                 185                 190
Val Met Pro Gly Gln Trp Glu Phe Gln Val Gly Pro Ser Val Gly Ile
        195                 200                 205
Ser Ser Gly Asp Gln Val Trp Val Ala Arg Tyr Ile Leu Glu Arg Ile
    210                 215                 220
Thr Glu Ile Ala Gly Val Val Thr Phe Asp Pro Lys Pro Ile Pro
225                 230                 235                 240
Gly Asp Trp Asn Gly Ala Gly Ala His Thr Asn Tyr Ser Thr Glu Ser
                245                 250                 255
Met Arg Lys Glu Gly Gly Tyr Glu Val Ile Lys Ala Ala Ile Glu Lys
            260                 265                 270
Leu Lys Leu Arg His Lys Glu His Ile Ala Ala Tyr Gly Glu Gly Asn
        275                 280                 285
Glu Arg Arg Leu Thr Gly Arg His Glu Thr Ala Asp Ile Asn Thr Phe
    290                 295                 300
Ser Trp Gly Val Ala Asn Arg Gly Ala Ser Val Ala Val Gly Gln Thr
305                 310                 315                 320
Glu Gln Asn Gly Lys Gly Tyr Phe Glu Asp Arg Arg Pro Ala Ser Asn
                325                 330                 335
Met Asp Pro Tyr Val Val Thr Ser Met Ile Ala Glu Thr Thr Ile Val
            340                 345                 350
Trp Lys Pro
        355
```

<210> SEQ ID NO 51
<211> LENGTH: 1298
<212> TYPE: DNA
<213> ORGANISM: Zea mays

<400> SEQUENCE: 51

```
ctctctcttt ctctcttgtg ttcttgcctt ctgcctacta cgagtgatgg ccagcctcac      60
tgacctcgtc aacctcgacc tgagtgactg cacagacagg atcatcgccg agtacatctg     120
ggttggagga tccggcatag acctcaggag caaagcaagg acggtgaaag cccccatcac     180
cgatccgagc cagctgccaa aatgaactac gacggctcc agcaccgggc aggctcccgg     240
agaggacagc gaagtcatcc tctaccctca agccattttc aaggacccgt tcaggaaggg     300
taacaacatc cttgtgatgt gtgactgcta cacgccacaa ggcgagccaa tccccagtaa     360
caagaggtac aaagctgcca cggttttcag ccaccccgat gttgcagctg aggtgccatg     420
gtacggtatt gagcaggagt acactctcct tcagaaggat gtgagctggc cccttggctg     480
gcctgttggt ggataccctg gtccccaggg accatactac tgtgctgccg gtgccgataa     540
ggcctttggg cgcgacgtgg ttgacgccca ctacaaagcc tgcctctacg ccggcatcaa     600
catcagcggc atcaacggcg aagtcatgcc tggacagtgg agttccaag tcgggccgtc     660
cgttgggatc tctgccggcg acgagatatg ggtcgcccgc tacattctcg agaggatcac     720
tgagatggcc ggaatcgttc tctccctcga cccgaagccg atcaagggtg actggaacgg     780
cgccggcgct cacaccaact acagcaccaa gtcgatgagg gaggccggtg gctacgaggt     840
gatcaaggag gcgatcgaga agctggggaa gaggcacagg gagcacatcg ccgcgtacgg     900
cgagggcaac gagcgccgcc tcacgggccg ccacgagacc gccgacatca acaccttcaa     960
```
atggggcgtg gcgaaccgcg gcgcgtccat ccgcgtcggc cgcgacaccg agaaggaggg 1020
caagggatac ttcgaggacc gcaggccggc ttccaacatg gacccctacg tcgtcaccgg 1080
catgatcgcc gacaccacca tcctgtggaa gggaaactga taaaaccact gttcttctcc 1140
tgcacgcatg catccgcccc gtgctgccac tttttgtttt tcaaatttcg attcccgtcc 1200
taaagtttgt tagcacttat tatttcgctc tccagtgtac tgctcggaaa gtccgaataa 1260
aaacggctct aatgattttg tttaaaaaaa aaaaaaaa 1298

<210> SEQ ID NO 52
<211> LENGTH: 357
<212> TYPE: PRT
<213> ORGANISM: Zea mays

<400> SEQUENCE: 52

Met Ala Ser Leu Thr Asp Leu Val Asn Leu Asp Leu Ser Asp Cys Thr
1 5 10 15

Asp Arg Ile Ile Ala Glu Tyr Ile Trp Val Gly Gly Ser Gly Ile Asp
20 25 30

Leu Arg Ser Lys Ala Arg Thr Val Lys Gly Pro Ile Thr Asp Pro Ser
35 40 45

Gln Leu Pro Lys Trp Asn Tyr Asp Gly Ser Ser Thr Gly Gln Ala Pro
50 55 60

Gly Glu Asp Ser Glu Val Ile Leu Tyr Pro Gln Ala Ile Phe Lys Asp
65 70 75 80

Pro Phe Arg Lys Gly Asn Asn Ile Leu Val Met Cys Asp Cys Tyr Thr
85 90 95

Pro Gln Gly Glu Pro Ile Pro Ser Asn Lys Arg Tyr Lys Ala Ala Thr
100 105 110

Val Phe Ser His Pro Asp Val Ala Ala Glu Val Pro Trp Tyr Gly Ile
115 120 125

Glu Gln Glu Tyr Thr Leu Leu Gln Lys Asp Val Ser Trp Pro Leu Gly
130 135 140

Trp Pro Val Gly Gly Tyr Pro Gly Pro Gln Gly Pro Tyr Tyr Cys Ala
145 150 155 160

Ala Gly Ala Asp Lys Ala Phe Gly Arg Asp Val Val Asp Ala His Tyr
165 170 175

Lys Ala Cys Leu Tyr Ala Gly Ile Asn Ile Ser Gly Ile Asn Gly Glu
180 185 190

Val Met Pro Gly Gln Trp Glu Phe Gln Val Gly Pro Ser Val Gly Ile
195 200 205

Ser Ala Gly Asp Glu Ile Trp Val Ala Arg Tyr Ile Leu Glu Arg Ile
210 215 220

Thr Glu Met Ala Gly Ile Val Leu Ser Leu Asp Pro Lys Pro Ile Lys
225 230 235 240

Gly Asp Trp Asn Gly Ala Gly Ala His Thr Asn Tyr Ser Thr Lys Ser
245 250 255

Met Arg Glu Ala Gly Gly Tyr Glu Val Ile Lys Glu Ala Ile Glu Lys
260 265 270

Leu Gly Lys Arg His Arg Glu His Ile Ala Ala Tyr Gly Glu Gly Asn
275 280 285

Glu Arg Arg Leu Thr Gly Arg His Glu Thr Ala Asp Ile Asn Thr Phe
290 295 300

Lys Trp Gly Val Ala Asn Arg Gly Ala Ser Ile Arg Val Gly Arg Asp
305 310 315 320

Thr Glu Lys Glu Gly Lys Gly Tyr Phe Glu Asp Arg Arg Pro Ala Ser
                325                 330                 335

Asn Met Asp Pro Tyr Val Val Thr Gly Met Ile Ala Asp Thr Thr Ile
            340                 345                 350

Leu Trp Lys Gly Asn
        355

<210> SEQ ID NO 53
<211> LENGTH: 1483
<212> TYPE: DNA
<213> ORGANISM: Zea mays

<400> SEQUENCE: 53

| | | | | | |
|---|---|---|---|---|---|
| gggcggcggc | cggtccgtgt | ccgtgtccgt | cgacggttgg | ttcgggaatg | gcgcaggcgg | 60 |
| tggtgccggc | gatgcagtgc | cgggtcggag | tgaaggcggc | ggcggggagg | gtgtggagcg | 120 |
| ccggcaggac | taggaccggc | cgcggcggcg | cctcgccggg | gttcaaggtc | atggccgtca | 180 |
| gcacgggcag | caccggggtg | gtgccgcgcc | tcgagcagct | gctcaacatg | gacaccacgc | 240 |
| cctacaccga | caaggtcatc | gccgagtaca | tctgggtcgg | aggatctgga | atcgacatca | 300 |
| gaagcaaatc | aaggacgatt | tcgaaacccg | tggaggatcc | ctcagaacta | ccaaaatgga | 360 |
| actacgatgg | atctagcaca | ggacaagccc | cgggagaaga | cagtgaagtc | attctatacc | 420 |
| cccaggctat | cttcaaggac | ccattccgag | gtggcaacaa | cgttttggtt | atctgtgaca | 480 |
| cctacacgcc | acaggggaa | cccttccaa | ctaacaaacg | ccacagggct | gcgcaaattt | 540 |
| tcagcgaccc | aaaggtcggt | gaacaagtgc | catggtttgg | catagagcaa | gagtacactt | 600 |
| tgctccagaa | agatgtaaat | tggcctcttg | gttggcctgt | tggaggcttc | cctggtcccc | 660 |
| agggtccata | ctactgtgcc | gtaggagccg | acaaatcatt | tggccgtgac | atatcagatg | 720 |
| ctcactacaa | ggcatgcctc | tacgctggaa | tcaacattag | tggaacaaac | ggggaggtca | 780 |
| tgcctggtca | gtgggagtac | caagttggac | ctagtgttgg | tattgaagca | ggagatcaca | 840 |
| tatggatttc | gagatacatt | tcgagagaa | tcacagagca | agctggggtt | gtccttaccc | 900 |
| ttgatccaaa | accaattcag | ggtgactgga | acggagctgg | ctgccacaca | aattacagca | 960 |
| caaagaccat | gcgcgaagac | ggcgggtttg | aagagatcaa | gagagcaatc | ctgaaccttt | 1020 |
| ctctgcgcca | tgatctgcat | attagtgcat | acggagaagg | aaatgaaaga | agattgactg | 1080 |
| ggaaacatga | gactgcgagc | atcggaacct | tctcatgggg | tgtggcaaac | cgcggctgct | 1140 |
| ctatccgtgt | ggggcgggat | accgaggcaa | aagggaaagg | ttacctggaa | gaccgtcggc | 1200 |
| cggcatcaaa | catggacccg | tacattgtga | cggggctact | ggccgagacc | acgatcctct | 1260 |
| ggcagccatc | cctcgaggcg | gaggctcttg | ccgccaagaa | gctggcgctg | aaggtgtgaa | 1320 |
| gcagctgaag | gatggttcag | gcaccaatat | aaaccggtcc | gcgacaagat | tgatctttgt | 1380 |
| gtccatggcc | gttgggtctt | gcgactctct | gctcggcggt | gccactctgt | acaaaatcac | 1440 |
| ggctgtcttt | gattcatcgg | atattcggat | acgtttgttt | gtt | | 1483 |

<210> SEQ ID NO 54
<211> LENGTH: 423
<212> TYPE: PRT
<213> ORGANISM: Zea mays

<400> SEQUENCE: 54

Met Ala Gln Ala Val Val Pro Ala Met Gln Cys Arg Val Gly Val Lys
1               5                   10                  15

```
Ala Ala Ala Gly Arg Val Trp Ser Ala Gly Arg Thr Arg Thr Gly Arg
            20                  25                  30

Gly Gly Ala Ser Pro Gly Phe Lys Val Met Ala Val Ser Thr Gly Ser
            35                  40                  45

Thr Gly Val Val Pro Arg Leu Glu Gln Leu Leu Asn Met Asp Thr Thr
50                  55                  60

Pro Tyr Thr Asp Lys Val Ile Ala Glu Tyr Ile Trp Val Gly Gly Ser
65                  70                  75                  80

Gly Ile Asp Ile Arg Ser Lys Ser Arg Thr Ile Ser Lys Pro Val Glu
                85                  90                  95

Asp Pro Ser Glu Leu Pro Lys Trp Asn Tyr Asp Gly Ser Ser Thr Gly
            100                 105                 110

Gln Ala Pro Gly Glu Asp Ser Glu Val Ile Leu Tyr Pro Gln Ala Ile
            115                 120                 125

Phe Lys Asp Pro Phe Arg Gly Gly Asn Asn Val Leu Val Ile Cys Asp
            130                 135                 140

Thr Tyr Thr Pro Gln Gly Glu Pro Leu Pro Thr Asn Lys Arg His Arg
145                 150                 155                 160

Ala Ala Gln Ile Phe Ser Asp Pro Lys Val Gly Glu Gln Val Pro Trp
                165                 170                 175

Phe Gly Ile Glu Gln Glu Tyr Thr Leu Leu Gln Lys Asp Val Asn Trp
            180                 185                 190

Pro Leu Gly Trp Pro Val Gly Gly Phe Pro Gly Pro Gln Gly Pro Tyr
            195                 200                 205

Tyr Cys Ala Val Gly Ala Asp Lys Ser Phe Gly Arg Asp Ile Ser Asp
210                 215                 220

Ala His Tyr Lys Ala Cys Leu Tyr Ala Gly Ile Asn Ile Ser Gly Thr
225                 230                 235                 240

Asn Gly Glu Val Met Pro Gly Gln Trp Glu Tyr Gln Val Gly Pro Ser
                245                 250                 255

Val Gly Ile Glu Ala Gly Asp His Ile Trp Ile Ser Arg Tyr Ile Leu
            260                 265                 270

Glu Arg Ile Thr Glu Gln Ala Gly Val Val Leu Thr Leu Asp Pro Lys
            275                 280                 285

Pro Ile Gln Gly Asp Trp Asn Gly Ala Gly Cys His Thr Asn Tyr Ser
290                 295                 300

Thr Lys Thr Met Arg Glu Asp Gly Gly Phe Glu Glu Ile Lys Arg Ala
305                 310                 315                 320

Ile Leu Asn Leu Ser Leu Arg His Asp Leu His Ile Ser Ala Tyr Gly
                325                 330                 335

Glu Gly Asn Glu Arg Arg Leu Thr Gly Lys His Glu Thr Ala Ser Ile
            340                 345                 350

Gly Thr Phe Ser Trp Gly Val Ala Asn Arg Gly Cys Ser Ile Arg Val
            355                 360                 365

Gly Arg Asp Thr Glu Ala Lys Gly Lys Gly Tyr Leu Glu Asp Arg Arg
            370                 375                 380

Pro Ala Ser Asn Met Asp Pro Tyr Ile Val Thr Gly Leu Leu Ala Glu
385                 390                 395                 400

Thr Thr Ile Leu Trp Gln Pro Ser Leu Glu Ala Glu Ala Leu Ala Ala
                405                 410                 415

Lys Lys Leu Ala Leu Lys Val
            420
```

MANIPULATION OF GLUTAMINE SYMTHETASES (GS) TO IMPROVE NITROGEN USE EFFICIENCY AND GRAIN YIELD IN HIGHER PLANTS

CROSS REFERENCE

This utility application is a continuation of U.S. patent application Ser. No. 13/623,938 filed Sep. 21, 2012, now abandoned, which is a divisional of U.S. patent application Ser. No. 12/607,089 filed Oct. 28, 2009, now abandoned, and claims the benefit U.S. Provisional Patent Application Ser. No. 61/109,651, filed Oct. 30, 2008, which is incorporated herein by reference.

FIELD OF THE INVENTION

The invention relates generally to the field of molecular biology.

BACKGROUND OF THE INVENTION

Nitrogen (N) is the most abundant inorganic nutrient taken up from the soil by plants for growth and development. Maize roots absorb most of the N from the soil in the form of nitrate, the majority of which is transported to the leaf for reduction and assimilation. Nitrate is reduced to nitrite by nitrate reductase (NR) in the cytosol and then nitrite is transported into chloroplast where it is reduced by nitrite reductase (NiR) to ammonium. Ammonium is assimilated into glutamine by the glutamine synthase-glutamate synthase system (Crawford and Glass, (1998) *Trends in Plant Science* 3:389-395). Also, it has long been known that significant amounts of N are lost from the plant aerial parts by volatilization (Glyan'ko, et al., (1980) *Agrokhimiya* 8:19-26; Hooker, et al., (1980) *Agronomy Journal* 72(5):789-792; Silva, et al., (1981) *Crop Science* 21(6):913-916; Stutte, et al., (1981) *Crop Science* 21(4):596-600; Foster, et al., (1986) *Annals of Botany* 57(3):305-307; Parton, et al., (1988) *Agronomy Journal* 80(3):419-425; Kamiji, et al., (1989) *Japanese Journal of Crop Science* 58(1):140-142; Morgan, et al., (1989) *Crop Science* 29(3):726-731; O'Deen, (1989) *Agronomy Journal* 81(6):980-985; Guindo, et al., (1994) *Arkansas Farm Research* 43(1):12-13; Heckathorn, et al., (1995) *Oecologia* 101(3):361-365; Cabezas, et al., (1997) *Revista Brasileira de Ciencia do Solo* 21(3):481-487). Experimental evidence supports the loss of N through ammonium and not through N oxides (Hooker, et al., 1980). Treatment with chemicals that inhibit glutamine or glutamate synthase activities led to increased loss of ammonium through volatilization (Foster, et al., 1986). Loss of N is not only limited to C-3 species as C-4 plants have also been reported to lose N through volatilization (Heckathorn, et al., 1995).

Several independent lines of evidence indicate that glutamine synthetase (GS) is involved in yield formation and its expression levels affect nitrogen use efficiency (NUE) in maize. GS carries out two main functions in plant cells: (1) assimilate ammonium resulting from nitrate reduction into organic form during the biosynthetic phase and (2) assimilate ammonium generated by photorespiration, deaminases and glutamate dehydrogenase, for example, during seed germination and leaf senescence when proteins are remobilized as N source or used as source of energy. The cytosolic GS is referred to as GS1 and the plastidial form as GS2. In a recent report (Martin, et al., (2006) *The Plant Cell* 18(11):3252-74), a reverse genetics strategy was used to show that GS indeed is a limiting factor for grain number and grain weight, both components of grain yield in maize. Earlier QTL mapping experiments also implicated GS isozymes in the determination of yield and NUE (Gallais and Hirel, (2004) *J Exp Bot.* 55(396):295-306). In other experiments, two GS genes located on chromosome 1, including one expressed in the root, show significant ($p=10^{-4}$) association with biomass at 1 and 5 mM applied N (data not shown). During leaf senescence, remobilization of N takes place from source (leaf) to sink (developing grain) tissues. Proteins are broken down into amino-acids, which are then transported through phloem to the sink tissue. Grain protein accounts for ~60-70% of the total plant N at maturity in maize, which means 30-40% N still remains in the stover. The current invention involves efforts to over-express the cytosolic isoforms of GS under the control of different promoters in maize to improve NUE and thus grain yield.

SUMMARY OF THE INVENTION

The present invention provides polynucleotides, related polypeptides and all conservatively modified variants of the present GS sequences. The invention provides sequences for the GS genes. 6 *Arabidopsis,* 6 maize, 4 rice, 3 sorghum and 8 soybean GS genes were identified. Table 1 lists these genes and their sequence ID numbers.

TABLE 1

| SEQUENCE ID NUMBER | IDENTITY |
| --- | --- |
| SEQ ID NO: 1 | AT1G48470 Polynucleotide |
| SEQ ID NO: 2 | AT1G48470 Polypeptide |
| SEQ ID NO: 3 | AT1G66200 Polynucleotide |
| SEQ ID NO: 4 | AT1G66200 Polypeptide |
| SEQ ID NO: 5 | AT3G17820 Polynucleotide |
| SEQ ID NO: 6 | AT3G17820 Polypeptide |
| SEQ ID NO: 7 | AT5G16570 Polynucleotide |
| SEQ ID NO: 8 | AT5G16570 Polypeptide |
| SEQ ID NO: 9 | AT5G35630 Polynucleotide |
| SEQ ID NO: 10 | AT5G35630 Polypeptide |
| SEQ ID NO: 11 | AT5G37600 Polynucleotide |
| SEQ ID NO: 12 | AT5G37600 Polypeptide |
| SEQ ID NO: 13 | Gm0005x00111 Polynucleotide |
| SEQ ID NO: 14 | Gm0005x00111 Polypeptide |
| SEQ ID NO: 15 | Gm0015x00387 Polynucleotide |
| SEQ ID NO: 16 | Gm0015x00387 Polypeptide |
| SEQ ID NO: 17 | Gm0030x00147 Polynucleotide |
| SEQ ID NO: 18 | Gm0030x00147 Polypeptide |
| SEQ ID NO: 19 | Gm0040x00114 Polynucleotide |
| SEQ ID NO: 20 | Gm0040x00114 Polypeptide |
| SEQ ID NO: 21 | Gm0081x00134 Polynucleotide |
| SEQ ID NO: 22 | Gm0081x00134 Polypeptide |
| SEQ ID NO: 23 | Gm0136x00208 Polynucleotide |
| SEQ ID NO: 24 | Gm0136x00208 Polypeptide |
| SEQ ID NO: 25 | Gm0232x00015 Polynucleotide |
| SEQ ID NO: 26 | Gm0232x00015 Polypeptide |
| SEQ ID NO: 27 | Gm0271x00039 Polynucleotide |
| SEQ ID NO: 28 | Gm0271x00039 Polypeptide |
| SEQ ID NO: 29 | Os02g50240 Polynucleotide |
| SEQ ID NO: 30 | Os02g50240 Polypeptide |
| SEQ ID NO: 31 | Os03g12290 Polynucleotide |
| SEQ ID NO: 32 | Os03g12290 Polypeptide |
| SEQ ID NO: 33 | Os03g50490 Polynucleotide |
| SEQ ID NO: 34 | Os03g50490 Polypeptide |
| SEQ ID NO: 35 | Os04g56400 Polynucleotide |
| SEQ ID NO: 36 | Os04g56400 Polypeptide |
| SEQ ID NO: 37 | Sb01g143820 Polynucleotide |
| SEQ ID NO: 38 | Sb01g143820 Polypeptide |
| SEQ ID NO: 39 | Sb04g133790 Polynucleotide |
| SEQ ID NO: 40 | Sb04g133790 Polypeptide |
| SEQ ID NO: 41 | Sb06g147820 Polynucleotide |
| SEQ ID NO: 42 | Sb06g147820 Polypeptide |
| SEQ ID NO: 43 | ZmGS1-1 Polynucleotide |
| SEQ ID NO: 44 | ZmGS1-1 Polypeptide |

TABLE 1-continued

| SEQUENCE ID NUMBER | IDENTITY |
|---|---|
| SEQ ID NO: 45 | ZmGS1-2 Polynucleotide |
| SEQ ID NO: 46 | ZmGS1-2 Polypeptide |
| SEQ ID NO: 47 | ZmGS1-3 Polynucleotide |
| SEQ ID NO: 48 | ZmGS1-3 Polypeptide |
| SEQ ID NO: 49 | ZmGS1-4 Polynucleotide |
| SEQ ID NO: 50 | ZmGS1-4 Polypeptide |
| SEQ ID NO: 51 | ZmGS1-5 Polynucleotide |
| SEQ ID NO: 52 | ZmGS1-5 Polypeptide |
| SEQ ID NO: 53 | ZmGS2-Polynucleotide |
| SEQ ID NO: 54 | ZmGS2-Polypeptide |

Therefore, in one aspect, the present invention relates to an isolated nucleic acid comprising an isolated polynucleotide sequence encoding GS protein. One embodiment of the invention is an isolated polynucleotide comprising a nucleotide sequence selected from the group consisting of: (a) the nucleotide sequence comprising SEQ ID NO: 43, 45, 47, 49, 51, 53; (b) the nucleotide sequence encoding an amino acid sequence comprising SEQ ID NO: 44, 46, 48, 50, 52 and 54 and (c) the nucleotide sequence comprising at least 70% sequence identity to SEQ ID NO: 43, 45, 47, 49, 51, 53, wherein said polynucleotide encodes a polypeptide having GS enzyme activity.

Compositions of the invention include an isolated polypeptide comprising an amino acid sequence selected from the group consisting of: (a) the amino acid sequence comprising SEQ ID NO: 44, 46, 48, 50, 52 and 54 and (b) the amino acid sequence comprising at least 70% sequence identity to SEQ ID NO: 44, 46, 48, 50, 52 and 54, wherein said polypeptide has GS enzyme activity.

In another aspect, the present invention relates to a recombinant expression cassette comprising a nucleic acid as described. Additionally, the present invention relates to a vector containing the recombinant expression cassette. Further, the vector containing the recombinant expression cassette can facilitate the transcription and translation of the nucleic acid in a host cell. The present invention also relates to the host cells able to express the polynucleotide of the present invention. A number of host cells could be used, such as but not limited to, microbial, mammalian, plant or insect.

In yet another embodiment, the present invention is directed to a transgenic plant or plant cells, containing the nucleic acids of the present invention. Preferred plants containing the polynucleotides of the present invention include but are not limited to maize, soybean, sunflower, sorghum, canola, wheat, alfalfa, cotton, rice, barley, tomato, switchgrass, myscanthus, triticale and millet. In another embodiment, the transgenic plant is a maize plant or plant cells. Another embodiment is the transgenic seeds from the transgenic plant. Another embodiment of the invention includes plants comprising a GS polypeptide of the invention operably linked to a promoter that drives expression in the plant. The plants of the invention can have altered GS as compared to a control plant. In some plants, the GS is altered in a vegetative tissue, a reproductive tissue, or a vegetative tissue and a reproductive tissue. Plants of the invention can have at least one of the following phenotypes including but not limited to: increased leaf size, increased ear size, increased seed size, increased endosperm size, alterations in the relative size of embryos and endosperms leading to changes in the relative levels of protein, oil and/or starch in the seeds, absence of tassels, absence of functional pollen bearing tassels or increased plant size.

Another embodiment of the invention would be plants that have been genetically modified at a genomic locus, wherein the genomic locus encodes a GS polypeptide of the invention.

Methods for increasing the activity of a GS polypeptide in a plant are provided. The method can comprise introducing into the plant a GS polynucleotide of the invention. Providing the polypeptide can decrease the number of cells in plant tissue, modulating the tissue growth and size.

Methods for reducing or eliminating the level of a GS polypeptide in the plant are provided. The level or activity of the polypeptide could also be reduced or eliminated in specific tissues, causing increased GS in said tissues. Reducing the level and/or activity of the GS polypeptide increases the number of cells produced in the associated tissue.

Compositions further include plants and seed having a DNA construct comprising a nucleotide sequence of interest operably linked to a promoter of the current invention. In specific embodiments, the DNA construct is stably integrated into the genome of the plant. The method comprises introducing into a plant a nucleotide sequence of interest operably linked to a promoter of the invention.

BRIEF DESCRIPTION OF THE FIGURES

FIG. 1A, FIG. 1B, FIG. 1C, FIG. 1D, FIG. 1E, FIG. 1F, FIG. 1G, FIG. 1H, FIG. 1I, and FIG. 1J Sequence alignment of GS proteins from Arabidopsis, soybean, rice, sorghum and maize. The polypeptide alignment of all 27 sequences is shown in FIG. 1A-FIG. 1J. Several regions of very high homology were identified by this alignment. All these polypeptides from different species (except SEQ ID NO: 20) show a sequence identity in the range of 70-95% among different members. Due to several insertions, SEQ ID NO: 20 shows an identity in the range of 53-74% with different GS polypeptides from different species. SEQ ID NOS: 10, 18, 28, 36, 42 and 54 belong to the GS2 group (chloroplast-localized) as in all the polypeptide a clear chloroplast targeting peptide was identified.

FIG. 2 Phylogentic tree of GS proteins from Arabidopsis, rice, soybean, sorghum and maize. Analysis of all the 27 polypeptides are shown in FIG. 2. ZMGS1-1/1-5, ZMGS1-3/1-4, ZMGS1-2 and ZMGS2 along with members from other species were clustered in four different clades. There is a soybean-specific clade with SEQ ID NOS: 14, 22, 24 and 26.

DETAILED DESCRIPTION OF THE INVENTION

Figure 3A:
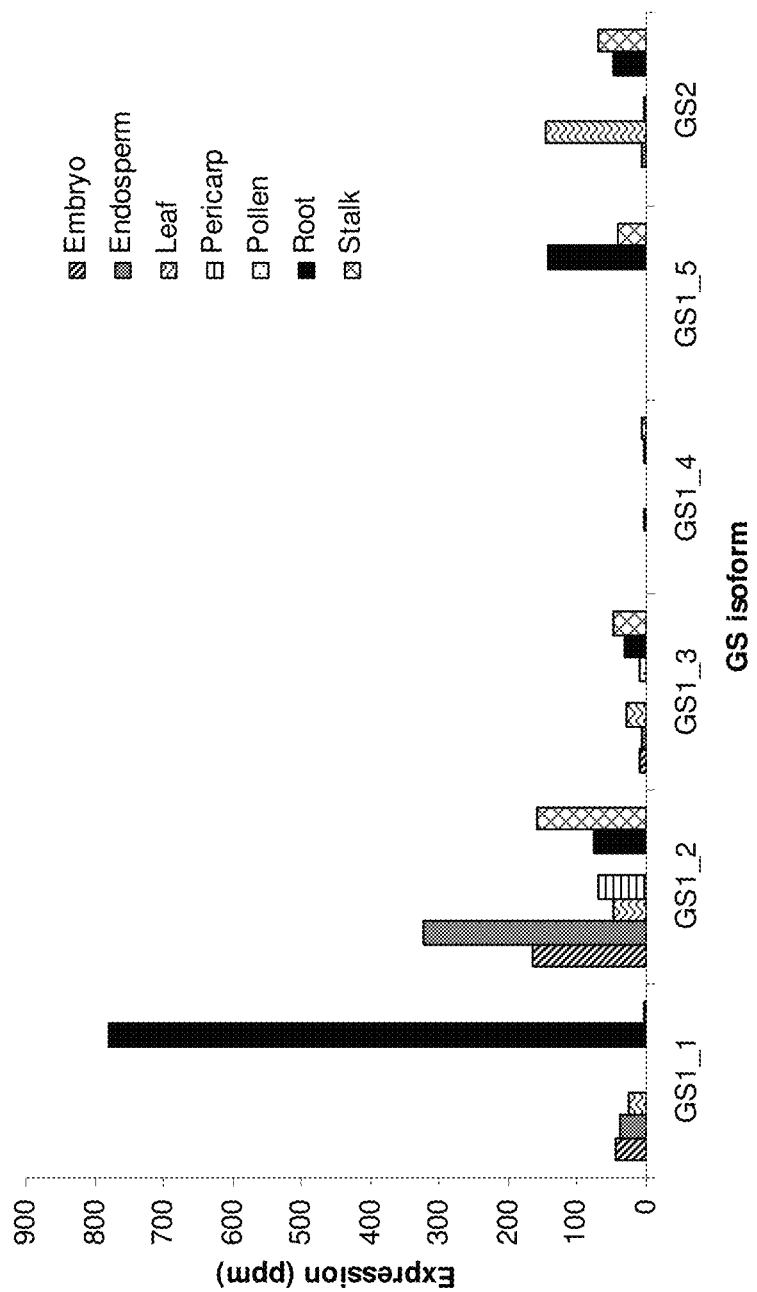
FIG. 3A, FIG. 3B, and FIG. 3C Expression analyses of GS genes from maize were conducted on a MPSS database consisting of more than 300 different tissue libraries. GS1-1 and GS2 were expressed predominantly in roots and leaves, respectively (FIG. 3A). GS1-2 expresses more or less in all the tissues with a slightly higher expression in pollen (FIG. 3A). GS1-3 and 1-4 were expressed at very low levels in most of the tissues examined whereas GS1-5 expresses at about 100 ppm in roots (FIG. 3A). GS1-1 showed 15-20× higher expression in root-cortex as compared to other isoforms (FIG. 3B). Among all the isoforms, only GS1-2 and 1-5 show the expression in the range of ~150-700 PPM in pedicel (FIG. 3C).

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, BOTANY: PLANT BIOLOGY AND ITS RELATION TO HUMAN AFFAIRS, John Wiley (1982); CELL CULTURE AND SOMATIC CELL GENETICS OF PLANTS, vol. 1, Vasil, ed. (1984); Stanier, et al., THE MICROBIAL WORLD, 5$^{th}$ ed., Prentice-Hall (1986); Dhringra and Sinclair, BASIC PLANT PATHOLOGY METHODS, CRC Press (1985); Maniatis, et al., MOLECULAR CLONING: A LABORATORY MANUAL (1982); DNA CLONING, vols. I and II, Glover, ed. (1985); OLIGONUCLEOTIDE SYNTHESIS, Gait, ed. (1984); NUCLEIC ACID HYBRIDIZATION, Hames and Higgins, eds. (1984) and the series METHODS IN ENZYMOLOGY, Colowick and Kaplan, eds, Academic Press, Inc., San Diego, Calif.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), 0-Beta Replicase systems, transcription-based amplification system (TAS), and strand displacement amplification (SDA). See, e.g., DIAGNOSTIC MOLECULAR MICROBIOLOGY: PRINCIPLES AND APPLICATIONS, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for it's native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, PROTEINS, W.H. Freeman and Co. (1984).

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma capricolum* (Yamao, et al., (1985) *Proc. Natl. Acad. Sci. USA* 82:2306-9) or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet, switchgrass, myscanthus, triticale and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "GS nucleic acid" means a nucleic acid comprising a polynucleotide ("GS polynucleotide") encoding a full length or partial length GS polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, GUIDE TO MOLECULAR CLONING TECHNIQUES, from the series METHODS IN ENZYMOLOGY, vol. 152, Academic Press, Inc., San Diego, Calif. (1987); Sambrook, et al., MOLECULAR CLONING: A LABORATORY MANUAL, $2^{nd}$ ed., vols. 1-3 (1989) and CURRENT PROTOCOLS IN MOLECULAR BIOLOGY, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is *Zea mays*.

As used herein, "yield" may include reference to bushels per acre of a grain crop at harvest, as adjusted for grain moisture (15% typically for maize, for example). Grain moisture is measured in the grain at harvest. The adjusted test weight of grain is determined to be the weight in pounds per bushel, adjusted for grain moisture level at harvest.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions.

The term "GS polypeptide" refers to one or more amino acid sequences. The term is also inclusive of fragments, variants, homologs, alleles or precursors (e.g., preproproteins or proproteins) thereof. A "GS protein" comprises a GS polypeptide. Unless otherwise stated, the term "GS nucleic acid" means a nucleic acid comprising a polynucleotide ("GS polynucleotide") encoding a GS polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention; or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-84: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part I, chapter 2, "Overview of principles of hybridization and the strategy of nucleic acid probe assays," Elsevier, New York (1993); and CURRENT PROTOCOLS IN MOLECULAR BIOLOGY, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA and 25 mM Na phosphate at 65° C., and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) Proc. *Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package®, Version 8 (available from Genetics Computer Group (GCG® programs (Accelrys, Inc., San Diego, Calif.)). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65, and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, CURRENT PROTOCOLS IN MOLECULAR BIOLOGY, Chapter 19, Ausubel, et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

The invention discloses GS polynucleotides and polypeptides. The novel nucleotides and proteins of the invention have an expression pattern which indicates that they regulate ammonium transport and thus play an important role in plant development. The polynucleotides are expressed in various plant tissues. The polynucleotides and polypeptides thus provide an opportunity to manipulate plant development to alter seed and vegetative tissue development, timing or composition. This may be used to create aa plant with altered N composition in source and sink.

Nucleic Acids

The present invention provides, inter alia, isolated nucleic acids of RNA, DNA and analogs and/or chimeras thereof, comprising a GS polynucleotide.

The present invention also includes polynucleotides optimized for expression in different organisms. For example, for expression of the polynucleotide in a maize plant, the sequence can be altered to account for specific codon preferences and to alter GC content as according to Murray, et al., supra. Maize codon usage for 28 genes from maize plants is listed in Table 4 of Murray et al., supra.

The GS nucleic acids of the present invention comprise isolated GS polynucleotides which are inclusive of:

(a) a polynucleotide encoding a GS polypeptide and conservatively modified and polymorphic variants thereof;

(b) a polynucleotide having at least 70% sequence identity with polynucleotides of (a) or (b);

(c) complementary sequences of polynucleotides of (a) or (b).

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter or linker for cloning and/or expression of a polynucleotide of the present invention. Additional sequences may be added to such cloning and/or expression sequences to optimize their function in cloning and/or expression, to aid in isolation of the polynucleotide or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMC1neo, pOG44, pOG45, pFRTβGAL, pNEβGAL, pRS403, pRS404, pRS405, pRS406, pRS413, pRS414, pRS415, pRS416, lambda MOSSlox and lambda MOSElox. Optional vectors for the present invention, include but are not limited to, lambda ZAP II and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20):1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68 and the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395 or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT Publication Number 96/19256. See also, Zhang, et al., (1997) *Proc. Natl. Acad. Sci. USA* 94:4504-9 and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system and may include properties of: an encoded protein, a transcriptional element, a sequence controlling transcription, RNA processing, RNA stability, chromatin conformation, translation or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated or cell- or tissue-specific/selective expression), a transcription initiation start site, a ribosome binding site, an RNA processing signal, a transcription termination site and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30) and maize H3 histone (Lepetit, et al., (1992) *Mol. Gen. Genet.* 231:276-85 and Atanassvoa, et al., (1992) *Plant Journal* 2(3):291-300); ALS promoter, as described in PCT Application Number WO 1996/30530 and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions or the presence of light. Examples of inducible promoters are the Adh1 promoter, which is inducible by hypoxia or cold stress, the Hsp70 promoter, which is inducible by heat stress and the PPDK promoter, which is inducible by light.

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes or from T-DNA. The 3' end sequence to be added can be derived from, for example, the nopaline synthase or octopine synthase genes or alternatively from another plant gene or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50 and An, et al., (1989) *Plant Cell* 1:115-22) and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2 and 6, the Bronze-1 intron are known in the art. See generally, THE MAIZE HANDBOOK, Chapter 116, Freeling and Walbot, eds., Springer, New York (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell,* 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119, and hereby incorporated by reference) or signal peptides which target proteins to the plastids such as that of rapeseed enoyl-Acp reductase (Verwaert, et al., (1994) *Plant Mol. Biol.* 26:189-202) are useful in the invention. The barley alpha amylase signal sequence fused to the GS polynucleotide is the preferred construct for expression in maize for the present invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987) *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11 and Berger, et al., (1989) *Proc. Natl. Acad. Sci. USA*, 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian or preferably plant cells. The cells produce the protein in a non-natural condition (e.g., in quantity, composition, location and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation and a transcription/translation terminator. Constitutive promoters are classified as providing for a range of constitutive expression. Thus, some are weak constitutive promoters and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level," or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression or incorporation of the targeting molecule into a fusion protein. Such modifications are well known to those of skill in the art and include, for example, a methionine added at the amino terminus to provide an initiation site or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198: 1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., METHODS IN YEAST GENETICS, Cold Spring Harbor Laboratory (1982) is a well recognized work describing the various methods available to produce the protein in yeast. Two widely utilized yeasts for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect or plant origin. Mammalian cell systems often will be in the form of monolayers of cells although mammalian cell suspensions may also be used. A number of suitable host cell lines capable of expressing intact proteins have been developed in the art, and include the HEK293, BHK21 and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49) and necessary processing information sites, such as ribosome binding sites, RNA splice sites, polyadenylation sites (e.g., an SV40 large T Ag poly A addition site) and transcriptional terminator sequences. Other animal cells useful for production of proteins of the present invention are available, for instance, from the American Type Culture Collection Catalogue of Cell Lines and Hybridomas ($7^{th}$ ed., 1992).

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., (1983) *J. Virol.* 45:773-81). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in DNA CLONING: A PRACTICAL APPROACH, vol. II, Glover, ed., IRL Press, Arlington, Va., pp. 213-38 (1985)).

In addition, the gene for GS placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert a GS polynucleotide into a plant host, including biological and physical plant transformation protocols. See, e.g., Miki et al., "Procedure for Introducing Foreign DNA into Plants," in METHODS IN PLANT MOLECULAR BIOLOGY AND BIOTECHNOLOGY, Glick and Thompson, eds., CRC Press, Inc., Boca Raton, pp. 67-88 (1993). The methods chosen vary is with the host plant, and include chemical transfection methods such as calcium phosphate, microorganism-mediated gene transfer such as *Agrobacterium* (Horsch, et al., (1985) *Science* 227:1229-31), electroporation, micro-injection and biolistic bombardment.

Expression cassettes and vectors and in vitro culture methods for plant cell or tissue transformation and regeneration of plants are known and available. See, e.g., Gruber, et al., "Vectors for Plant Transformation," in METHODS IN PLANT MOLECULAR BIOLOGY AND BIOTECHNOLOGY, supra, pp. 89-119.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334 and U.S. Pat. No. 6,300,543), electroporation (Riggs, et al., (1986) *Proc. Natl. Acad. Sci. USA* 83:5602-5606, direct gene transfer (Paszkowski, et al., (1984) *EMBO J.* 3:2717-2722) and ballistic particle acceleration (see, for example, Sanford, et al., U.S. Pat. No. 4,945,050; WO 1991/10725 and McCabe, et al., (1988) *Biotechnology* 6:923-926). Also see, Tomes, et al., Direct DNA Transfer into Intact Plant Cells Via Microprojectile Bombardment. pp. 197-213 in Plant Cell, Tissue and Organ Culture, Fundamental Methods. eds. Gamborg and Phillips, Springer-Verlag Berlin Heidelberg N.Y., 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 1991/10725 (maize); Klein, et al., (1988) *Plant Physiol.* 91:440-444 (maize); Fromm, et al., (1990) *Biotechnology* 8:833-839 and Gordon-Kamm, et al., (1990) *Plant Cell* 2:603-618 (maize); Hooydaas-Van Slogteren and Hooykaas, (1984) *Nature* (London) 311:763-764; Bytebier, et al., (1987) *Proc. Natl. Acad. Sci. USA* 84:5345-5349 (Liliaceae); De Wet, et al., (1985) In *The Experimental Manipulation of Ovule Tissues*, ed. Chapman, et al., pp. 197-209 Longman, N.Y. (pollen); Kaeppler, et al., (1990) *Plant Cell Reports* 9:415-418 and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255 and Christou and Ford (1995) *Annals of Botany* 75:407-413 (rice); Osjoda, et al., (1996) *Nature Biotech.* 14:745-750; Agrobacterium mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185), all of which are herein incorporated by reference.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. patent application Ser. No. 913,914, filed Oct. 1, 1986, as referenced in U.S. Pat. No. 5,262,306, issued Nov. 16, 1993 and Simpson, et al., (1986) *Plant Mol. Biol.* 6:403-15 (also referenced in the '306 patent), all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon, switchgrass, myscanthus, triticale and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae and Chenopodiaceae. Monocot plants can now be transformed with some success. EP Patent Application Number 604 662 A1 discloses a method for transforming monocots using *Agrobacterium*. EP Patent Application Number 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra and U.S. patent application Ser. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206 and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731 and Christou, et al., (1987) *Proc. Natl. Acad. Sci. USA* 84:3962. Direct uptake of DNA into protoplasts using $CaCl_2$ precipitation, polyvinyl alcohol or poly-L-ornithine has also been reported. See, e.g., Hain, et al., (1985) *Mol. Gen. Genet.* 199:161 and Draper, et al., (1982) *Plant Cell Physiol.* 23:451.

Electroporation of protoplasts and whole cells and tissues has also been described. See, e.g., Donn, et al., (1990) in *Abstracts of the VIIth Intl. Congress on Plant Cell and Tissue Culture IAPTC*, A2-38, p. 53; D'Halluin, et al., (1992) *Plant Cell* 4:1495-505 and Spencer, et al., (1994) *Plant Mol. Biol.* 24:51-61.

Increasing the Activity and/or Level of a GS Polypeptide

Methods are provided to increase the activity and/or level of the GS polypeptide of the invention. An increase in the level and/or activity of the GS polypeptide of the invention can be achieved by providing to the plant a GS polypeptide. The GS polypeptide can be provided by introducing the amino acid sequence encoding the GS polypeptide into the plant, introducing into the plant a nucleotide sequence encoding a GS polypeptide or alternatively by modifying a genomic locus encoding the GS polypeptide of the invention.

As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having GS enzyme activity. It is also recognized that the methods of the invention may employ a polynucleotide that is not capable of directing, in the transformed plant, the expression of a protein or an RNA. Thus, the level and/or activity of a GS polypeptide may be increased by altering the gene encoding the GS polypeptide or its promoter. See, e.g., Kmiec, U.S. Pat. No. 5,565,350; Zarling, et al., PCT/US93/03868. Therefore mutagenized plants that carry mutations in GS genes, where the mutations increase expression of the GS gene or increase the GS enzyme activity of the encoded GS polypeptide are provided.

Reducing the Activity and/or Level of a GS Polypeptide

Methods are provided to reduce or eliminate the activity of a GS polypeptide of the invention by transforming a plant cell with an expression cassette that expresses a polynucleotide that inhibits the expression of the GS polypeptide. The polynucleotide may inhibit the expression of the GS polypeptide directly, by preventing transcription or translation of the GS messenger RNA, or indirectly, by encoding a polypeptide that inhibits the transcription or translation of a GS gene encoding a GS polypeptide. Methods for inhibiting or eliminating the expression of a gene in a plant are well known in the art, and any such method may be used in the present invention to inhibit the expression of a GS polypeptide.

In accordance with the present invention, the expression of a GS polypeptide is inhibited if the protein level of the GS polypeptide is less than 70% of the protein level of the same GS polypeptide in a plant that has not been genetically modified or mutagenized to inhibit the expression of that GS polypeptide. In particular embodiments of the invention, the protein level of the GS polypeptide in a modified plant according to the invention is less than 60%, less than 50%, less than 40%, less than 30%, less than 20%, less than 10%, less than 5% or less than 2% of the protein level of the same GS polypeptide in a plant that is not a mutant or that has not been genetically modified to inhibit the expression of that GS polypeptide. The expression level of the GS polypeptide may be measured directly, for example, by assaying for the level of GS polypeptide expressed in the plant cell or plant, or indirectly, for example, by measuring the GS enzyme activity of the GS polypeptide in the plant cell or plant or by measuring the GS in the plant. Methods for performing such assays are described elsewhere herein.

In other embodiments of the invention, the activity of the GS polypeptides is reduced or eliminated by transforming a plant cell with an expression cassette comprising a polynucleotide encoding a polypeptide that inhibits the activity of a GS polypeptide. The GS enzyme activity of a GS polypeptide is inhibited according to the present invention if the GS enzyme activity of the GS polypeptide is less than 70% of the GS enzyme activity of the same GS polypeptide in a plant that has not been modified to inhibit the GS enzyme activity of that GS polypeptide. In particular embodiments of the invention, the GS enzyme activity of the GS polypeptide in a modified plant according to the invention is less than 60%, less than 50%, less than 40%, less than 30%, less than 20%, less than 10% or less than 5% of the GS enzyme activity of the same GS polypeptide in a plant that that has not been modified to inhibit the expression of that GS polypeptide. The GS enzyme activity of a GS polypeptide is "eliminated" according to the invention when it is not detectable by the assay methods described elsewhere herein. Methods of determining the GS enzyme activity of a GS polypeptide are described elsewhere herein.

In other embodiments, the activity of a GS polypeptide may be reduced or eliminated by disrupting the gene encoding the GS polypeptide. The invention encompasses mutagenized plants that carry mutations in GS genes, where the mutations reduce expression of the GS gene or inhibit the GS enzyme activity of the encoded GS polypeptide.

Thus, many methods may be used to reduce or eliminate the activity of a GS polypeptide. In addition, more than one method may be used to reduce the activity of a single GS polypeptide. Non-limiting examples of methods of reducing or eliminating the expression of GS polypeptides are given below.

1. Polynucleotide-Based Methods:

In some embodiments of the present invention, a plant is transformed with an expression cassette that is capable of expressing a polynucleotide that inhibits the expression of a GS polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one GS polypeptide is an expression cassette capable of producing an RNA molecule that inhibits the transcription and/or translation of at least one GS polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a GS polypeptide are given is below.

i. Sense Suppression/Cosuppression

In some embodiments of the invention, inhibition of the expression of a GS polypeptide may be obtained by sense suppression or cosuppression. For cosuppression, an expression cassette is designed to express an RNA molecule corresponding to all or part of a messenger RNA encoding a GS polypeptide in the "sense" orientation. Over expression of the RNA molecule can result in reduced expression of the native gene. Accordingly, multiple plant lines transformed with the cosuppression expression cassette are screened to identify those that show the greatest inhibition of GS polypeptide expression.

The polynucleotide used for cosuppression may correspond to all or part of the sequence encoding the GS polypeptide, all or part of the 5' and/or 3' untranslated region of a GS polypeptide transcript, or all or part of both the coding sequence and the untranslated regions of a transcript encoding a GS polypeptide. In some embodiments where the polynucleotide comprises all or part of the coding region for the GS polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

ii. Sense Suppression

In some embodiments of the invention, inhibition of the expression of the GS polypeptide may be obtained by sense suppression. For sense suppression, the expression cassette is designed to express an RNA molecule complementary to all or part of a messenger RNA encoding the GS polypeptide. Over expression of the sense RNA molecule can result in reduced expression of the native gene. Accordingly, multiple plant lines transformed with the sense suppression expression cassette are screened to identify those that show the greatest inhibition of GS polypeptide expression.

The polynucleotide for use in sense suppression may correspond to all or part of the complement of the sequence encoding the GS polypeptide, all or part of the complement of the 5' and/or 3' untranslated region of the GS transcript or all or part of the complement of both the coding sequence and the untranslated regions of a transcript encoding the GS polypeptide. In addition, the sense polynucleotide may be fully complementary (i.e., 100% identical to the complement of the target sequence) or partially complementary (i.e., less than 100% identical to the complement of the target sequence) to the target sequence. Sense suppression may be used to inhibit the expression of multiple proteins in the same plant. See, for example, U.S. Pat. No. 5,942,657. Furthermore, portions of the sense nucleotides may be used to disrupt the expression of the target gene. Generally, sequences of at least 50 nucleotides, 100 nucleotides, 200 nucleotides, 300, 400, 450, 500, 550 or greater may be used. Methods for using sense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of sense suppression may be increased by including a poly-dT region in the expression cassette at a position 3' to the sense sequence and 5' of the polyadenylation signal. See, US Patent Application Publication Number 2002/0048814, herein incorporated by reference.

iii. Double-Stranded RNA Interference

In some embodiments of the invention, inhibition of the expression of a GS polypeptide may be obtained by double-stranded RNA (dsRNA) interference. For dsRNA interference, a sense RNA molecule like that described above for cosuppression and a anti-sense RNA molecule that is fully or partially complementary to the sense RNA molecule are expressed in the same cell, resulting in inhibition of the expression of the corresponding endogenous messenger RNA.

Expression of the sense and sense molecules can be accomplished by designing the expression cassette to comprise both a sense sequence and a sense sequence. Alternatively, separate expression cassettes may be used for the sense and sense sequences. Multiple plant lines transformed with the dsRNA interference expression cassette or expression cassettes are then screened to identify plant lines that show the greatest inhibition of GS polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743 and WO 1999/49029, WO 99/53050, WO 99/61631 and WO 00/49035, each of which is herein incorporated by reference.

iv. Hairpin RNA Interference and Intron-Containing Hairpin RNA Interference

In some embodiments of the invention, inhibition of the expression of a GS polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited and a sense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini, et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference.

The expression cassette for hpRNA interference may also be designed such that the sense sequence and the sense sequence do not correspond to an endogenous RNA. In this embodiment, the sense and sense sequence flank a loop sequence that comprises a nucleotide sequence corresponding to all or part of the endogenous messenger RNA of the target gene. Thus, it is the loop region that determines the specificity of the RNA interference. See, for example, WO 02/00904, Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci.*, USA 99:13659-13662; Aufsaftz, et al., (2002) *Proc. Natl. Acad. Sci.* 99(4): 16499-16506; Sijen, et al., *Curr. Biol.* (2001) 11:436-440), herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or sense relative to the target sequence (i.e., the messenger RNA for the GS polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of the GS polypeptide. Thus, the polynucleotide causes the degradation of the endogenous messenger RNA, resulting in reduced expression of the GS polypeptide. This method is described, for example, in U.S. Pat. No. 4,987,071, herein incorporated by reference.

vii. Small Interfering RNA or Micro RNA

In some embodiments of the invention, inhibition of the expression of a GS polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of GS expression, the 22-nucleotide sequence is selected from a GS transcript sequence and contains 22 nucleotides of said GS sequence in sense orientation and 21 nucleotides of a corresponding sense sequence that is complementary to the sense sequence. miRNA molecules are highly efficient at inhibiting the expression of endogenous genes and the RNA interference they induce is inherited by subsequent generations of plants.

2. Polypeptide-Based Inhibition of Gene Expression

In one embodiment, the polynucleotide encodes a GS protein that binds to a gene encoding a GS polypeptide, resulting in reduced expression of the gene. In particular embodiments, the GS protein binds to a regulatory region of a GS gene. In other embodiments, the GS protein binds to a messenger RNA encoding a GS polypeptide and prevents its translation. Methods of selecting sites for targeting by GS proteins have been described, for example, in U.S. Pat. No. 6,453,242, and methods for using GS proteins to inhibit the expression of genes in plants are described, for example, in US Patent Application Publication Number 2003/0037355, each of which is herein incorporated by reference.

3. Polypeptide-Based Inhibition of Protein Activity

In some embodiments of the invention, the polynucleotide encodes an antibody that binds to at least one GS polypeptide and reduces the GS enzyme activity of the GS polypeptide. In another embodiment, the binding of the antibody results in increased turnover of the antibody-GS complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of a GS polypeptide is reduced or eliminated by disrupting the gene encoding the GS polypeptide. The gene encoding the GS polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced GS enzyme activity.

i. Transposon Tagging

In one embodiment of the invention, transposon tagging is used to reduce or eliminate the GS activity of one or more GS polypeptide. Transposon tagging comprises inserting a transposon within an endogenous GS gene to reduce or eliminate expression of the GS polypeptide. "GS gene" is intended to mean the gene that encodes a GS polypeptide according to the invention.

In this embodiment, the expression of one or more GS polypeptide is reduced or eliminated by inserting a transposon within a regulatory region or coding region of the gene encoding the GS polypeptide. A transposon that is within an exon, intron, 5' or 3' untranslated sequence, a promoter or any other regulatory sequence of a GS gene may be used to reduce or eliminate the expression and/or activity of the encoded GS polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764, each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see, Ohshima, et al., (1998) *Virology* 243:472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (GS enzyme activity) of the encoded protein are well known in the art. Insertional mutations in gene exons usually result in null-mutants. Mutations in conserved residues are particularly effective in inhibiting the GS enzyme activity of the encoded protein. Conserved residues of plant GS polypeptides suitable for mutagenesis with the goal to eliminate GS enzyme activity have been described. Such mutants can be isolated according to well-known procedures, and mutations in different GS loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more GS polypeptide. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. See also, WO 98/49350, WO 99/07865, WO 99/25821 and Beetham, et al., (1999) *Proc. Natl. Acad. Sci. USA* 96:8774-8778, each of which is herein incorporated by reference.

iii. Modulating GS Enzyme Activity

In specific methods, the level and/or activity of a GS regulator in a plant is decreased by increasing the level or activity of the GS polypeptide in the plant. Methods for increasing the level and/or activity of GS polypeptides in a plant are discussed elsewhere herein. Briefly, such methods comprise providing a GS polypeptide of the invention to a plant and thereby increasing the level and/or activity of the GS polypeptide. In other embodiments, a GS nucleotide sequence encoding a GS polypeptide can be provided by introducing into the plant a polynucleotide comprising a GS nucleotide sequence of the invention, expressing the GS sequence, increasing the activity of the GS polypeptide and thereby decreasing the ammonium uptake or transport in the plant or plant part. In other embodiments, the GS nucleotide construct introduced into the plant is stably incorporated into the genome of the plant.

As discussed above, one of skill will recognize the appropriate promoter to use to modulate the level/activity of a GS enzyme in the plant. Exemplary promoters for this embodiment have been disclosed elsewhere herein.

Accordingly, the present invention further provides plants having a modified number of cells when compared to the number of cells of a control plant tissue. In one embodiment, the plant of the invention has an increased level/activity of the GS polypeptide of the invention and thus has an increased Ammonium transport in the plant tissue. In other embodiments, the plant of the invention has a reduced or eliminated level of the GS polypeptide of the invention and thus has an increased NUE in the plant tissue. In other embodiments, such plants have stably incorporated into their genome a nucleic acid molecule comprising a GS nucleotide sequence of the invention operably linked to a promoter that drives expression in the plant cell.

iv. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development or radial expansion.

Methods for modulating root development in a plant are provided. The methods comprise modulating the level and/or activity of the GS polypeptide in the plant. In one method, a GS sequence of the invention is provided to the plant. In another method, the GS nucleotide sequence is provided by introducing into the plant a polynucleotide comprising a GS nucleotide sequence of the invention, expressing the GS sequence and thereby modifying root development. In still other methods, the GS nucleotide construct introduced into the plant is stably incorporated into the genome of the plant.

In other methods, root development is modulated by altering the level or activity of the GS polypeptide in the plant. A decrease in GS activity can result in at least one or more of the following alterations to root development, including, but not limited to, larger root meristems, increased in root growth, enhanced radial expansion, an enhanced vasculature system, increased root branching, more adventitious roots and/or an increase in fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by decreasing the activity and/or level of the GS polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass by decreasing the level and/or activity of the GS polypeptide also finds use in promoting in vitro propagation of explants.

Furthermore, higher root biomass production due to a decreased level and/or activity of GS activity has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

Accordingly, the present invention further provides plants having modulated root development when compared to the root development of a control plant. In some embodiments, the plant of the invention has an increased level/activity of the GS polypeptide of the invention and has enhanced root growth and/or root biomass. In other embodiments, such plants have stably incorporated into their genome a nucleic acid molecule comprising a GS nucleotide sequence of the invention operably linked to a promoter that drives expression in the plant cell.

v. Modulating Shoot and Leaf Development

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and US Patent Application Publication Number 2003/0074698, each of which is herein incorporated by reference.

The method for modulating shoot and/or leaf development in a plant comprises modulating the activity and/or level of a GS polypeptide of the invention. In one embodiment, a GS sequence of the invention is provided. In other embodiments, the GS nucleotide sequence can be provided by introducing into the plant a polynucleotide comprising a GS nucleotide sequence of the invention, expressing the GS sequence and thereby modifying shoot and/or leaf development. In other embodiments, the GS nucleotide construct introduced into the plant is stably incorporated into the genome of the plant.

In specific embodiments, shoot or leaf development is modulated by increasing the level and/or activity of the GS polypeptide in the plant. An increase in GS activity can result in at least one or more of the following alterations in shoot and/or leaf development, including, but not limited to, leaf number, leaf surface, vasculature, internode length and leaf senescence, when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters and leaf-preferred promoters. Exemplary promoters have been disclosed elsewhere herein.

As discussed above, modulation GS activity in the plant modulates both root and shoot growth. Thus, the present invention further provides methods for altering the root/shoot ratio. Shoot or leaf development can further be modulated by decreasing the level and/or activity of the GS polypeptide in the plant.

Accordingly, the present invention further provides plants having modulated shoot and/or leaf development when compared to a control plant. In some embodiments, the plant of the invention has an increased level/activity of the GS polypeptide of the invention. In other embodiments, the plant of the invention has a decreased level/activity of the GS polypeptide of the invention.

vi Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the GS polypeptide has not been modulated. "Modulating floral development" further includes any alteration in the timing of the development of a plant's reproductive tissue (i.e., a delayed or a accelerated timing of floral development) when compared to a control plant in which the activity or level of the GS polypeptide has not been modulated. Macroscopic alterations may include changes in size, shape, number or location of reproductive organs, the developmental time period that these structures form or the ability to maintain or proceed through the flowering process in times of environmental stress. Microscopic alterations may include changes to the types or shapes of cells that make up the reproductive organs.

The method for modulating floral development in a plant comprises modulating GS activity in a plant. In one method, a GS sequence of the invention is provided. A GS nucleotide sequence can be provided by introducing into the plant a polynucleotide comprising a GS nucleotide sequence of the invention, expressing the GS sequence, and thereby modifying floral development. In other embodiments, the GS nucleotide construct introduced into the plant is stably incorporated into the genome of the plant.

In specific methods, floral development is modulated by increasing the level or activity of the GS polypeptide in the plant. An increase in GS activity can result in at least one or more of the following alterations in floral development, including, but not limited to, retarded flowering, reduced number of flowers, partial male sterility and reduced seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S111-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters and inflorescence-preferred promoters.

In other methods, floral development is modulated by decreasing the level and/or activity of the GS sequence of the invention. Such methods can comprise introducing a GS nucleotide sequence into the plant and decreasing the activity of the GS polypeptide. In other methods, the GS nucleotide construct introduced into the plant is stably incorporated into the genome of the plant. Decreasing expression of the GS sequence of the invention can modulate floral development during periods of stress. Such methods are described elsewhere herein. Accordingly, the present invention further provides plants having modulated floral development when compared to the floral development of a control plant. Compositions include plants having a decreased level/activity of the GS polypeptide of the invention and having an altered floral development. Compositions also include plants having a decreased level/activity of the GS polypeptide of the invention wherein the plant maintains or proceeds through the flowering process in times of stress.

Methods are also provided for the use of the GS sequences of the invention to increase nitrogen use efficiency. The method comprises decreasing or increasing the activity of the GS sequences in a plant or plant part, such as the roots, shoot, epidermal cells, etc.

As discussed above, one of skill will recognize the appropriate promoter to use to manipulate the expression of GS. Exemplary promoters of this embodiment include constitutive promoters, inducible promoters, and root or shoot or leaf preferred promoters.

vii. Method of Use for GS Promoter Polynucleotides

The polynucleotides comprising the GS promoters disclosed in the present invention, as well as variants and fragments thereof, are useful in the genetic manipulation of any host cell, preferably plant cell, when assembled with a DNA construct such that the promoter sequence is operably linked to a nucleotide sequence comprising a polynucleotide of interest. In this manner, the GS promoter polynucleotides of the invention are provided in expression cassettes along with a polynucleotide sequence of interest for expression in the host cell of interest. GS promoter sequences of the invention are expressed in a variety of tissues and thus the promoter sequences can find use in regulating the temporal and/or the spatial expression of polynucleotides of interest.

Synthetic hybrid promoter regions are known in the art. Such regions comprise upstream promoter elements of one polynucleotide operably linked to the promoter element of another polynucleotide. In an embodiment of the invention, heterologous sequence expression is controlled by a synthetic hybrid promoter comprising the GS promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton, et al., (1998) *Curr. Opin. Plant Biol.* 1:311-315. Alternatively, a synthetic GS promoter sequence may comprise duplications of the upstream promoter elements found within the GS promoter sequences.

It is recognized that the promoter sequence of the invention may be used with its native GS coding sequences. A DNA construct comprising the GS promoter operably linked with its native GS gene may be used to transform any plant of interest to bring about a desired phenotypic change, such as, modulating root, shoot, leaf, floral and embryo development, stress tolerance and any other phenotype described elsewhere herein.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as GSs, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics and commercial products. Genes of interest include, generally, those involved in oil, starch, carbohydrate or nutrient metabolism as well as those affecting kernel size, sucrose loading and the like.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802 and 5,703,409); barley high lysine (Williamson, et al., (1987) *Eur. J. Biochem.* 165:99-106 and WO 98/20122) and high methionine proteins (Pedersen, et al., (1986) *J. Biol. Chem.* 261: 6279; Kirihara, et al., (1988) *Gene* 71:359 and Musumura, et al., (1989) *Plant Mol. Biol.* 12: 123)); increased digestibility (e.g., modified storage proteins (U.S. patent application Ser. No. 10/053,410, filed Nov. 7, 2001) and thioredoxins (U.S. patent application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene) and glyphosate resistance (EPSPS gene)) and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)) and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see, U.S. Pat. No. 5,583,210), stalk strength, flowering time or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane H⁺-ATPase (MHA2) (Frias, et al., (1996) *Plant Cell* 8:1533-44); AKT1, a component of the potassium uptake apparatus in *Arabidopsis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem* 27:16749-16752, Arredondo-Peter, et al., (1997) *Plant Physiol.* 115:1259-1266; Arredondo-Peter, et al., (1997) *Plant Physiol* 114:493-500 and references sited therein). The sequence of interest may also be useful in expressing sense nucleotide sequences of genes that that negatively affects root development.

Additional, agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802 and 5,990, 389, herein incorporated by reference. Another example is lysine and/or sulfur rich seed protein encoded by the soybean 2S albumin described in U.S. Pat. No. 5,850,016 and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. patent application Ser. No. 08/740,682, filed Nov. 1, 1996 and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359; both of which are herein incorporated by reference) and rice (Musumura, et al., (1989) *Plant Mol. Biol.* 12:123, herein incorporated by reference). Other agronomically important genes encode latex, Floury 2, growth factors, seed storage factors and transcription factors.

Insect resistance genes may encode resistance to pests that have great yield drag such as rootworm, cutworm, European Corn Borer and the like. Such genes include, for example, *Bacillus thuringiensis* toxic protein genes (U.S. Pat. Nos. 5,366,892; 5,747,450; 5,736,514; 5,723,756; 5,593,881 and Geiser, et al., (1986) *Gene* 48:109), and the like.

Genes encoding disease resistance traits include detoxification genes, such as against fumonosin (U.S. Pat. No. 5,792,931); avirulence (avr) and disease resistance (R) genes (Jones, et al., (1994) *Science* 266:789; Martin, et al., (1993) *Science* 262:1432 and Mindrinos, et al., (1994) *Cell* 78:1089), and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene) or other such genes known in the art. The bar gene encodes resistance to the herbicide basta, the nptII gene encodes resistance to the antibiotics kanamycin and geneticin and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802 and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase) and acetoacetyl-CoA reductase (see, Schubert, et al., (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones and the like. The level of proteins, particularly modified proteins having improved amino acid distribution to improve the nutrient value of the plant, can be increased. This is achieved by the expression of such proteins having enhanced amino acid content.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1

Figure 1A:
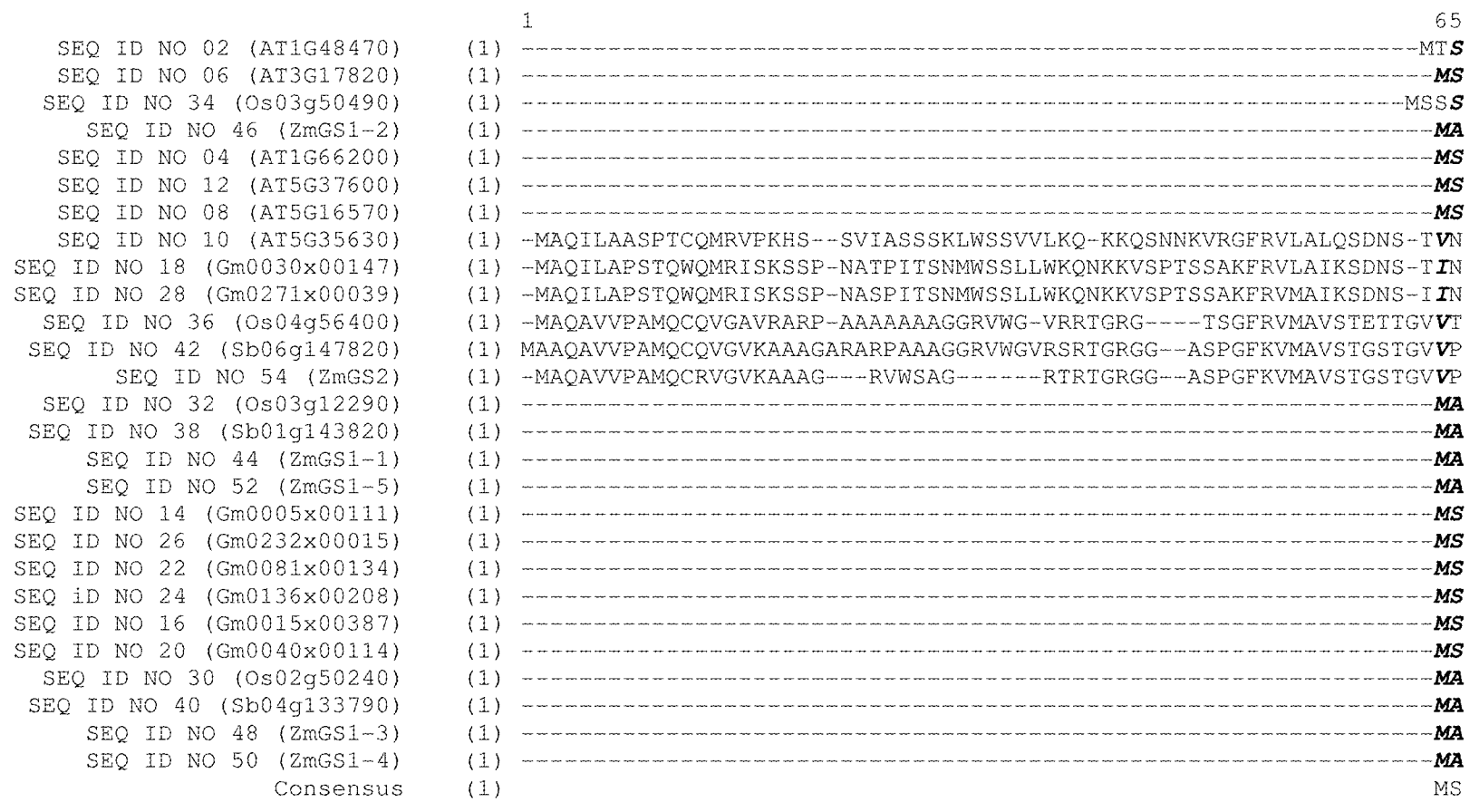
Figure 1C:
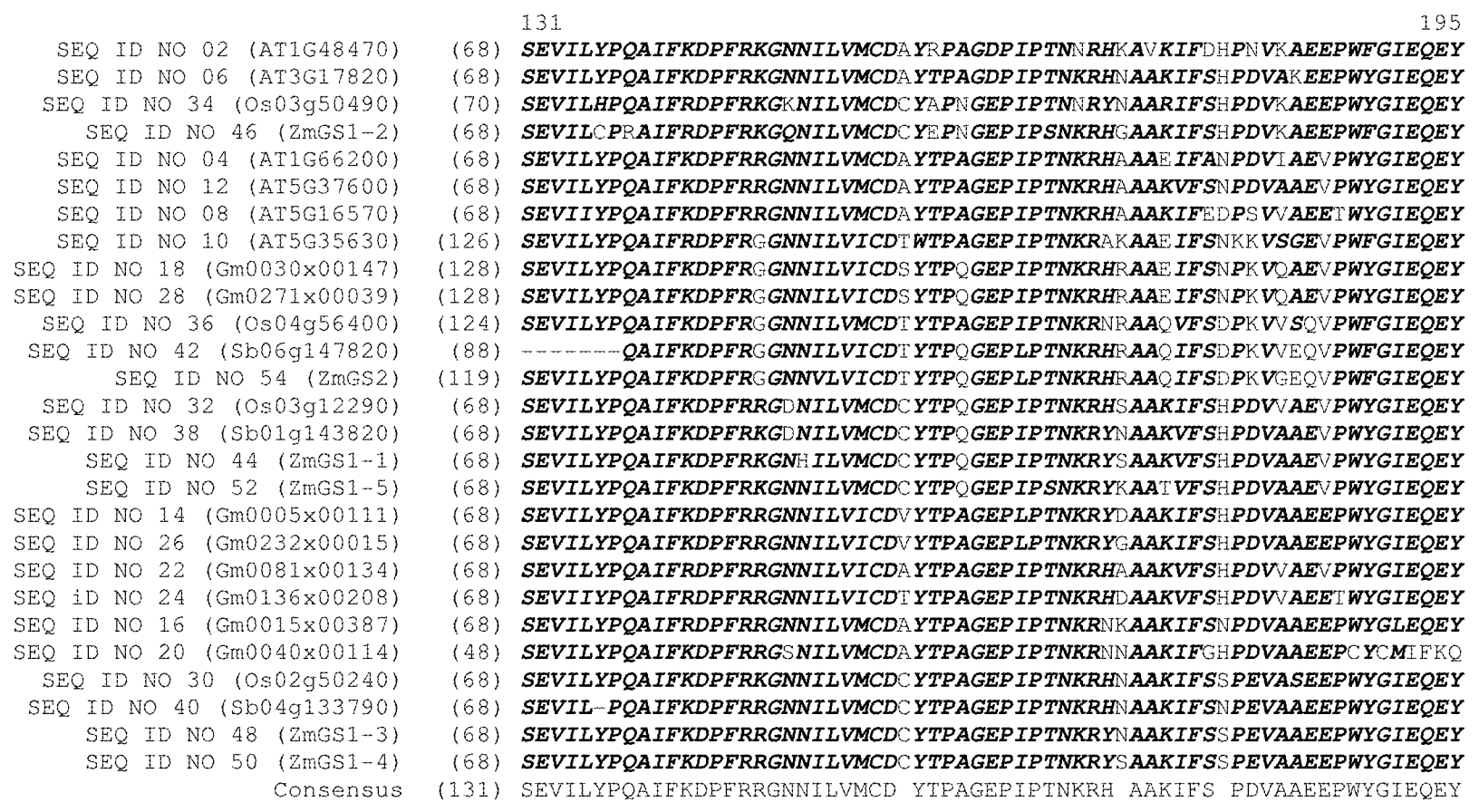
Figure 1I:
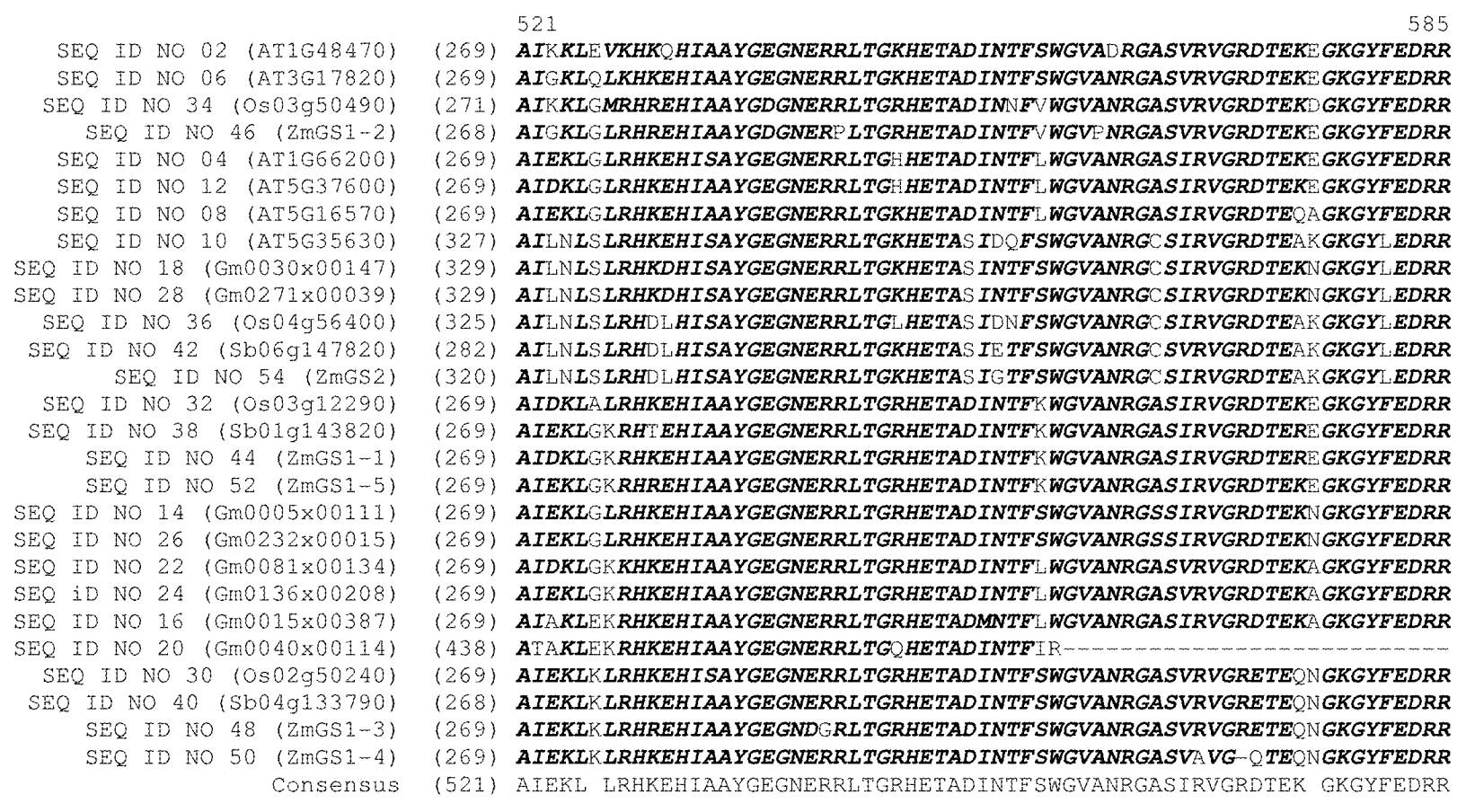

Identification and Phylogenetic Analyses of GS Sequences from *Arabidopsis*, Soybean, Rice, Sorghum and Maize A routine for identifying all members of a given species' glutamine synthetase (GS) gene family was employed. First, a diverse set of the known available members of the gene family as protein sequences was prepared from public and proprietary sources. Then, as in the example of maize, these protein query sequences were searched using a BLAST algorithm against a combination of proprietary and public genomic or transcript, nucleotide sequence datasets and a non-redundant set of candidate GS or 'hits' was identified. These sequences were combined with any existing maize gene family sequences, and then curated and edited to arrive at a new working set of unique maize GS gene or transcript sequences and their translations. This search for gene family members was repeated. If new sequences were recovered that were unique (not same-gene matches), the process was repeated until completion, that is until no new and distinct nucleotide sequences were found. In this way it was determined that the maize GS gene family consisted of 6 members. Eight and 3 distinct soybean and sorghum sequences were found, respectively. Without the complete genome sequences of maize or soybean available, researchers were less certain of the exact gene family size, than they were for *Arabidopsis* (6 members) and rice (4 members). The availability of complete genome sequences for *Arabidopsis* and rice simplified the search, aided also by availability of fairly mature gene models and annotations for these species. All the Sequence IDs along with the annotation identity were cataloged in Table 1. The polypeptide alignment of all 27 sequences is shown in FIG. 1. Several regions of very high homology were identified by this alignment. All these polypeptides from different species (except SEQ ID NO: 20) show a sequence identity in the range of 70-95% among different members. Due to several insertions, SEQ ID NO: 20 show an identity in the range of 53-74% with different GS polypeptides from different species. SEQ ID NOS: 10, 18, 28, 36, 42 and 54 belong to the GS2 group (chloroplast-localized) as in all the polypeptides a clear chloroplast targeting peptide was identified. Phylogenetic analyses of all 27 polypeptides are shown in FIG. 2. Clearly, ZMGS1-1/1-5, ZMGS1-3/1-4, ZMGS1-2 and ZMGS2 along with members from other species were clustered in four different clades. There seems a soybean specific clade with SEQ ID NOS: 14, 22, 24 and 26.

Example 2

MPSS Expression Analyses of Different GS Isoforms from Maize

Figure 3B:
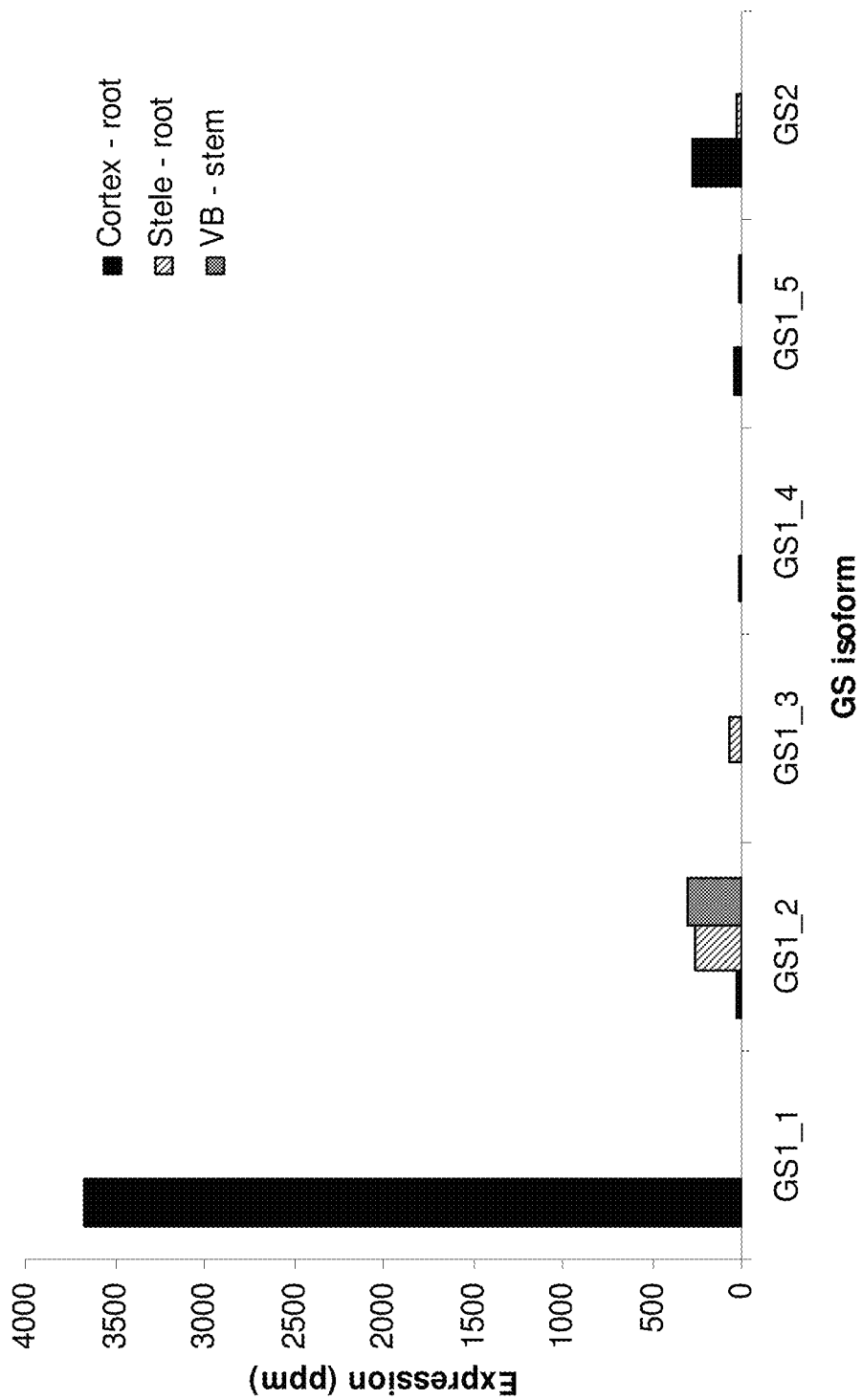
Figure 3C:
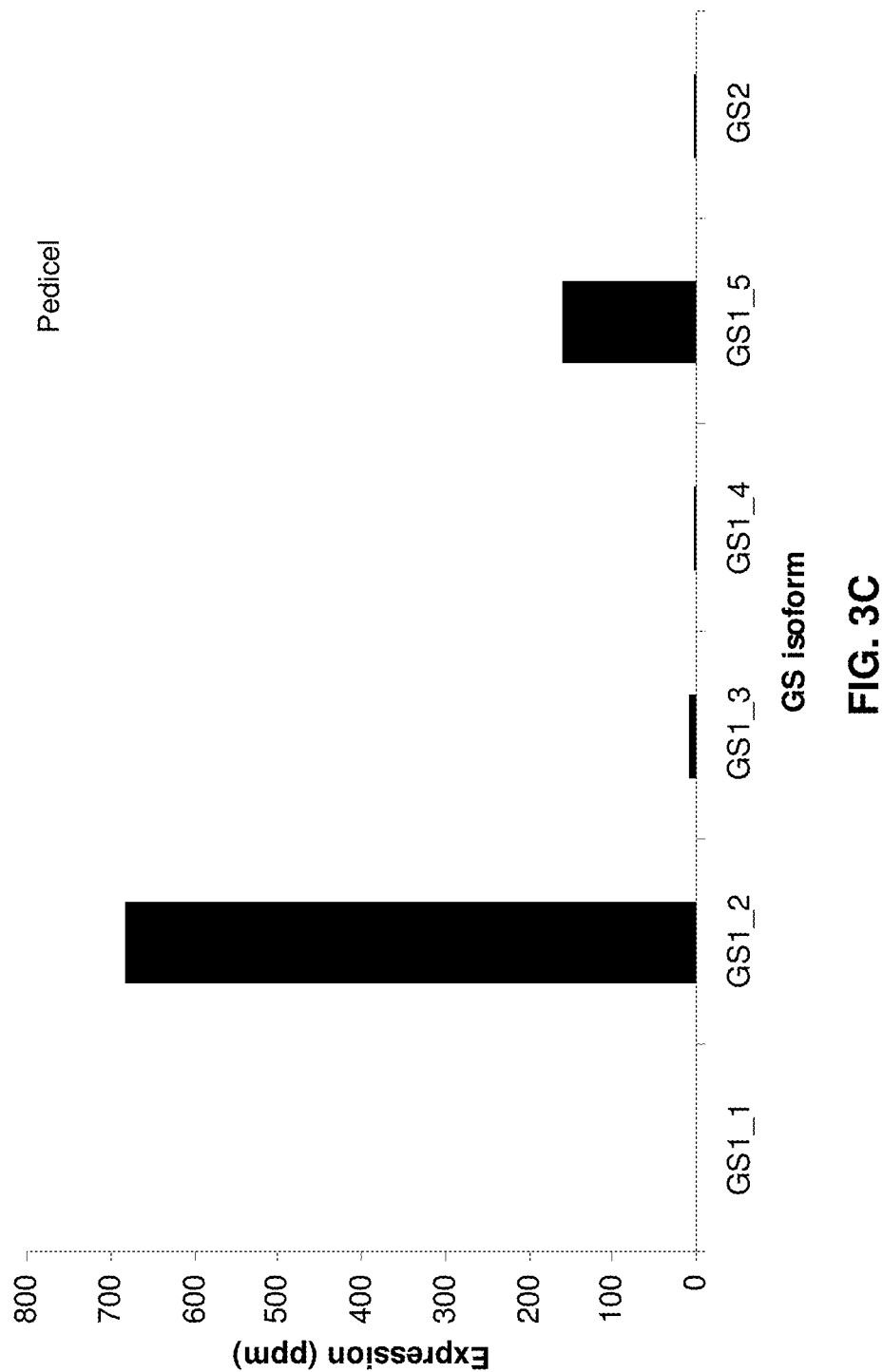

Massively Parallel Signature Sequencing (MPSS) expression analyses were performed for expression of GS isoforms from a maize database consisting of more than 300 tissue libraries. The results from these analyses are summarized in FIG. 3. GS1-1 and GS2 were expressed predominantly in roots and leaves, respectively (FIG. 3, top panel). GS1-2 expresses more or less in all the tissues with a slightly higher expression in the pollen (FIG. 3, top panel). GS1-3 and 1-4 are expressed at very low levels in most of the tissues examined whereas GS1-5 expresses at ~100 ppm (parts per million) in the roots (FIG. 3, top panel). GS1-1 showed 15-20-fold higher level expression in the root-cortex as compared to other isoforms (FIG. 3, middle panel). Among all the isoforms, only GS1-2 and 1-5 are expressed in the pedicel (FIG. 3, bottom panel)

Example 3

Transformation and Regeneration of Transgenic Plants by *Agrobacterium*-Mediated Transformation Several vectors were transformed in maize (FAST/GS3xGF or ETX inbred) by *Agrobacterium* mediated transformation. The description of these vectors is provided in Table 2.

TABLE 2

| PHP | ZmGS Isoform | Promoter | Promoter Specificity | Target Genotype |
|---|---|---|---|---|
| 32754 | GS1-1 | Ubiquitin | Constitutive | FAST (GS3xGF) |
| 32794 | GS1-1 | RM2 | Roots | FAST (GS3xGF) |
| 32781 | GS1-2 | Ubiquitin | Constitutive | FAST (GS3xGF) |
| 32786 | GS1-2 | RM2 | Roots | FAST (GS3xGF) |
| 32760 | GS1-3 | Ubiquitin | Constitutive | FAST (GS3xGF) |
| 32779 | GS1-3 | RM2 | Roots | FAST (GS3xGF) |
| 32753 | GS1-4 | Ubiquitin | Constitutive | FAST (GS3xGF) |
| 32772 | GS1-4 | RM2 | Roots | FAST (GS3xGF) |
| 32755 | GS1-5 | Ubiquitin | Constitutive | FAST (GS3xGF) |
| 32743 | GS1-5 | RM2 | Roots | FAST (GS3xGF) |
| 32007 | GS1-3 | Ubiquitin | Constitutive | Inbred (ETX) |
| 32006 | GS1-3 | RM2 | Roots | Inbred (ETX) |
| 32005 | GS1-3 | SSU | leaf (bundlesheath) | Inbred (ETX) |
| 32008 | GS1-3 | PEPC | leaf (mesophyl) | Inbred (ETX) |
| 38267 | GS1-4 | Ubiquitin | Constitutive | Inbred (ETX) |
| 38268 | GS1-4 | RM2 | Roots | Inbred (ETX) |
| 38269 | GS1-4 | PEPC | leaf (mesophyl) | Inbred (ETX) |
| 38930 | GS1-5 | Ubiquitin | Constitutive | Inbred (ETX) |
| 38931 | GS1-5 | RM2 | Roots | Inbred (ETX) |
| 38932 | GS1-5 | PEPC | leaf (mesophyl) | Inbred (ETX) |

For *Agrobacterium*-mediated transformation of maize with a sense sequence of the GS sequence of the present invention, preferably the method of Zhao is employed (U.S. Pat. No. 5,981,840 and PCT Patent Publication WO98/32326, the contents of which are hereby incorporated by reference). Briefly, immature embryos are isolated from maize and the embryos contacted with a suspension of *Agrobacterium*, where the bacteria are capable of transferring the sense GS sequences to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants. Plants are monitored and scored for a modulation in tissue development.

Immature maize embryos from greenhouse donor plants are bombarded with a plasmid containing the GS sequence operably linked to constitutive or tissue specific promoter (Vilardell, et al., (1990) *Plant Mol Biol* 14:423-432) and the selectable marker gene PAT, which confers resistance to the herbicide Bialaphos. Alternatively, the selectable marker gene is provided on a separate plasmid. Transformation is performed as follows. Media recipes follow below.

Preparation of Target Tissue:

The ears are husked and surface sterilized in 30% Clorox@ bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA:

A plasmid vector comprising the GS sequence operably linked to an ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment:

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment:

Following bombardment, the embryos are kept on 560Y medium for 2 days, then transferred to 560R selection medium containing 3 mg/liter Bialaphos and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for increased drought tolerance. Assays to measure improved drought tolerance are routine in the art and include, for example, increased kernel-earring capacity yields under drought conditions when compared to control maize plants under identical environmental conditions. Alternatively, the transformed plants can be monitored for a modulation in meristem development (i.e., a decrease in spikelet formation on the ear). See, for example, Bruce, et al., (2002) *Journal of Experimental Botany* 53:1-13.

Bombardment and Culture Media:

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D and 2.88 g/l L-proline (brought to volume with D-I $H_2O$ following adjustment to pH 5.8 with KOH); 2.0 g/l Gelrite® (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite® (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose and 1.0 ml/l of 0.1 mM abscisic acid (brought to volume with polished D-I $H_2O$ after adjusting to pH 5.6); 3.0 g/l Gelrite® (added after bringing to volume with D-I $H_2O$) and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol and 40.0 g/l sucrose (brought to volume with polished D-I $H_2O$ after adjusting pH to 5.6) and 6 g/l Bacto™-agar (added after bringing to volume with polished D-I $H_2O$), sterilized and cooled to 60° C.

Example 4

Soybean Embryo Transformation

Soybean embryos are bombarded with a plasmid containing a sense GS sequences operably linked to an ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The expression cassette comprising a sense GS sequence operably linked to the ubiquitin promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1

M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 5

Sunflower Meristem Tissue Transformation

Sunflower meristem tissues are transformed with an expression cassette containing a sense GS sequences operably linked to a ubiquitin promoter as follows (see also, EP Patent Number 0 486233, herein incorporated by reference and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% Clorox® bleach solution with the addition of two drops of Tween® 20 per 50 ml of solution. The seeds are rinsed twice with sterile distilled water.

Split embryonic axis explants are prepared by a modification of procedures described by Schrammeijer, et al., (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.*, 15:473-497), Shepard's vitamin additions (Shepard, (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA$_3$), pH 5.6 and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the GS gene operably linked to the ubiquitin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bacto® peptone and 5 gm/l NaCl, pH 7.0) with the appropriate antibiotics required for bacterial strain and binary plasmid maintenance. The suspension is used when it reaches an OD$_{600}$ of about 0.4 to 0.8. The *Agrobacterium* cells are pelleted and resuspended at a final OD$_{600}$ of 0.5 in an inoculation medium comprised of 12.5 mM MES pH 5.7, 1 gm/l NH$_4$Cl and 0.3 gm/l MgSO$_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in meristem development (i.e., an alteration of size and appearance of shoot and floral meristems).

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% Gelrite®, pH 5.6) and grown under conditions described for explant culture. The upper portion of the seedling is removed, a 1 cm vertical slice is made in the hypocotyl, and the transformed shoot inserted into the cut. The entire area is wrapped with Parafilm® to secure the shoot. Grafted plants can be transferred to soil following one week of in vitro culture. Grafts in soil are maintained under high humidity conditions followed by a slow acclimatization to the greenhouse environment. Transformed sectors of T0 plants (parental generation) maturing in the greenhouse are identified by NPTII ELISA and/or by GS activity analysis of leaf extracts while transgenic seeds harvested from NPTII-positive T0 plants are identified by GS activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox® bleach solution with the addition of two to three drops of Tween® 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar) and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bacto® peptone and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at $OD_{600}$. Particle-bombarded explants are transferred to GBA medium (374E) and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for a modulation in meristem development (i.e., an alteration of size and appearance of shoot and floral meristems). After positive (i.e., a decrease in GS expression) explants are identified, those shoots that fail to exhibit a decrease in GS activity are discarded and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for a decreased GS expression are grafted to Pioneer hybrid 6440 in vitro-grown sunflower seedling rootstock. The rootstocks are prepared in the following manner. Seeds are dehulled and surface-sterilized for 20 minutes in a 20% Clorox® bleach solution with the addition of two to three drops of Tween® 20 per 100 ml of solution and are rinsed three times with distilled water. The sterilized seeds are germinated on the filter moistened with water for three days, then they are transferred into 48 medium (half-strength MS salt, 0.5% sucrose, 0.3% Gelrite® pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with Parafilm®. After one week of culture on the medium, grafted plants are transferred to soil. In the first two weeks, they are maintained under high humidity conditions to acclimatize to a greenhouse environment.

Example 6

Molecular Analyses for Transgene Expression

All the transgenic T0 and T1 events were characterized at molecular level by genomic and RT-PCR using transgene specific PCR primers. The single-copy and transgene expressing events were advanced for further experiments. Actin expression was used as an internal control in all the PCR reactions. In most cases transgene expression was as expected from the promoter specificity used for driving the transgene.

Example 7

Glutamine Synthase (GS) Enzyme Activity in Transgenic Plants

Glutamine synthase activity was indirectly measured by the transferase assay shown below.

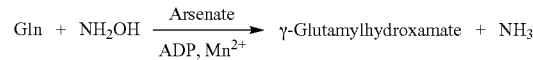

γ-glutamylhydroxamate (γ-GHA) thus produced is measured with acidified $FeCl_3$, which yields a brown color that absorbs maximally at 540 nm wavelength.

Figure 4A:
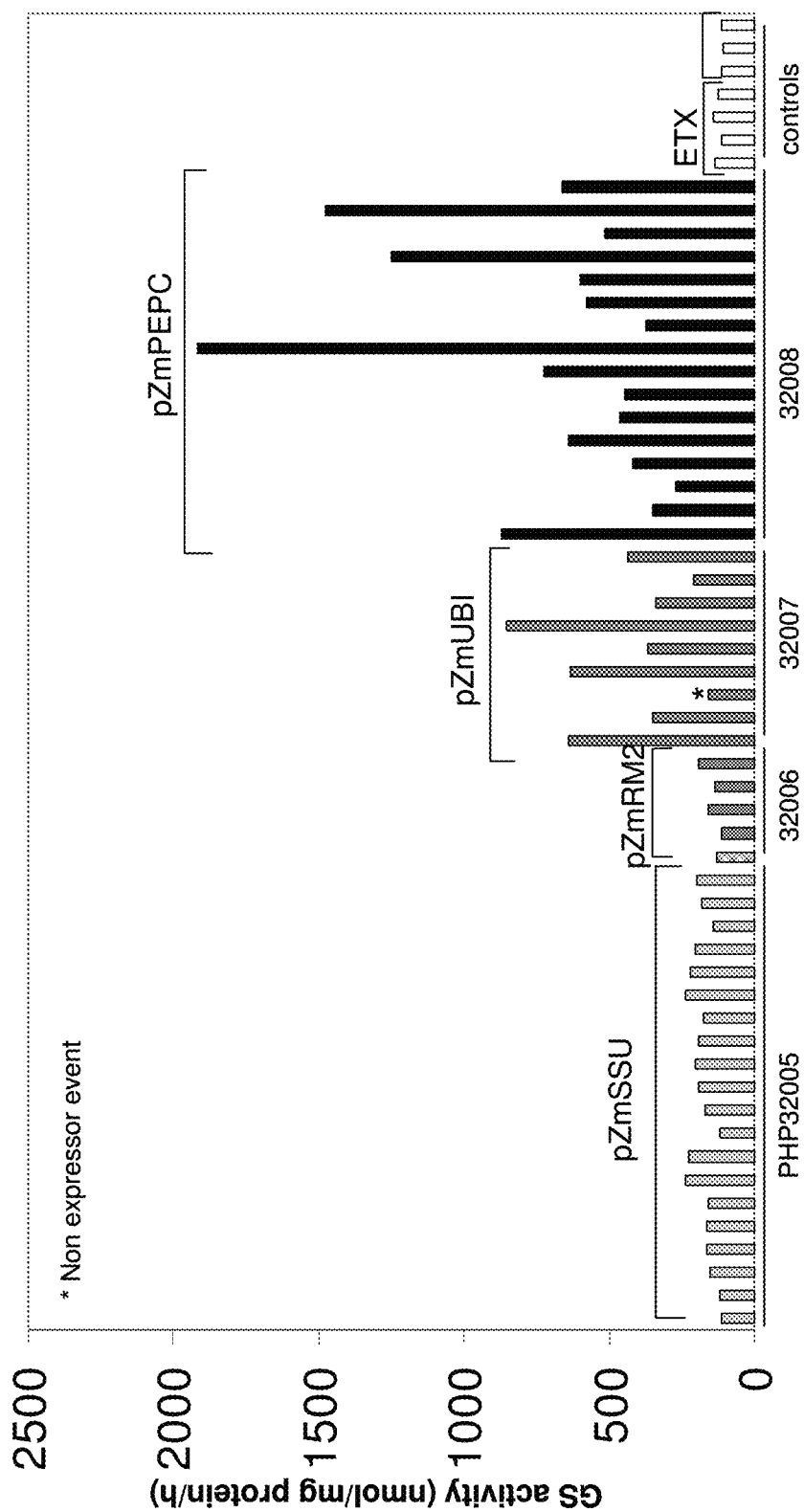
FIG. 4A, FIG. 4B, FIG. 4C, and FIG. 4D GS activity in leaves of T0 events of ETX. GS enzyme activity was determined in the leaves of field-grown T0 inbred (ETX) events transformed with PHP32005, 32006, 32007, 32008, 38267, 28268 and 38269. The results from the individual events (FIG. 4A, FIG. 4C) and average of all the events (FIG. 4B, FIG. 4D) in each construct are summarized. In case of ZM-GS1-3 over-expression PHPs, the highest activity (on an average 12× higher) was observed in PHP32008 (ZmPEPC1 PRO:ZmGS1-3) followed by PHP32007 (ZmUBI PRO:ZmGS1-3) where the activity was slightly higher than the controls in PHP32005 (pZmSSU PRO: ZmGS1-3). In case of PHP32006 (ZmRM2 PRO:ZmGS1-3) leaf samples, the activity was comparable to control as expected as RM2 is a root-preferred promoter. In case of PHP32006, the roots of T1 events showed significantly higher GS activity as compared to non-transgenic sibs. For ZM-GS1-4, the highest GS activity was observed in PHP38269 (pZM-PEPC::ZM-GS1-4) followed by PHP38267 (pZM-UBI::ZM-GS1-4). In case of PHP32268 (ZmRM2 PRO:ZmGS1-4) leaf samples the activity was comparable to control as expected as RM2 is a root-preferred promoter. The average activities of all the events in each construct are summarized in FIG. 4B and FIG. 4D.
Figure 4B:
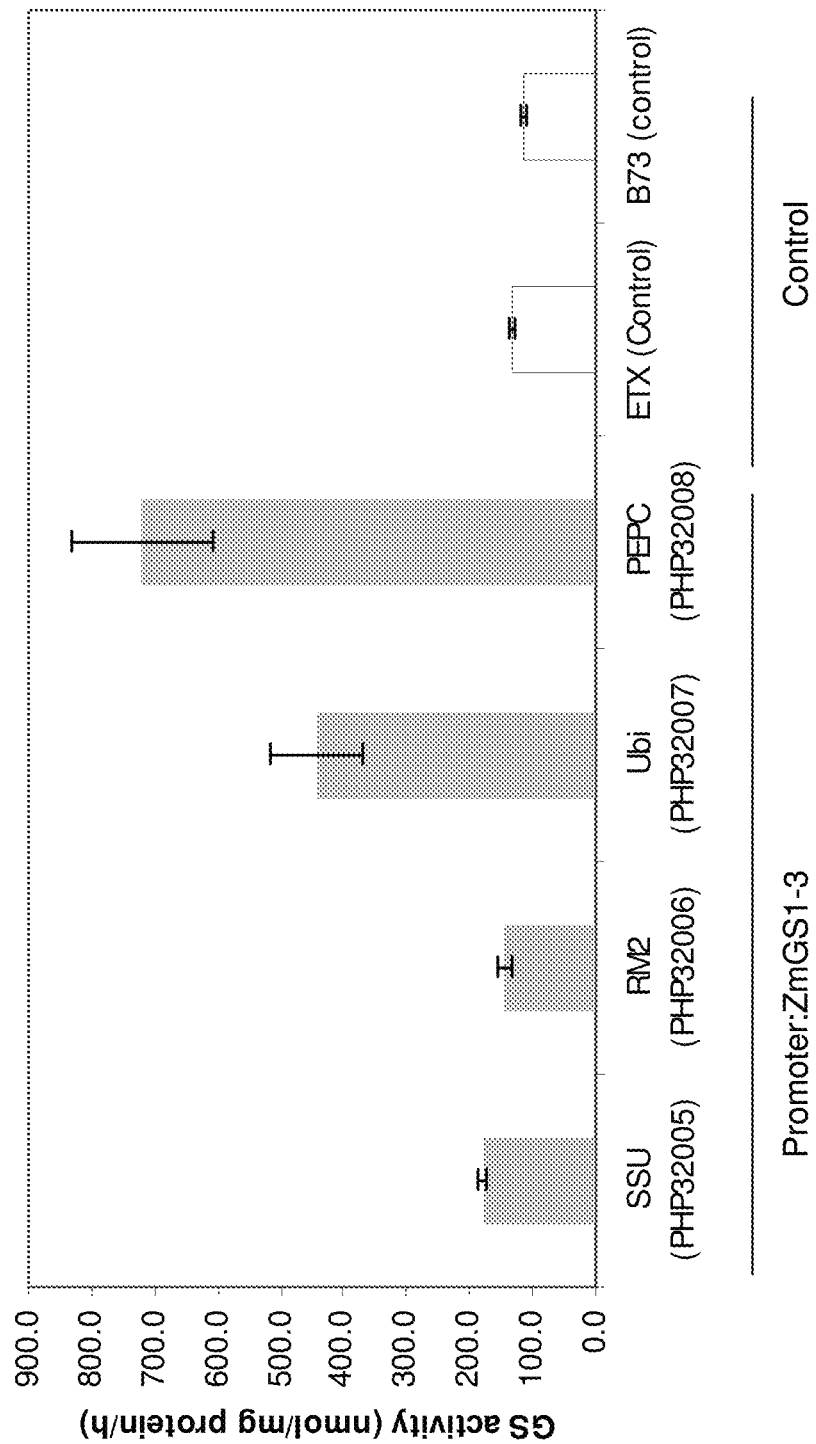
Figure 4C:
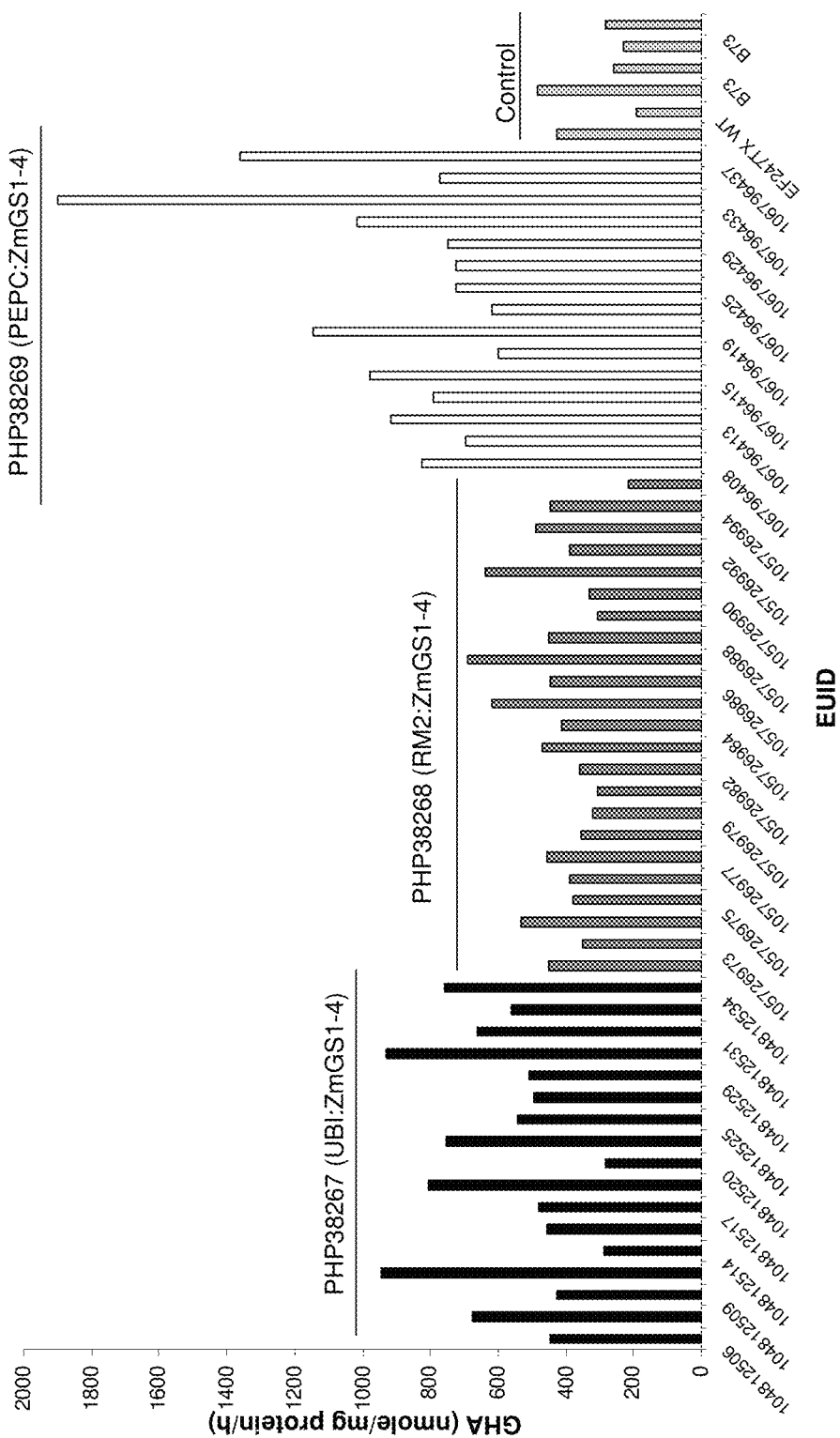
Figure 4D:
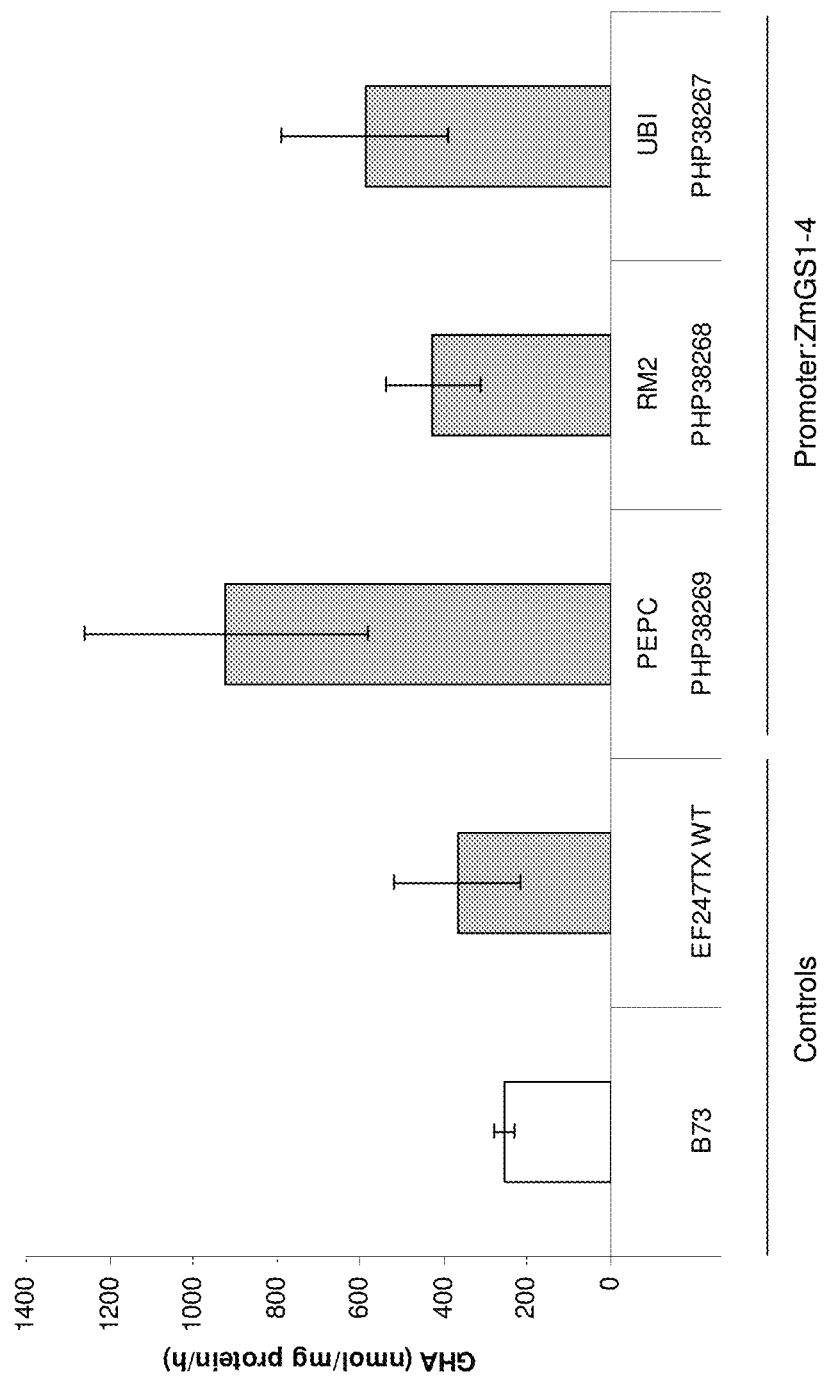

GS enzyme activity was determined in the leaves of field-grown T0 transgenic events transformed with PHP32005, 32006, 32007, 32008, 38267, 28268 and 38269 in an inbred, ETX. The results from the individual events (FIG. 4A, 4C) and average of all the events (FIG. 4B, 4D) for each construct are summarized. In case of ZM-GS1-3 over-expression PHPs, the highest activity (on an average 12× higher) was observed in PHP32008 (ZmPEPC1 PRO: ZmGS1-3) followed by PHP32007 (ZmUBI PRO:ZmGS1-3) where the activity was slightly higher than the controls in PHP32005 (pZmSSU PRO:ZmGS1-3). In case of PHP32006 (ZmRM2 PRO:ZmGS1-3) leaf samples the activity was comparable to control as expected because RM2 is a root-preferred promoter. The roots of these events, however, showed significantly higher GS activity as compare to non-transgenic sibs. In the case of ZM-GS1-4 over-expression PHPs the highest GS activity was observed in PHP38269 (pZM-PEPC::ZM-GS1-4) followed by PHP38267 (pZM-UBI::ZM-GS1-4). In the case of PHP32268 (ZmRM2 PRO:ZmGS1-4) leaf samples the activity was comparable to control, as is expected because RM2 promoter is a root-preferred promoter. The average activities of all the events in each construct are summarized in FIGS. 4B and 4D.

Figure 5A:
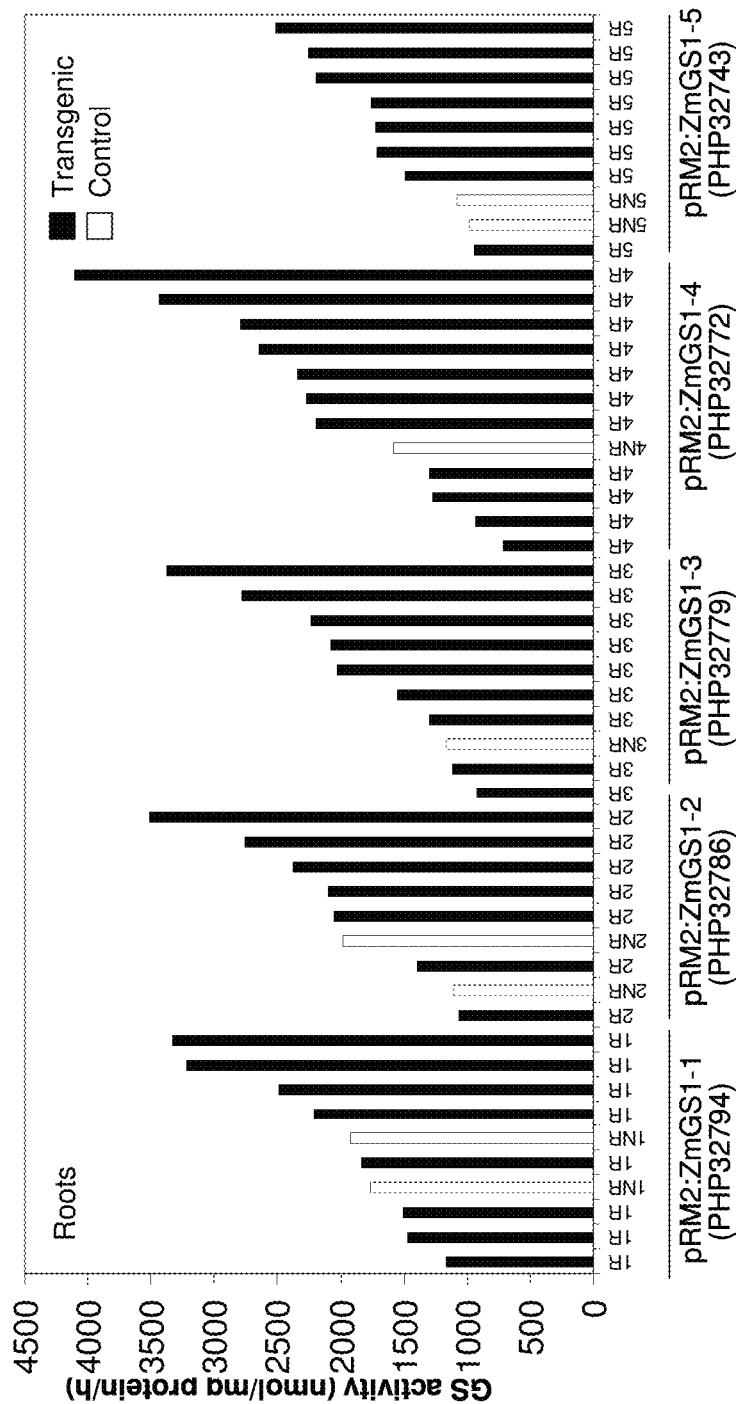
FIG. 5A, FIG. 5B.
Figure 5B:
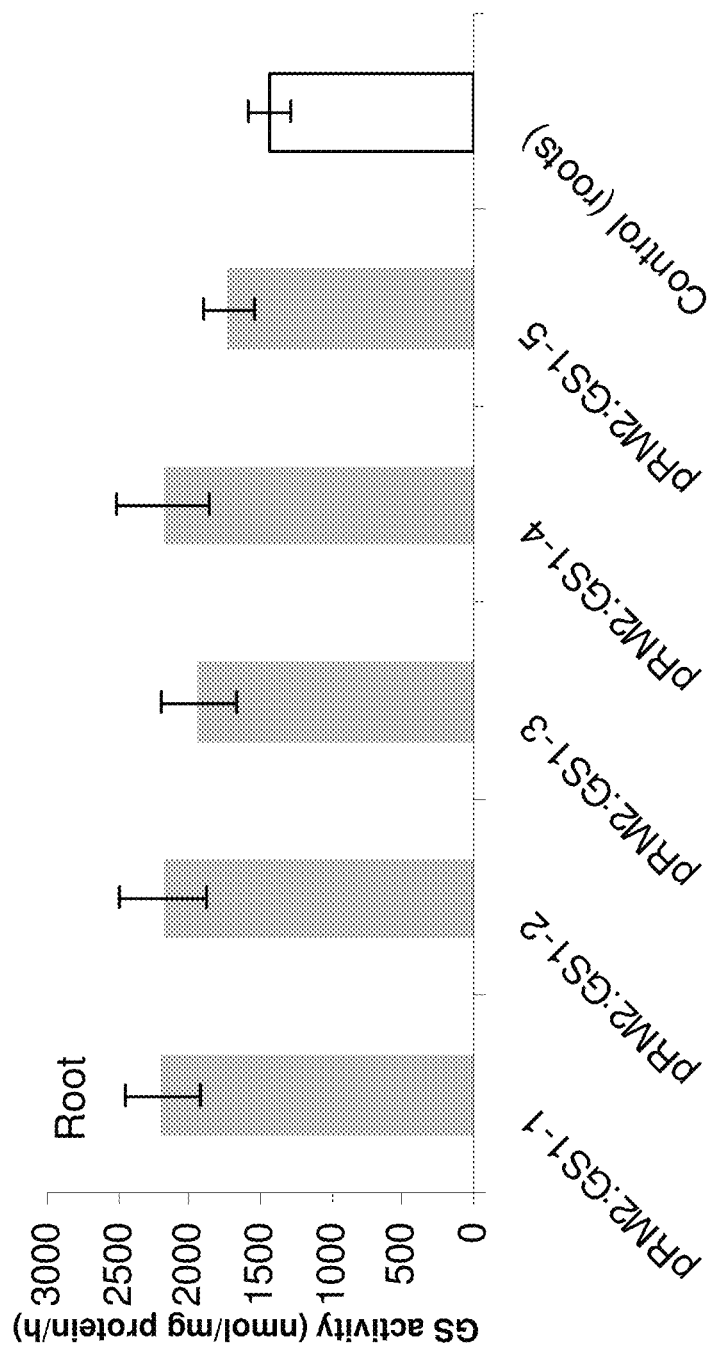
Figure 5C:
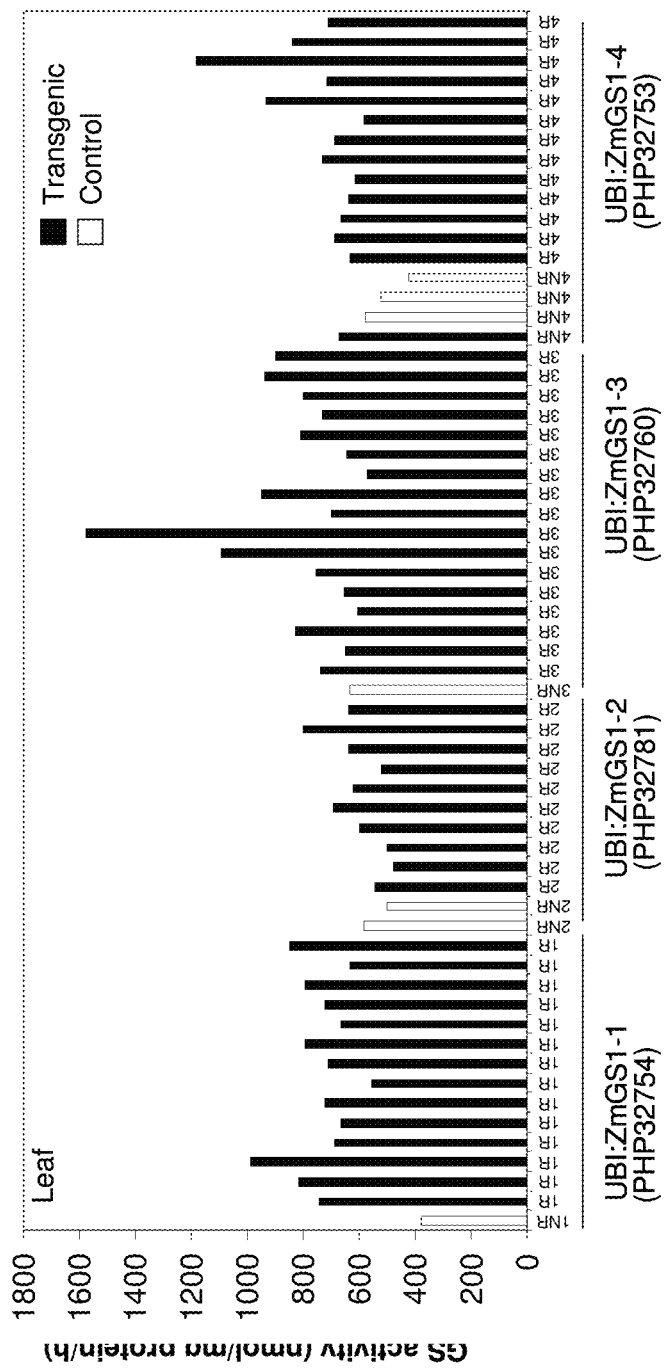
FIG. 5C, and FIG. 5D GS activity in roots and leaves of T1 events of FAST corn all five isoforms ZM-GS1 were also over-expressed in FAST (Functional Analyses System Traits) (see, U.S. patent application Ser. No. 10/367,417, filed Feb. 13, 2003) corn system under the control of a root-preferred (RM2) or constitutive promoters (UBI). Transgenic seeds segregating 1:1 hemizygous and wildtype were separated using ELISA and planted in 4 inch square plastic pots filled with Turface MVP® and thinned to 1 plant per pot after emergence. Three weeks after germination and growth under normal N condition, the leaves and roots were harvested for GS enzyme activity analyses. The GS activities in individual events and the average of all the events within a PHP are shown in FIG. 5A, FIG. 5C and FIG. 5B, FIG. 5D, respectively. In case of transgenic events where various GS1 isoforms were driven by a root preferred promoter (RM2), significantly higher GS activities were observed in roots as compare to null controls (FIG. 5A, FIG. 5B). In case of a constitutive promoter (UBI) driven GS1 isoforms events, a higher GS activity was observed as compared to null controls (FIG. 5C, FIG. 5D).
Figure 5D:
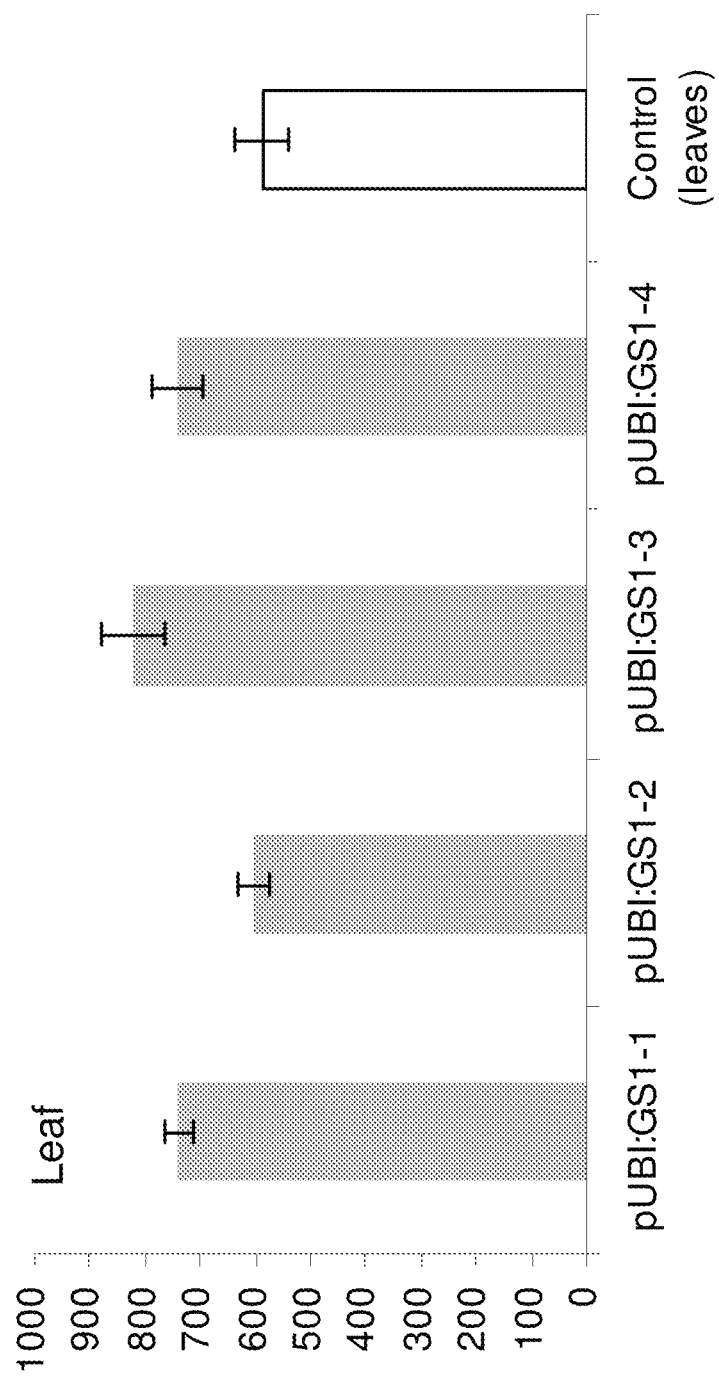

As described in Table 2, all five isoforms ZM-GS1 were also over-expressed in FAST corn system under the control of a root-preferred (RM2) or constitutive promoters (UBI). T1 seeds of all these transgenic events along with non-transgenic segregating seeds were grown in Turface. Three weeks after germination, the leaves and roots were harvested for GS enzyme activity analyses. The results from these experiments are summarized in FIG. 5. For the transgenic events where various GS1 isoforms were driven by a root-preferred promoter (RM2), significantly higher GS activities were observed in roots as compare to null controls (FIG. 5A, 5B). In the constitutive promoter (UBI) driven GS1 isoforms events, GS activity was increased as compared to null controls (FIG. 5C, 5D).

Example 8

Improved Specific Growth Rate (SGR) in T0 FAST Events

Figure 6A:
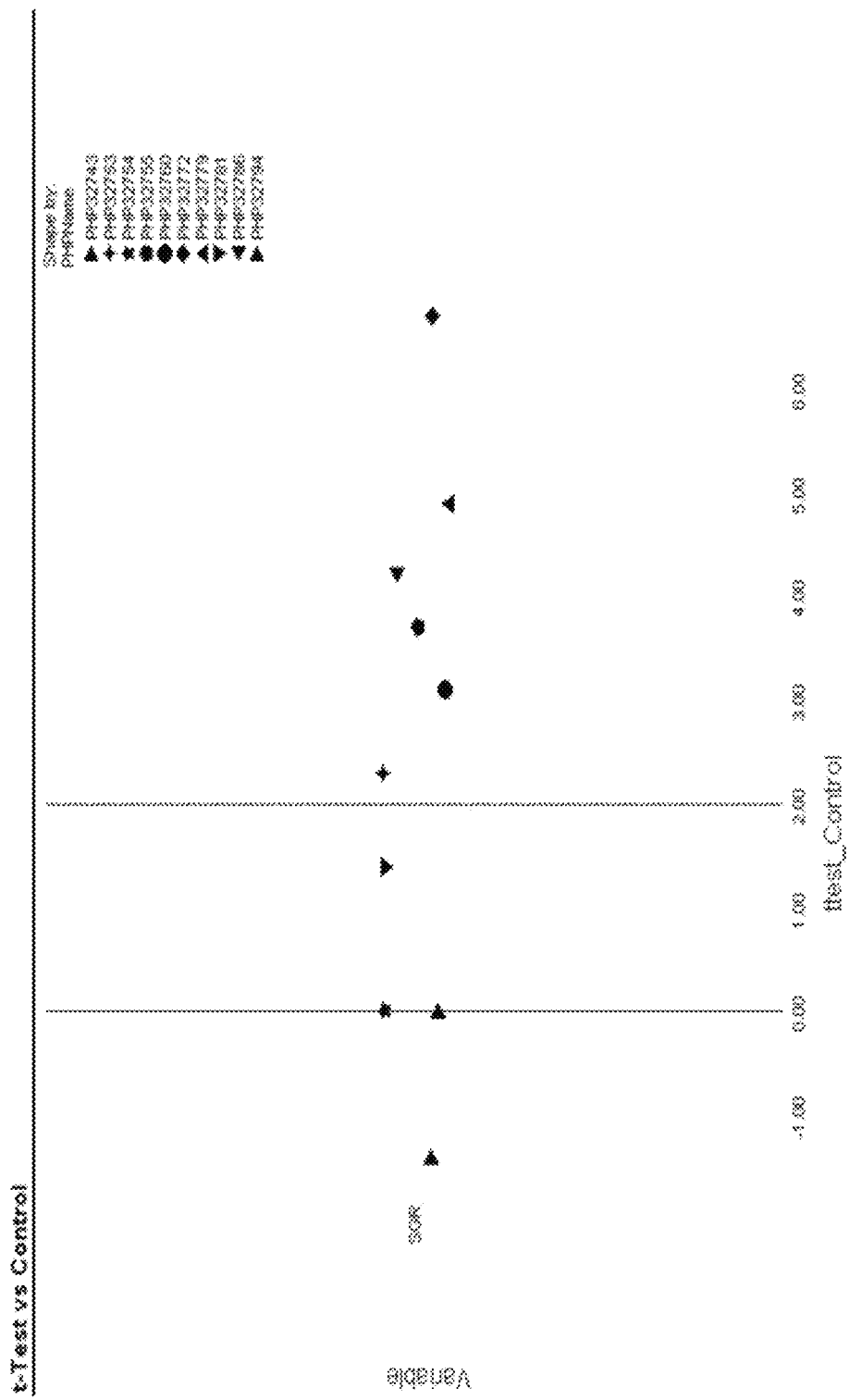
FIG. 6A and FIG. 6B Improved specific growth rate in T0 events of FAST corn. Five isoforms of ZM-GS1 were over-expressed in FAST corn system under the control of a root-preferred (RM2) or constitutive promoters (UBI). On an average, 10 independent transgenic events were generated from each construct. (See, U.S. patent application Ser. No. 10/367,417, filed Feb. 13, 2003). In all the T0 events, measurements recorded included but were not limited to specific growth rate, maximum total area, days to shed, seed number, ear length and yield estimates. The data from specific growth rate (SGR, measured from 14-28 days after germination) from this experiment are shown in FIG. 6A and FIG. 6B. Most of the events from each of the 6 constructs (out of total 10) tested showed significantly better specific growth rate as compare to controls (0.00) (FIG. 6A). PHP32772 (RM2 PRO:ZmGS1-4) performed best with a P value $>10^{-6}$ followed by PHP32779 (RM2 PRO:ZmGS1-3) with a P value $>10^{-6}$ (FIG. 6A). Other 4 constructs also show better SGR with a P value ranging from $10^{-2}$ to $10^{-4}$) (FIG. 6A). Most of the events in each construct performed significantly better than control (FIG. 6B). More than 80% and 70% events exceeded the performance of control in PHP32779 and 32772, respectively (FIG. 6B).
Figure 6B:
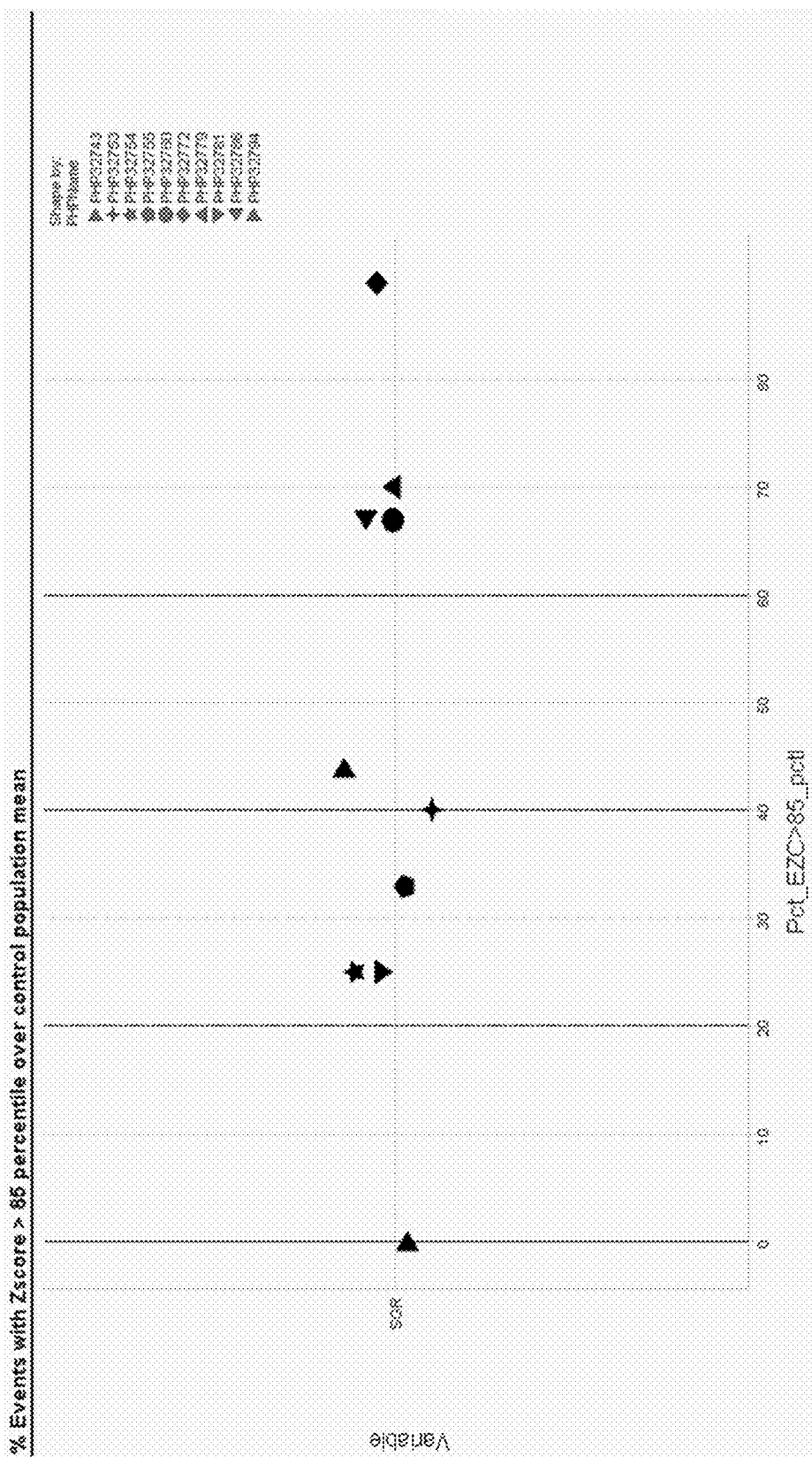

As described in Table 2, all five isoforms ZM-GS1 were also over-expressed in FAST corn system under the control of a root-preferred (RM2) or constitutive promoters (UBI). On an average, 10 independent transgenic events were generated from each construct. In all the T0 events, measurements recorded included but were not limited to specific growth rate, max total area, days to shed, seed number, ear length and yield estimates. The data from specific growth rate (SGR, measured from 14-28 days after germination) from this experiment are shown in FIG. 6. Most of the events from each of the 6 constructs (out of total 10) tested showed significantly better specific growth rate as compare to controls (0.00) (FIG. 6, upper panel). PHP32772 (RM2 PRO: ZmGS1-4) performed best with a P value >$10^{-6}$ followed by PHP32779 (RM2 PRO:ZmGS1-3) with a P value $10^{-6}$ (FIG. 6a). Other 4 constructs also show better SGR with a P value ranging from $10^{-2}$ to $10^{-4}$ (FIG. 6A). Most of the events in each construct performed significantly better than control (FIG. 6B). For example, more than 80% and 70% events exceeded the performance of control in PHP32779 and 32779, respectively (FIG. 6B).

Example 9

Improved a Agronomic Traits in T FAST Events of PHP32743 ZM-RM2-PRO:ZM-GS1-5)

Figure 7:
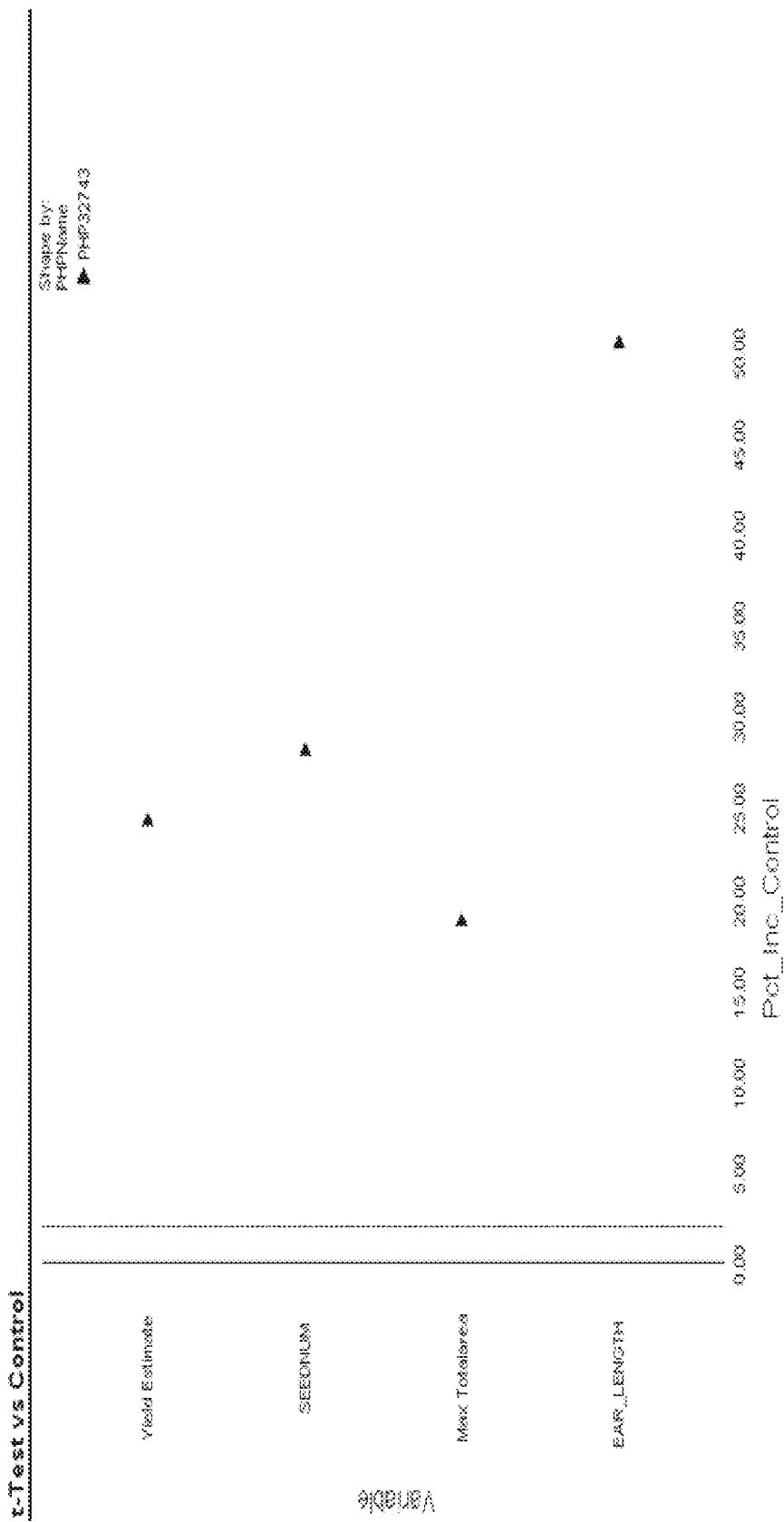
FIG. 7 Improved agronomic traits in T0 FAST events of PHP32743. Over-expression of ZM-GS1-5 under the control of a root-specific promoter resulted in improvement of several agronomic traits in T0 phenomics measurements. The results from average of nine events for several of these variables are summarized in FIG. 7. Multiple transgenic events from PHP32743 showed ~50% increase in ear length, ~25% increase in seed number and yield estimates and ~18% increase in maximum total area over the control.

Over-expression of ZM-GS1-5 under the control of a root-specific promoter resulted in improvement of several agronomic traits in T0 phenomics measurements. The results from average of nine events for several of these variables are summarized in FIG. 7. Multiple transgenic events from PHP32743 showed ~50% increase in ear length, ~25% increase in seed number and yield estimates and ~18% increase in maximum total area over the control.

Example 10

Figure 8A:
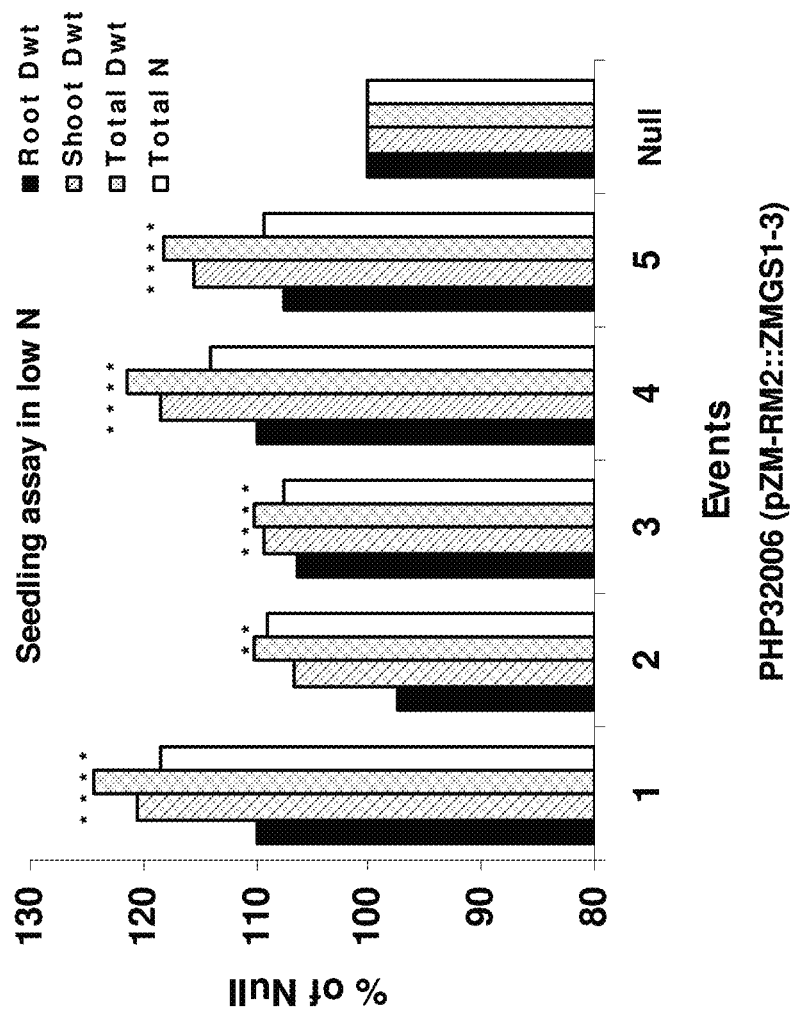
FIG. 8A and FIG. 8B Improved growth and N concentrations in PHP32006 (pZMRM2:ZmGS1-3) and PHP 32007 (pUBI:ZMGS1-3) in low N conditions. Testcross seeds of PHP32006 (FIG. 8A) and 32007 (FIG. 8B) were assayed in green house under low N conditions. The data for root dry weight, shoot dry weight, total dry weight and total N were collected. Four out of six and 3 out of 5 events were significantly better (denotes with asterisk in FIG. 8A and FIG. 8B) than null control in all the parameters measured in PHP32006 (FIG. 8A) and 32007 (FIG. 8B), respectively.
Figure 8B:
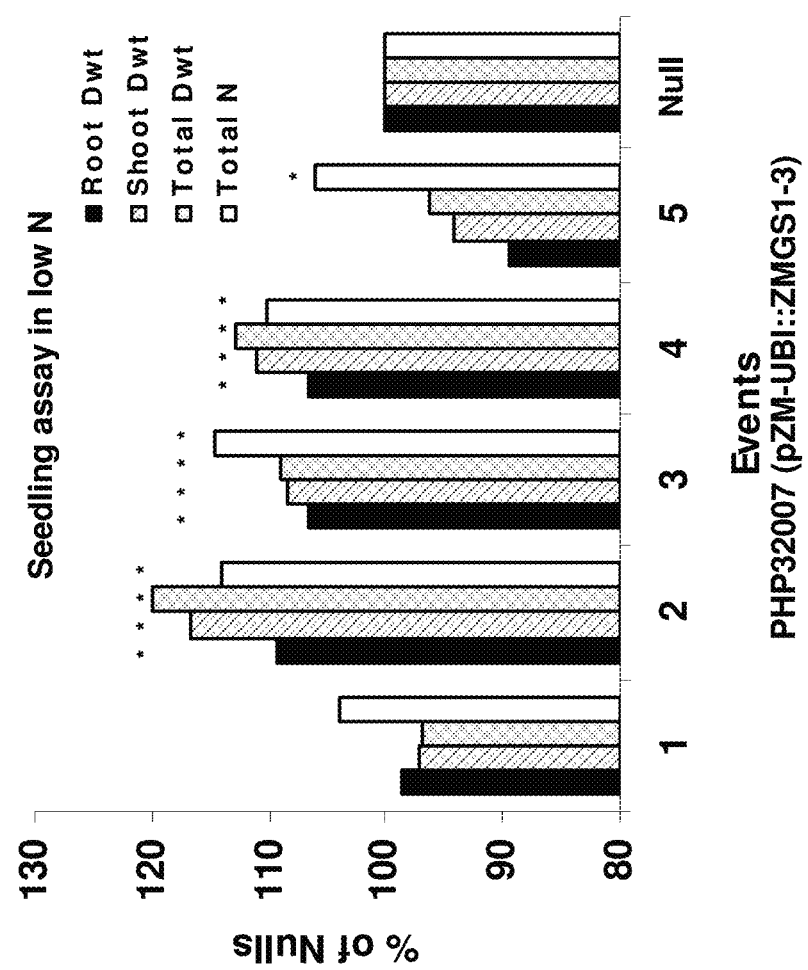

Improved Growth and N Concentrations in PHP32006 (pZMRM2:ZmGS1-3) and PHP 32007 (pUBI:ZMGS1-3) in Low N Conditions To test the effect of increased GS activity on plant performance, that is, alteration in growth rate, N concentration in the plant and total N accumulated, the plants were grown in a semi-hydroponics system similar to that described by Tollenaar and Migus (Tollenaar and Migus, (1984) Can J. Plant Sci. 64:465-485). Transgenic seeds from testcrosses segregating 1:1 hemizygous:wildtype for pRM2:ZMGS1-3 and pUBI:ZMGS1-3 were separated using a seed marker and planted, two seeds in each 4 inch square plastic pot filled with Turface MVP® and thinned to 1 plant per pot after emergnce. These were watered four times a day with 400 ml of nutrient solution (1 mM $KNO_3$, 2 mM $MgSO_4$, 1 mM $CaCl_2$, 0.5 mM $KH_2PO_4$, 3 mM KCl, 83 ppm Sprint330, 3 µM $H_3BO_4$, 1 µM $MnCl_2$, 1 µM $ZnSO_4$, 0.1 µM $CuSO_4$, 0.1 µM $NaMoO_4$ and sufficient $H_2SO_4$ to attain a pH of 5.5). Nineteen days after planting, seedlings were removed from the pot, the rooting material washed from the roots, the roots and shoots separated and the plant parts dried at 70° C. for 70 hr. Root, shoot and total dry weights were determined, the dried plants ground to a fine powder and approximately 35 mg tissue used to determine total reduced N by micro-Kjeldahl method (Yasuhura and Nokihara, (2001) J Agric Food Chem 49:4581-4583). Data were analyzed as described (Loussaert, (1992) Agron J. 84:256-259) and transgenic mean parameters compared to the corresponding null mean parameters. There were 9 replicates of each treatment combination. The data for root dry weight, shoot dry weight, total dry weight and total N were collected and summarized in FIG. 8. Four out of six and 3 out of 5 events significantly outperformed (denotes with asterisk in FIGS. 8a and 8b) the null control for all the parameters measured in PHP32006 (FIG. 8a) and 32007 (FIG. 8b), respectively.

Example 12

Variants of GS Sequences

A. Variant Nucleotide Sequences of GS that do not Alter the Encoded Amino Acid Sequence The GS nucleotide sequences are used to generate variant nucleotide sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO. These functional variants are generated using a standard codon table. While the nucleotide sequence of the variants are altered, the amino acid sequence encoded by the open reading frames do not change.

B. Variant Amino Acid Sequences of GS Polypeptides

Variant amino acid sequences of the GS polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using the protein alignment set forth in FIG. 1, an appropriate amino acid can be changed. Once the targeted amino acid is identified, the procedure outlined in the following section C is followed. Variants having about 70%, 75%, 80%, 85%, 90% and 95% nucleic acid sequence identity are generated using this method.

C. Additional Variant Amino Acid Sequences of GS Polypeptides

In this example, artificial protein sequences are created having 80%, 85%, 90% and 95% identity relative to the reference protein sequence. This latter effort requires identifying conserved and variable regions from the alignment set forth in FIG. 1 and then the judicious application of an amino acid substitutions table. These parts will be discussed in more detail below.

Largely, the determination of which amino acid sequences are altered is made based on the conserved regions among GS protein or among the other GS polypeptides. Based on the sequence alignment, the various regions of the GS polypeptide that can likely be altered are represented in lower case letters, while the conserved regions are represented by capital letters. It is recognized that conservative substitutions can be made in the conserved regions below without altering function. In addition, one of skill will understand that functional variants of the GS sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 3.

TABLE 3

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |

TABLE 3-continued

Substitution Table

| Amino Acid | Strongly Similar and Optimal Substitution | Rank of Order to Change | Comment |
|---|---|---|---|
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the GS polypeptides are generating having about 80%, 85%, 90% and 95% amino acid identity to the starting unaltered ORF nucleotide sequence of SEQ ID NO: 43, 45, 47, 49, 51 and 53.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. A method of increasing yield in a maize plant, the method comprising:
   a. increasing expression of a polynucleotide encoding a glutamine synthetase in the maize plant, wherein the polynucleotide is operably linked to a heterologous regulatory element, and wherein the glutamine synthetase comprises an amino acid sequence that has at least 90% sequence identity to SEQ ID NO: 52; and
   b. growing the maize plant in a plant growing environment thereby increasing the yield.

2. The method of claim 1, wherein the amino acid sequence has at least 95% sequence identity to SEQ ID NO: 52.

3. The method of claim 1, wherein the amino acid sequence is SEQ ID NO: 52.

4. The method of claim 1, wherein the regulatory element is a root-preferred promoter.

5. The method of claim 1, wherein the yield is grain yield.

* * * * *